(12) United States Patent
Waataja et al.

(10) Patent No.: US 11,534,610 B2
(45) Date of Patent: Dec. 27, 2022

(54) HIGH-FREQUENCY LOW DUTY CYCLE PATTERNS FOR NEURAL REGULATION

(71) Applicant: EnteroMedics Inc., St. Paul, MN (US)

(72) Inventors: Jonathan J. Waataja, Plymouth, MN (US); Adrianus P. Donders, Andover, MN (US)

(73) Assignee: ReShape Lifesciences Inc., San Clemente, CA (US)

( * ) Notice: Subject to any disclaimer, the term of this patent is extended or adjusted under 35 U.S.C. 154(b) by 203 days.

(21) Appl. No.: 15/423,044

(22) Filed: Feb. 2, 2017

(65) Prior Publication Data

US 2017/0216602 A1    Aug. 3, 2017

Related U.S. Application Data

(60) Provisional application No. 62/406,668, filed on Oct. 11, 2016, provisional application No. 62/290,095, filed on Feb. 2, 2016.

(51) Int. Cl.
*A61N 1/36* (2006.01)

(52) U.S. Cl.
CPC ..... *A61N 1/36171* (2013.01); *A61N 1/36007* (2013.01); *A61N 1/36117* (2013.01); *A61N 1/36153* (2013.01); *A61N 1/36175* (2013.01); *A61N 1/36178* (2013.01)

(58) Field of Classification Search
CPC .................. A61N 1/36175; A61N 1/36171
See application file for complete search history.

(56) References Cited

U.S. PATENT DOCUMENTS

| 2007/0203521 A1 | 8/2007 | Dobak |
| 2009/0312818 A1 | 12/2009 | Horsager et al. |
| 2010/0331916 A1* | 12/2010 | Parramon .......... A61N 1/36164 607/60 |
| 2013/0237948 A1 | 9/2013 | Donders et al. |

OTHER PUBLICATIONS

International Search Report and Written Opinion for PCT/US2017/016218), dated May 3, 2017.

* cited by examiner

*Primary Examiner* — Alyssa M Alter
(74) *Attorney, Agent, or Firm* — Merchant & Gould P.C.

(57) ABSTRACT

A method of downregulating and/or upregulating neural activity by applying a high frequency alternating current electrical signal to a nerve in a subject is disclosed. The signal comprises more than one microsecond cycle comprising one or more periods, each period comprising a charge recharge phase, and optionally, a pulse delay, each period having a frequency of at least 1000 Hz; and a microsecond inactive phase. In embodiments, an electrical signal treatment comprises more than one microsecond cycle to form a millisecond cycle, each millisecond cycle separated by a millisecond inactive phase during an on time. In embodiments, the electrical signal patterns can differ in amplitude.

11 Claims, 28 Drawing Sheets

HIGH-FREQUENCY LOW DUTY CYCLE PATTERNS FOR NEURAL REGULATION

CROSS-REFERENCE TO RELATED APPLICATIONS

This application claims the benefit of U.S. Provisional Application No. 62/290,095 filed Feb. 2, 2016 and U.S. Provisional Application No. 62/406,668 filed Oct. 11, 2016, the disclosures of which are hereby incorporated in their entirety.

INTRODUCTION

The invention is directed to methods and systems for applying a high frequency alternating current electrical signal to downregulate and/or upregulate activity of a nerve. The method comprises a high frequency low duty cycle layered pattern of electrical signals characterized by cycles with charge and recharge phases followed by inactive phases on the scale of microseconds, on the scale of milliseconds, and/or on the scale of minutes.

High-Frequency Low Duty Cycle Patterns for Neural Regulation

Modulation of nerve activity is useful for the treatment of gastrointestinal conditions including obesity and other eating disorders, inflammatory conditions such as inflammatory bowel disease and pancreatitis, diabetes, and hypertension. Application of neural modulation in some circumstances can be accompanied by a loss of effectiveness. This loss of effectiveness can in part be due to compliance of the patient with charging of the implanted device and/or effects on the nerve. It is desirable to identify electrical signal therapies that can minimize loss of effectiveness and decrease energy requirements of the device.

SUMMARY

This disclosure describes systems and methods providing electrical signal therapy for downregulating and/or upregulating nerve activity in a subject. In embodiments, the electrical signal therapy provides more than one microsecond cycle comprising more than one period, each period comprising charge and recharge phase which may or may not have pulse delays, each period having a frequency of at least 1000 Hz; and a microsecond inactive phase. In embodiments, more than one microsecond cycle forms a millisecond cycle, each millisecond cycle being separated by a millisecond inactive phase. The length of time of the microsecond and/or millisecond inactive phases provides for the ability to vary how often electrical signal treatment is applied to the nerve during an on time, provides for downregulation and/or upregulation of neural activity, and provides energy savings as compared to electrical signal therapy not having inactive phases.

In embodiments, a method of applying an electrical signal having parameters that downregulate and/or upregulate nerve activity to a nerve in a subject comprises: applying the electrical signal to the nerve during an on time, wherein the electrical signal comprises more than one microsecond cycle comprising: a) more than one period, each period comprising a charge and recharge phase and optionally, one or more pulse delays, each period having a frequency of at least 1000 Hz; and b) a microsecond inactive phase. In embodiments, the microsecond inactive phase is longer than the period. In embodiments, the length of the inactive phase can vary between each period. In embodiments, the period is about 1000 microseconds or less. In embodiments, the microsecond inactive phase is in a ratio to the period of about 10 to 1, 8 to 1, 6 to 1, 4 to 1, or 2 to 1. In embodiments, the microsecond inactive phase is at least about 80 microseconds. In embodiments, the microsecond inactive phase is at least 80 microseconds up to 10,000 microseconds, 200 microseconds up to 10,000 microseconds, or 400 microseconds up to 10,000 microseconds.

In embodiments, the duty cycle for the microsecond cycle is about 75% or less. In embodiments, the frequency is at least 1000 Hz, 2000 Hz, 3000 Hz, 4000 Hz, 5000 Hz, 6000 Hz, 7000 Hz, 8000 Hz, 9000 Hz, 10,000 Hz, 11,000 Hz, 12,000 Hz, 13,000 Hz, 14,000 Hz, 15,000 Hz, 16,000 Hz, 17,000 Hz, 18,000 Hz, 19,000 Hz, 20,000 Hz, 21,000 Hz, 22,000 Hz, 23,000 Hz, 24,000 Hz, 25,000 Hz or more. In embodiments, electrical signals at such frequencies can downregulate nerve activity.

In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

In other embodiments, the method comprises applying an electrical signal to a nerve in a subject, wherein the electrical signal comprises more than one microsecond cycle to form a millisecond active phase, and applying more than one millisecond active phase during the on time, wherein each millisecond active phase is separated by a millisecond inactive phase during the on time. In embodiments, the millisecond inactive phase is longer than the millisecond active phase. In embodiments, the millisecond inactive phase can vary in time between each millisecond active phase.

In embodiments, the millisecond active phase is at least 0.16 milliseconds. In embodiments, the millisecond active phase is 0.16 millisecond to 1,100 milliseconds, 0.16 millisecond to 900 milliseconds, 0.16 millisecond to 800 milliseconds, 0.16 millisecond to 700 milliseconds, 0.16 millisecond to 600 milliseconds, 0.16 millisecond to 500 milliseconds, 0.16 to 400 milliseconds, 0.16 to 300 milliseconds, 0.16 to 200 milliseconds, 0.16 to 100 milliseconds, 0.16 to 50 milliseconds, 0.16 to 40 milliseconds, 0.16 to 30 milliseconds, 0.16 to 20 milliseconds, 0.16 to 10 milliseconds, or 0.16 to 5 milliseconds. In embodiments, the millisecond active phase is at least 1 millisecond. In other embodiments, the millisecond active phase is 1 to 1,100 milliseconds, 1 millisecond to 900 milliseconds, 1 millisecond to 800 milliseconds, 1 millisecond to 700 milliseconds, 1 millisecond to 600 milliseconds, 1 millisecond to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, 1 to 10 milliseconds, or 1 to 5 milliseconds.

In embodiments, the millisecond active phase comprises at least 2 to 100 microsecond cycles, at least 2 to 90, at least 2 to 80, at least 2 to 70, at least 2 to 60, at least 2 to 50, at least 2 to 40, at least 2 to 30, at least 2 to 20, at least 2 to 10, at least 2 to 5, or at least 2 to 4 microsecond cycles.

In embodiments, the millisecond inactive phase is in a ratio to the millisecond active phase of about 10 to 1, 8 to 1, 6 to 1, 4 to 1, 2 to 1 or 1 to 2. In embodiments, the millisecond inactive phase is at least 0.08 milliseconds. In embodiments, the millisecond inactive phase is 0.08 millisecond to 11,000 milliseconds, 0.08 millisecond to 9000 milliseconds, 0.08 millisecond to 8000 milliseconds, 0.08 millisecond to 7000 milliseconds, 0.08 millisecond to 6000 milliseconds, 0.08 millisecond to 5000 milliseconds, 0.08 to 4000 milliseconds, 0.08 to 3000 milliseconds, 0.08 to 2000 milliseconds, 0.08 to 1000 milliseconds, 0.08 to 500 milliseconds, 0.08 to 400 milliseconds, 0.08 to 300 milliseconds, 0.08 to 200 milliseconds, 0.08 to 100 milliseconds, 0.08 to 50 milliseconds, 0.08 to 40 milliseconds, 0.08 to 30 milliseconds, 0.08 to 20 milliseconds, or 0.08 to 10 milliseconds. In embodiments, the millisecond inactive phase is 1 millisecond to 11,000 milliseconds, 1 millisecond to 9000 milliseconds, 1 millisecond to 8000 milliseconds, 1 millisecond to 7000 milliseconds, 1 millisecond to 6000 milliseconds, 1 millisecond to 5000 milliseconds, 1 to 4000 milliseconds, 1 to 3000 milliseconds, 1 to 2000 milliseconds, 1 to 1000 milliseconds, 1 to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, or 1 to 10 milliseconds.

In yet other embodiments, a method of applying an electrical signal having parameters to downregulate and/or upregulate nerve activity to a nerve in a subject comprising: applying the electrical signal to the nerve during an on time, wherein the electrical signal comprises a first pattern comprising at least one microsecond cycle; and a second pattern comprising more than one millisecond active phase, wherein each millisecond active phase comprises more than one microsecond cycle, and each millisecond active phase is separated by a millisecond inactive phase. In embodiments, the first and second patterns have different amplitude. In embodiments, a ramp up and/or ramp down in amplitude is employed to shift the change in amplitude.

In embodiments, the microsecond cycle comprises at least one period, each period comprising a charge and recharge phase, and optionally, a pulse delay, wherein each period has a frequency of at least 200 Hz; and a microsecond inactive phase.

In embodiments, the first pattern has amplitude greater than the second pattern. In embodiments, the first and second patterns are separated by a ramp up and/or a ramp down of amplitude. In embodiments, the ratio of the amplitude of the first pattern to the amplitude of the second pattern is at least 10 to 1, 8 to 1, 6 to 1, 4 to 1, 2 to 1 or 4 to 3.

In another aspect of the disclosure, the methods of the disclosure can be implemented by a computer, stored as instructions on a microprocessor, stored on an external device such as a mobile phone or charger, or on a computer readable medium.

In other aspects of the disclosure, a system is provided with a microprocessor configured to deliver an electrical signal to a nerve of a subject during an on time that comprises more than one microsecond cycle comprising more than one period, each period comprising a charge and recharge phase, and optionally, a pulse delay, and each period having a frequency of at least 1000 Hz; and a microsecond inactive phase. In other embodiments, the microprocessor is configured to deliver an electrical signal during an on time that comprises more than one microsecond cycle to form a millisecond active phase, and applying more than one millisecond active phase during the on time, wherein each millisecond active phase is separated by a millisecond inactive phase during the on time. In other embodiments, the microprocessor is configured to deliver an electrical signal to a nerve of a subject during an on time that comprises a first pattern that comprises at least one microsecond cycle; and a second pattern comprising more than one millisecond active phase, wherein each millisecond active phase comprises more than one microsecond cycle, and each millisecond active phase is separated by a millisecond inactive phase. In embodiments, the first and second patterns have different amplitude.

In another aspect of the disclosure, the systems and methods of the disclosure are useful to downregulate and/or upregulate activity on the nerve including but not limited to vagus nerve, renal nerve, renal artery, sympathetic nerves, splanchnic nerve, celiac plexus, and glossopharyngeal nerves. The systems and methods are useful in treating subjects having a disease or disorder including gastrointestinal disorders, obesity and eating disorders, pancreatitis and other inflammatory conditions, ulcerative colitis, Crohn's disease, diabetes, prediabetes, hypertension, and congestive heart failure.

DETAILED DESCRIPTION

Figure 1:
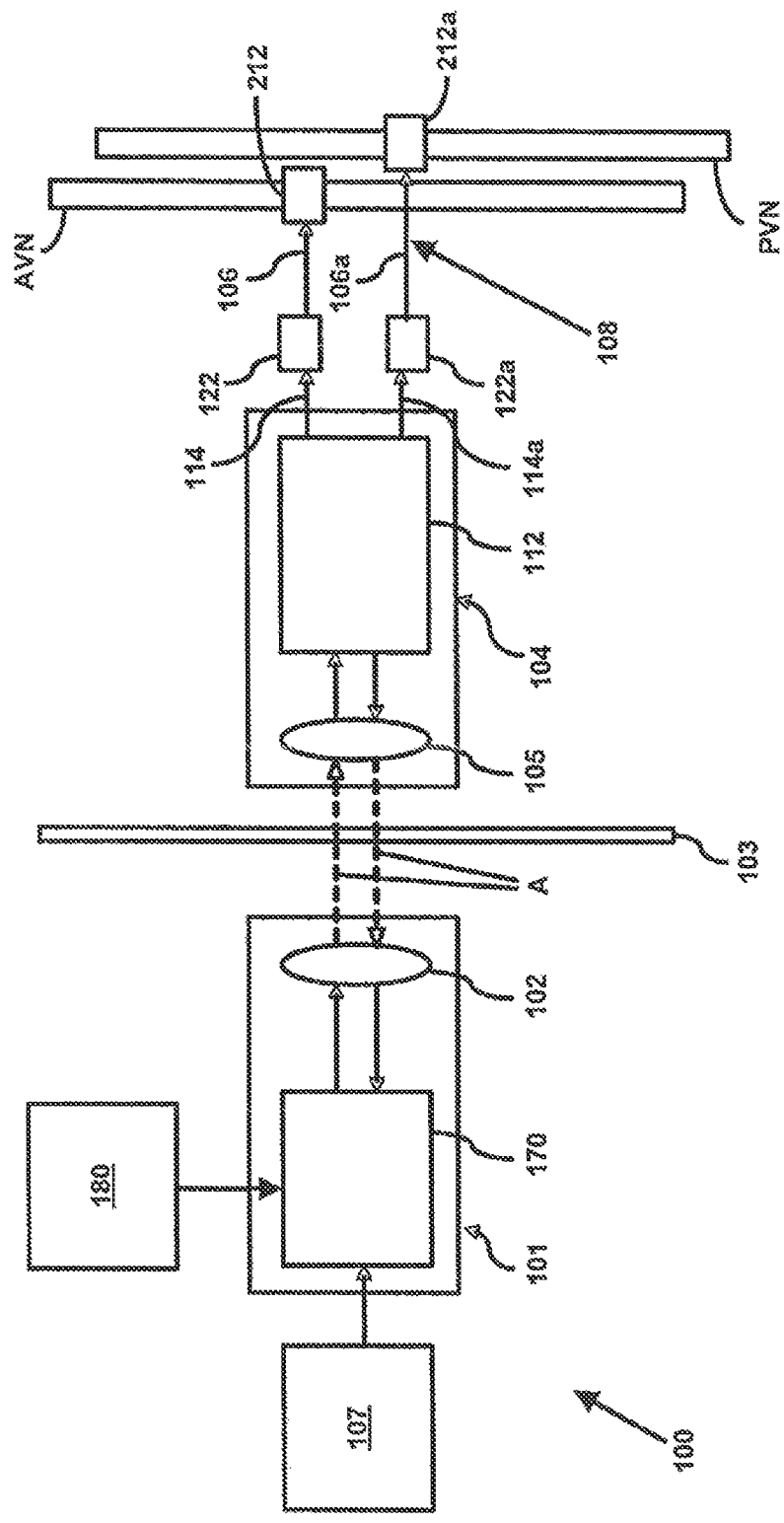
FIG. 1 is a schematic representation of a therapy system having features that are examples of inventive aspects of the principles of the present invention, the therapy system including a neuroregulator and an external charger.

The particulars shown herein are by way of example and for purposes of illustrative discussion of the invention. In this regard, no attempt is made to show structural details of the invention in more detail than is necessary for the fundamental understanding of the invention, the description taken with the drawings making apparent to those skilled in the art how the several forms of the invention may be embodied in practice.

Definitions

The term "about" is not intended to either expand or limit the degree of equivalents which may otherwise be afforded a particular value. The term "about" in the context of the present disclosure means a value within 10% (±10%) of the value recited immediately after the term "about," including any numeric value within this range, the value equal to the upper limit (i.e., +10%) and the value equal to the lower limit (i.e., −10%) of this range. For example, the value "100" encompasses any numeric value that is between 90 and 110, including 90 and 110 (with the exception of "100%", which always has an upper limit of 100%).

"AC" as used herein means alternating current.

"Charge Phase" as used herein means a pulse of charge applied to the nerve.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

"Cycle" as used herein means one repetition of a repetitive pattern of electrical signals.

"Duty Cycle" as used herein means the percentage of time charge is delivered to the nerve in one cycle. In embodiments, duty cycle can be modified by decreasing pulse width and/or by adding inactive phases between pulses or both.

"Frequency" as used herein means the reciprocal of the period measured in Hertz.

"High Duty Cycle" as used herein refers to a pattern of electrical signals with a duty cycle of about 76% or greater.

"Low Duty Cycle" as used herein refers to a pattern of HFAC/HFAV signals with a duty cycle of about 75% or less.

"HFAC" as used herein refers to high frequency alternating current.

"HFAV" as used herein refers to high frequency alternating voltage.

"Hz" as used herein refers to Hertz.

"Inactive Phase" as used herein refers to a length of time when no charge is delivered to a nerve.

"Microsecond cycle" as used herein refers to application of an electrical signal in a period comprising at least one charge recharge phase; and a microsecond inactive phase. Optionally, a period includes a pulse delay after the charge phase and/or after the recharge phase.

"Microsecond Inactive Phase" as used herein means a period of time where no charge is being delivered to the nerve, as measured on a microsecond time scale. A microsecond inactive phase is identified in microseconds.

"Millisecond Active Phase" as used herein means a period of time where two or more microsecond cycles are applied to the nerve.

"Millisecond Cycle" as used herein refers to application of an electrical signal that comprises at least two microsecond cycles; and a millisecond inactive phase.

"Millisecond Inactive Phase" as used herein means a period of time wherein no charge is being delivered to the nerve, measured on a millisecond time scale. A millisecond inactive phase is identified in milliseconds.

"Off Time" as used herein refers to a period when no charge is being delivered to the nerve. In embodiments, off time is on the order of seconds and/or minutes.

"On Time" refers to a period of time in which multiple micro and/or millisecond cycles are applied to the nerve. In embodiments, on time is on the order of seconds and/or minutes.

"Period" refers to the length of time of one charge phase and one recharge phase, which can include one or more pulse delays.

"Pulse Amplitude" is the height of the pulse in amperes or voltage relative to the baseline.

"Pulse Delay" as used herein refers to an aspect of the period wherein the impedance across a parallel electrical path with the nerve is at or close to 0 Ohms, with the intention of avoiding any unwanted electrical signals being delivered to the nerve.

"Pulse Width" as used herein refers to the length of time of the pulse.

"Ramp Down" as used herein refers to the period at the end of the application of an electrical signal, or between different patterns of electrical signals, to a nerve of a patient where the pulse amplitude of the signal decreases.

"Ramp Up" as used herein refers to increasing the pulse amplitude until the amplitude desired for therapy is reached at the start of an applied electrical signal or between different patterns of electrical signals. The starting amplitude of ramping may be below the current/voltage threshold of blocking "Therapy Cycle" as used herein refers to a discrete period of time that contains one or more on times and off times. The pattern of on and off times within the therapy cycle can be repetitive, non-fixed or randomized throughout a therapy schedule.

"Therapy Parameters" as used herein includes, but is not limited to, frequency, pulse width, pulse amplitude, on time, off time and pattern of electrical signals.

"Therapy Schedule" as used herein refers to the time of day when therapy cycles start, the number of therapy cycles, timing of therapy cycles and duration of the delivery of therapy cycles for at least one day of the week.

When ranges are provided, the range includes both endpoint numbers as well as all real numbers in between. For example, a range of 200 Hz to 25 kHz includes 201 to 25 kHz, 202 to 25 kHz, and so on, as well as 24,999 Hz to 200 Hz, 24,998 Hz to 200 Hz and so on, and 201 Hz to 24,999 Hz, 202 Hz to 24,998 Hz, and so on.

With reference now to the various drawing figures in which identical elements are numbered identically throughout, a description of embodiments of the present disclosure will now be described.

A. Therapy System

FIG. 1 schematically illustrates a therapy system 100. The therapy system 100 includes a neuroregulator 104, an electrical lead arrangement 108, and an external charger 101. The neuroregulator 104 is adapted for implantation within a patient. As will be more fully described herein, the neuroregulator 104 typically is implanted just beneath a skin layer 103.

The neuroregulator 104 is configured to connect electrically to the lead arrangement 108. In general, the lead arrangement 108 includes two or more (first and second) electrical lead assemblies 106, 106a. In embodiments, a single lead comprises at least two electrodes. In other embodiments, each lead comprises a single electrode. In the example shown, the lead arrangement 108 includes first and second (bipolar) electrical lead assemblies 106, 106a. The neuroregulator 104 generates therapy signals and transmits the therapy signals to the first and second lead assemblies 106, 106a.

The first and second lead assemblies 106, 106a stimulate and/or block conduction nerves of a patient based on the therapy signals provided by the neuroregulator 104. In an embodiment, first and second lead assemblies 106, 106a include first and second distal electrodes 212, 212a, which are placed on one or more nerves of a patient. For example, the electrodes 212, 212a may be individually placed on the anterior vagal nerve AVN and posterior vagal nerve PVN, respectively, of a patient. In an embodiment, first and second lead assemblies 212, 212a can be placed on the vagal nerve at a subdiaphragmatic location. For example, the distal electrodes 212, 212a can be placed just below the patient's diaphragm. In other embodiments, however, fewer or more electrodes can be placed on or near fewer or more nerves.

The external charger 101 includes circuitry for communicating with the implanted neuroregulator 104. In general, communication is transmitted across the skin 103 along a two-way signal path as indicated by arrows A. Example communication signals transmitted between the external charger 101 and the neuroregulator 104 include therapy instructions, patient data, and other signals as will be described herein. Energy also can be transmitted from the external charger 101 to the neuroregulator 104 as will be described herein.

In the example shown, the external charger 101 can communicate with the implanted neuroregulator 104 via bidirectional telemetry (e.g. via radio frequency (RF) signals). The external charger 101 shown in FIG. 1 includes an external coil 102, which can send and receive RF signals. A similar internal coil 105 can be implanted within the patient and electrical communication with the neuroregulator 104. In an embodiment, the internal coil 105 is integral with the neuroregulator 104. The internal coil 105 serves to receive and transmit signals from and to the coil 102 of the external charger 101.

For example, the external charger 101 can encode the information as a bit stream by amplitude modulation or frequency modulation of an RF carrier wave. The signals transmitted between the external and internal coils 102, 105 preferably have a carrier frequency of about 6.78 MHz. For example, during an information communication phase, the value of a parameter can be transmitted by toggling a rectification level between half-wave rectification and no rectification. In other embodiments, however, higher or lower carrier wave frequencies may be used.

In an embodiment, the neuroregulator 104 communicates with the external charger 101 using load shifting (e.g., modification of the load induced on the external charger 101). This change in the load can be sensed by the inductively coupled external charger 101. In other embodiments, however, the neuroregulator 104 and external charger 101 can communicate using other types of signals.

In an embodiment, the neuroregulator 104 receives power to generate the therapy signals from an implantable power source 151 (see FIG. 3A), such as a battery. In a preferred embodiment, the power source 151 is a rechargeable battery. In some embodiments, the power source 151 can provide power to the implanted neuroregulator 104 when the external charger 101 is not connected. In other embodiments, the external charger 101 also can be configured to provide for periodic recharging of the internal power source 151 of the neuroregulator 104. In an alternative embodiment, however, the neuroregulator 104 can entirely depend upon power received from an external source. For example, the external charger 101 can transmit power to the neuroregulator 104 via an RF link (e.g., between coils 102, 105).

In embodiments, the neuroregulator 104 can be powered by a rechargeable battery 151, which is periodically charged by the application of the mobile charger 101, the latter being placed in close proximity to the implanted neuroregulator 104. Alternatively, the neuroregulator 104 can be directly powered by RF energy provided by the mobile charger 101. The choice of the mode of providing power is made via a setting of the mobile charger 101, or via the clinician programmer. In a further embodiment, charging of the rechargeable battery 151 in the neuroregulator 104, can be achieved by application of remote wireless energy. (Grajski et al, IEEE Microwave Workshop series on Innovative Wireless Power Transmission: Technology, Systems, and Applications, 2012 published on a4wp.org).

In some embodiments, the neuroregulator 104 initiates the generation and transmission of therapy signals to the first and second lead assemblies 106, 106a. In an embodiment, the neuroregulator 104 initiates therapy when powered by the internal battery 151. In other embodiments, however, the external charger 101 triggers the neuroregulator 104 to begin generating therapy signals. After receiving initiation signals from the external charger 101, the neuroregulator 104 generates the therapy signals and transmits the therapy signals to the first and second lead assemblies 106, 106a.

Figure 3A:
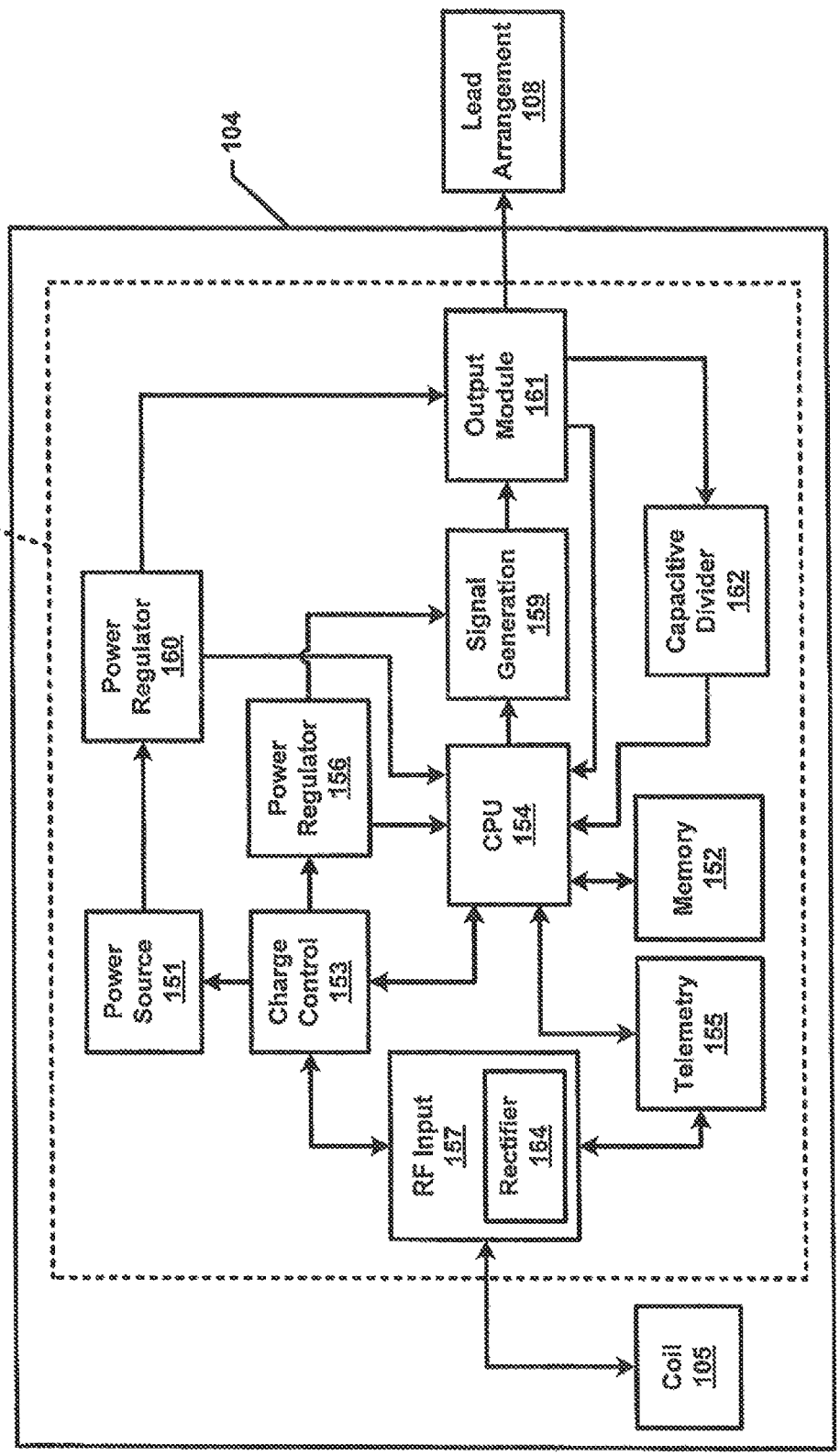
FIG. 3A is a block diagram of a representative circuit module for the neuroregulator of FIG. 2A and FIG. 2B according to aspects of the present disclosure.

In embodiments, the neuroregulator comprises a microprocessor (e.g. FIG. 3A; 154). In embodiments, a microprocessor is configured to deliver an electrical signal to a nerve of a subject during an on time that comprises more than one microsecond cycle comprising more than one period, each period comprising a charge recharge phase which may or may not have pulse delays, each period having a frequency of at least 1000 Hz; and a microsecond inactive phase.

In other embodiments, the microprocessor is configured to deliver an electrical signal to a nerve of a subject during an on time that comprises more than one microsecond cycle to form a millisecond active phase, and applying more than one millisecond active phase during the on time, wherein each millisecond active phase is separated by a millisecond inactive phase during the on time. In embodiments, a microsecond cycle comprises at least one period comprising a charge recharge phase, and optionally, a pulse delay, each period having a frequency of at least 200 Hz; and a microsecond inactive phase.

In other embodiments, the microprocessor is configured to deliver an electrical signal to a nerve of a subject during an on time that comprises a first pattern comprising at least one microsecond cycle; and a second pattern comprising more than one millisecond active phase, wherein each millisecond active phase comprises more than one microsecond cycle, and each millisecond active phase is separated by a millisecond inactive phase. In embodiments, the first and second patterns have a different amplitude. In embodiments, the first pattern and second pattern are separated by a ramp up and/or ramp down in amplitude.

In other embodiments, the external charger 101 also can provide the instructions according to which the therapy signals are generated (e.g., frequency, pulse-width, amplitude, and other such parameters). In a preferred embodiment, the external charger 101 includes memory 203 in which individual parameters, programs, and/or therapy schedules can be stored for transmission to the neuroregulator 104. In embodiments, those parameters include frequency, the time of a microsecond inactive phase, the time of a millisecond active phase, and/or the time of a millisecond inactive phase. In alternative embodiment, the parameters include frequency, the % of duty cycle of the microsecond cycle and/or the % of duty cycle of the millisecond cycle.

Selection of those parameters can be made by a user on a user interface (not shown). In embodiments, those parameters include pulse width, constant voltage settings, constant current settings, frequency, % duty cycle of the microsecond cycle and/or millisecond cycle, amplitude, microsecond inactive phase time, millisecond active phase time, and/or a millisecond inactive phase. The external charger 101 also can enable a user to select a parameter/program/therapy schedule as displayed on a user interface, and then be stored in memory for transmission to the neuroregulator 104. As disclosed herein each of the methods can form a therapy program. In another embodiment, the external charger 101 can provide therapy instructions with each initiation signal.

Typically, each of the parameters/programs/therapy schedules stored on the external charger 101 can be adjusted by a physician to suit the individual needs of the patient. For example, a computing device (e.g., a notebook computer, a personal computer, etc.) 107 can be communicatively connected to the external charger 101. With such a connection established, a physician can use the computing device 107 to program parameters and/or therapies into the external charger 101 for either storage or transmission to the neuroregulator 104.

The neuroregulator 104 also may include memory 152 (see FIG. 3A) in which therapy instructions and/or patient data can be stored. For example, the neuroregulator 104 can store therapy programs or individual parameters indicating what therapy should be delivered to the patient. The neuroregulator 104 also can store patient data indicating how the patient utilized the therapy system 100 and/or reacted to the delivered therapy.

What follows is the embodiment in which the neuroregulator 104 contains a rechargeable battery 151 from which the neuroregulator 104 draws power (FIG. 3A).

1. System Hardware Components a. Neuroregulator

Figure 2A:
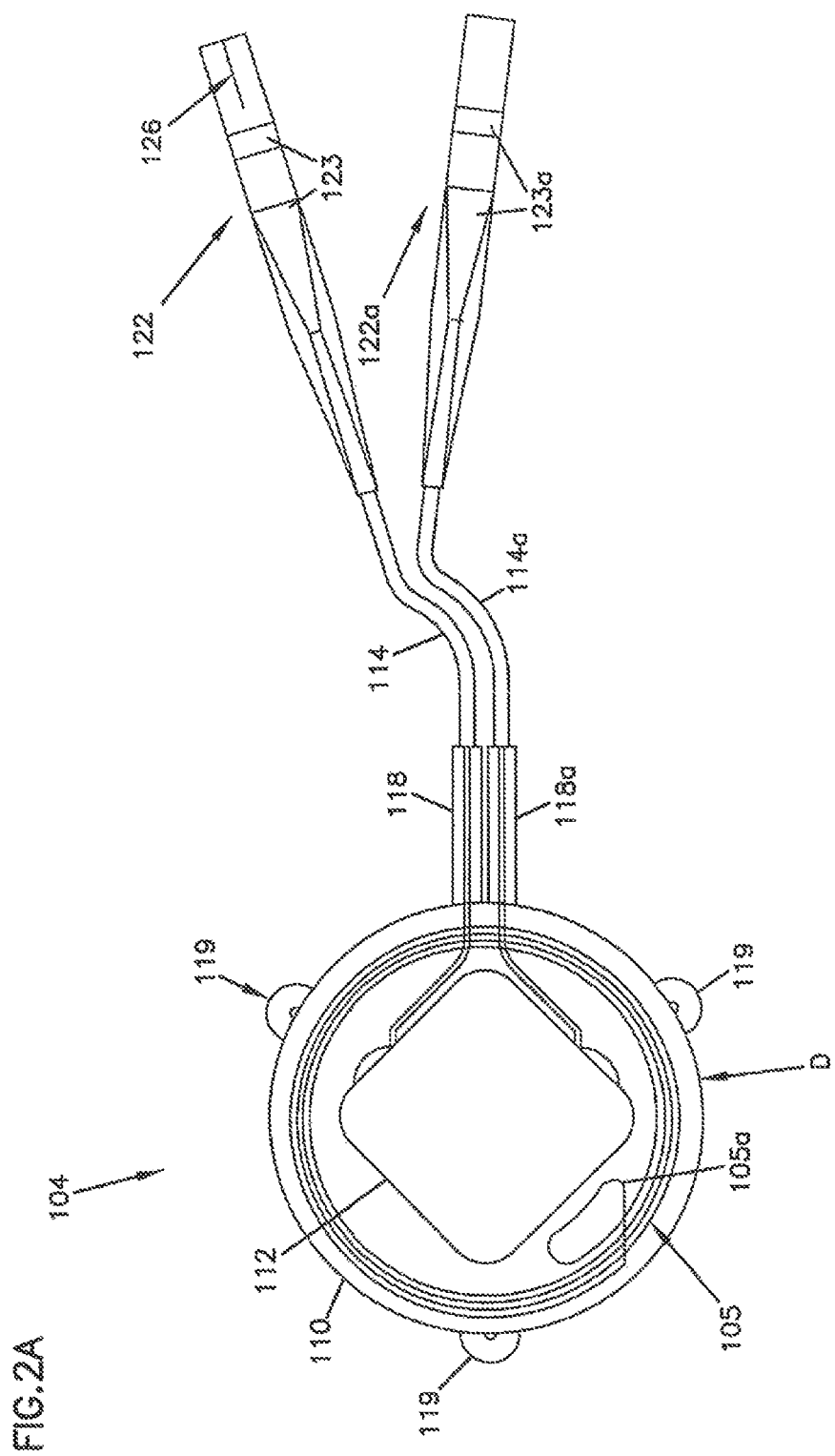
FIG. 2A is a plan view of an implantable neuroregulator for use in the therapy system of FIG. 1 according to aspects of the present disclosure.
Figure 2B:
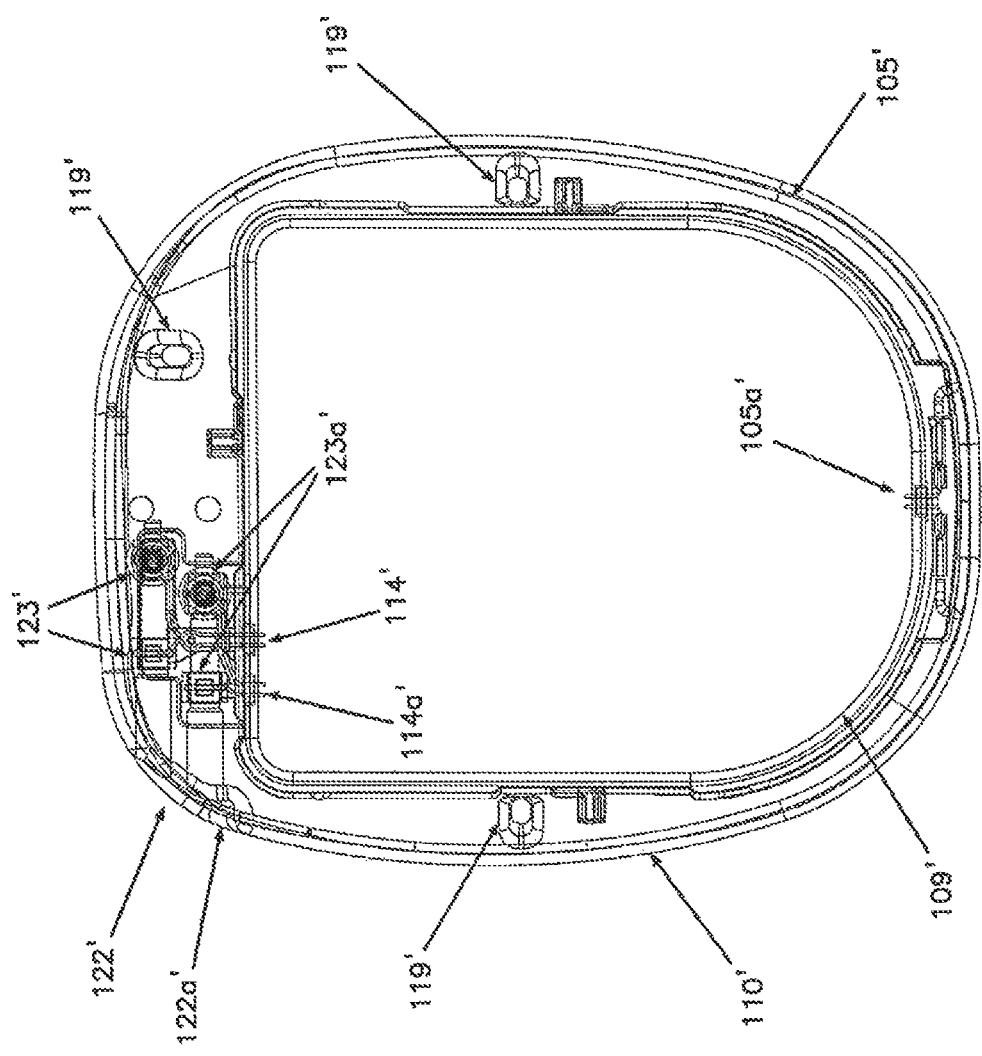
FIG. 2B is a plan view of another implantable neuroregulator for use in the therapy system of FIG. 1 according to aspects of the present disclosure.

Different embodiments of the neuroregulator 104, 104' are illustrated schematically in FIGS. 2A and 2B, respectively. The neuroregulator 104, 104' is configured to be implanted subcutaneously within the body of a patient. In embodiments, the neuroregulator 104, 104' is implanted subcutaneously on the thoracic sidewall in the area slightly anterior to the axial line and caudal to the arm pit. In other embodiments, alternative implantation locations may be determined by the implanting surgeon.

Typically, the neuroregulator 104, 104' is implanted parallel to the skin surface 103 to maximize RF coupling efficiency with the external charger 101. In an embodiment, to facilitate optimal information and power transfer between the internal coil 105, 105' of the neuroregulator 104, 104' and the external coil 102 of the external charger 101, the patient can ascertain the position of the neuroregulator 104, 104' (e.g., through palpation or with the help of a fixed marking on the skin). In an embodiment, the external charger 101 can facilitate coil positioning.

As shown in FIGS. 2A and 2B, the neuroregulator 104, 104' generally includes a housing 109, 109' overmolded with the internal coil 105, 105', respectively. The overmold 110, 110' of the neuroregulator 104, 104' is formed from a bio-compatible material that is transmissive to RF signals (i.e., or other such communication signals). Some such bio-compatible materials are well known in the art. For example, the overmold 110, 110' of the neuroregulator 104, 104' may be formed from silicone rubber or other suitable materials. The overmold 110, 110' can also include suture tabs or holes 119, 119' to facilitate placement within the patient's body.

The housing 109, 109' of the neuroregulator 104, 104' also may contain a circuit module, such as circuit 112 (see FIGS. 1, 3A, and 3B), to which the coil 105, 105' may be electrically connected along a path 105a, 105a'. The circuit module within the housing 109 may be electrically connected to a lead assembly, for example, the lead assemblies 106, 106a (FIG. 1) through first and second conductors 114, 114a. In other embodiments, a single lead may be employed. In the example shown in FIG. 2A, first and second conductors 114, 114a extend out of the housing 109, 109' through first and second strain reliefs 118, 118a. Such conductors 114, 114a are well known in the art.

The conductors 114, 114a terminate at first and second connectors 122, 122a, which are configured to receive or otherwise connect the lead assemblies 106, 106a (FIG. 1) to the conductors 114, 114a. By providing connectors 122, 122a between the neuroregulator 104 and the lead assemblies 106, 106a, the lead assemblies 106, 106a may be implanted separately from the neuroregulator 104. Also, following implantation, the lead assemblies 106, 106a may be left in place while the originally implanted neuroregulator 104 is replaced by a different neuroregulator.

As shown in FIG. 2A, the neuroregulator connectors 122, 122a can be configured to receive connectors 126 of the lead assemblies 106, 106a. For example, the connectors 122, 122a of the neuroregulator 104 may be configured to receive pin connectors (not shown) of the lead assemblies 106, 106a. In another embodiment, the connectors 122, 122a may be configured to secure to the lead assemblies 106, 106a using first and second set-screws 123, 123a, respectively, or other such fasteners. In a preferred embodiment, the connectors 122, 122a are well-known IS-1 connectors. As used herein, the term "IS-1" refers to a connector standard used by the cardiac pacing industry, and is governed by the international standard ISO 5841-3.

In the example shown in FIG. 2B, first and second female connectors 122', 122a' are configured to receive the leads 106, 106a and molded into a portion of the overmold 110' of the neuroregulator 104'. The lead connectors 126 are inserted into these molded connectors 122', 122a' and secured via first and second setscrews 123', 123a', seals (e.g., Bal Seals®), and/or another fastener.

The circuit module 112 (see FIGS. 1, 3A, and 3B) is generally configured to generate therapy signals and to transmit the therapy signals to the lead assemblies 106, 106a. The circuit module 112 also may be configured to receive power and/or data transmissions from the external charger 101 via the internal coil 105. The internal coil 105 may be configured to send the power received from the external charger 101 to the circuit module 112 for use or to the internal power source (e.g., battery) 151 of the neuroregulator 104 to recharge the power source 151.

Figure 3B:
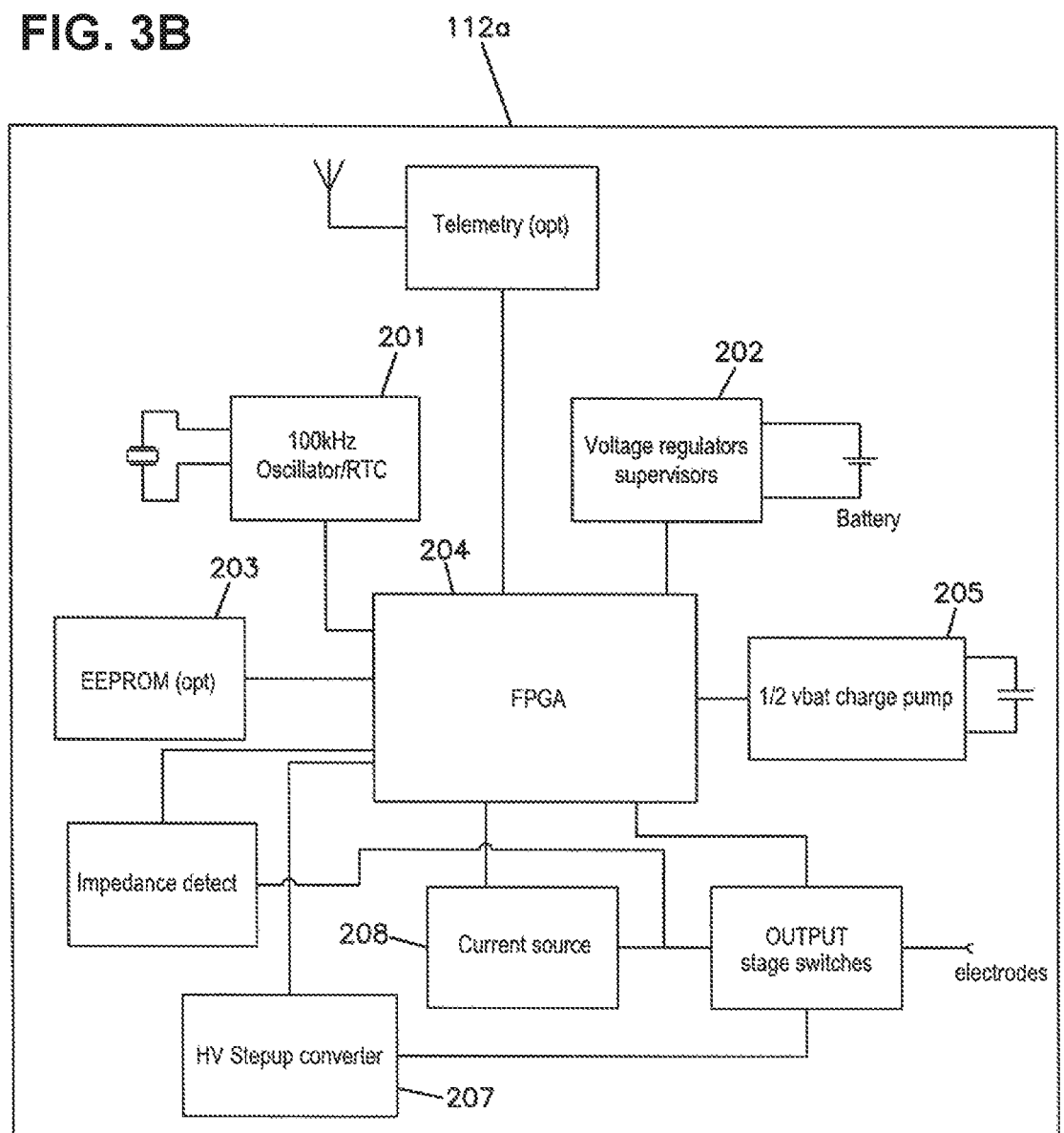
FIG. 3B is a block diagram for a low power arbitrary waveform generator intended for implantable therapeutic devices. Some of the functionality is optional such as the memory and telemetry blocks.
Figure 4:
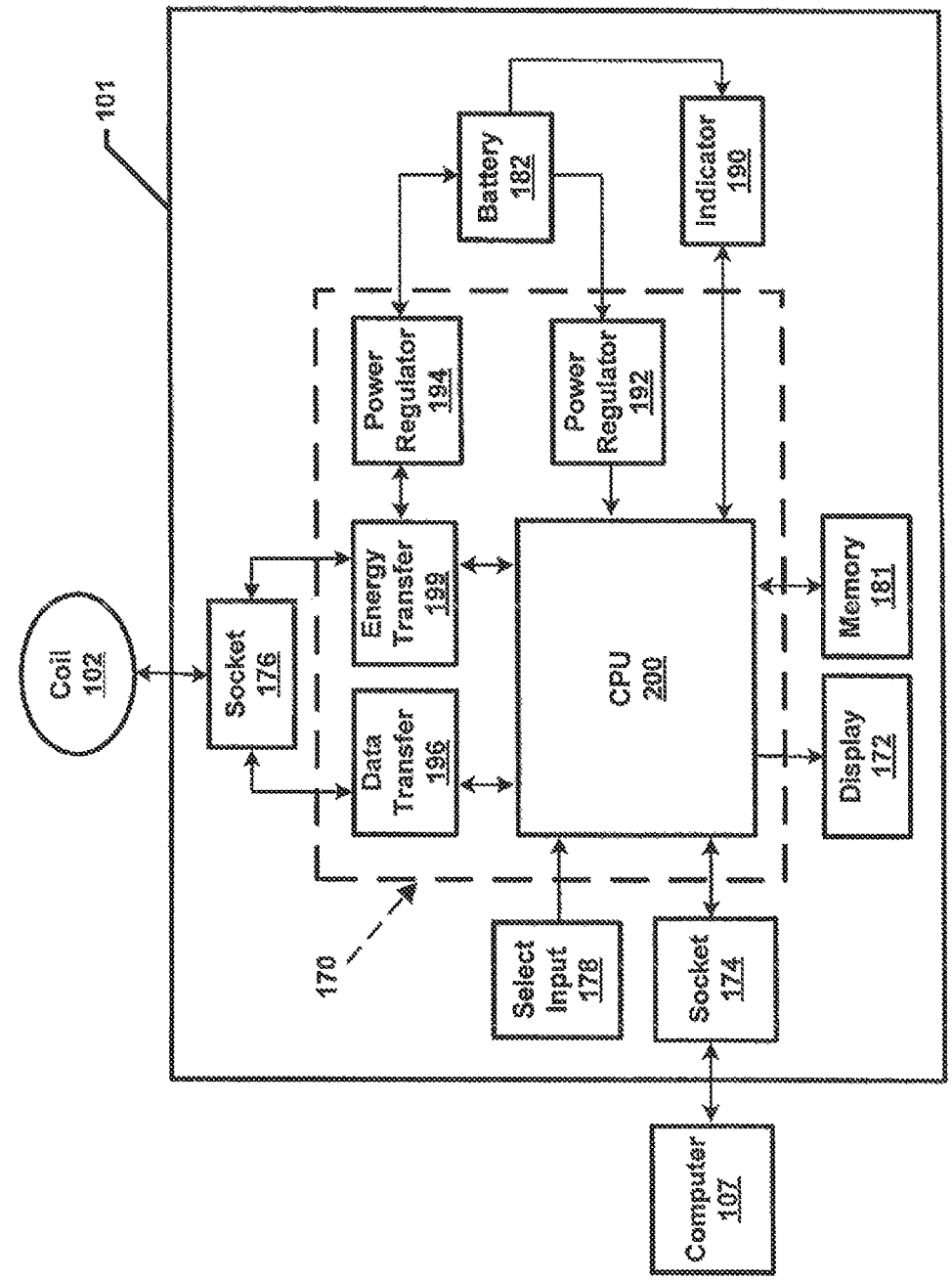
FIG. 4 is a block diagram of a circuit module for an external charger for use in the therapy system of FIG. 1 according to aspects of the present disclosure.

Block diagrams of example circuit modules 112, 112a are shown in FIGS. 3A and 3B, respectively. Either circuit module 112, 112a can be utilized with any neuroregulator, such as neuroregulators 104, 104' described above. The circuit modules 112, 112a differ in that the circuit module 112a may be operated directly from a field programmable gate array 204, without the presence of a micro controller reducing its power consumption, and the circuit module 112 does not. Power operation for circuit module 112 may be provided by the external charger 101 or by the internal power source 151. Either circuit module 112, 112a may be used with either neuroregulator 104, 104' shown in FIGS. 2A, 2B.

The circuit module 112 includes an RF input 157 including a rectifier 164. The rectifier 164 converts the RF power received from the internal coil 105 into DC electric current. Alternatively, alternating current can be used to provide a selectable but constant voltage or current. Circuitry for constant voltage or constant current devices is known to those of skill in the art.

For example, the RF input 157 may receive the RF power from the internal coil 105, rectify the RF power to DC power, and transmit the DC current to the internal power source 151 for storage. In one embodiment, the RF input 157 and the coil 105 may be tuned such that the natural frequency maximizes the power transferred from the external charger 101.

In an embodiment, the RF input 157 can first transmit the received power to a charge control module 153. The charge control module 153 receives power from the RF input 157 and delivers the power where needed through a first power regulator 156. For example, the RF input 157 may forward the power to the battery 151 for charging or to circuitry for use in creating therapy signals as will be described below. When no power is received from the coil 105, the charge control module 153 may draw power from the battery 151 and transmit the power through the second power regulator 160 for use. For example, a central processing unit (CPU) 154 of the neuroregulator 104 may manage the charge control module 153 to determine whether power obtained from the coil 105 should be used to recharge the power source 151 or whether the power should be used to produce therapy signals. The CPU 154 also may determine when the power stored in the power source 151 should be used to produce therapy signals.

The transmission of energy and data via RF/inductive coupling is known in the art. Further details describing recharging a battery via an RF/inductive coupling and controlling the proportion of energy obtained from the battery with energy obtained via inductive coupling can be found in the following references, all of which are hereby incorporated by reference herein: U.S. Pat. No. 3,727,616, issued Apr. 17, 1973, U.S. Pat. No. 4,612,934, issued Sep. 23, 1986, U.S. Pat. No. 4,793,353, issued Dec. 27, 1988, U.S. Pat. No. 5,279,292, issued Jan. 18, 1994, and U.S. Pat. No. 5,733,313, issued Mar. 31, 1998.

In general, the internal coil 105 may be configured to pass data transmissions between the external charger 101 and a telemetry module 155 of the neuroregulator 104. The telemetry module 155 generally converts the modulated signals received from the external charger 101 into data signals understandable by the CPU 154 of the neuroregulator 104. For example, the telemetry module 155 may demodulate an amplitude modulated carrier wave to obtain a data signal. In one embodiment, the signals received from the internal coil 105 are programming instructions from a physician (e.g., provided at the time of implant or on subsequent follow-up visits). The telemetry module 155 also may receive signals (e.g., patient data signals) from the CPU 154 and may send the data signals to the internal coil 105 for transmission to the external charger 101.

The CPU 154 may store operating parameters and data signals received at the neuroregulator 104 in an optional memory 152 of the neuroregulator 104. Typically, the memory 152 includes non-volatile memory. In other embodiments, the memory 152 also can store serial numbers and/or model numbers of the leads 106; serial number, model number, and/or firmware revision number of the external charger 101; and/or a serial number, model number, and/or firmware revision number of the neuroregulator 104.

The CPU 154 of the neuroregulator 104 also may receive input signals and produce output signals to control a signal generation module 159 of the neuroregulator 104. Signal generation timing may be communicated to the CPU 154 from the external charger 101 via the internal coil 105 and the telemetry module 155. In other embodiments, the signal generation timing may be provided to the CPU 154 from an oscillator module (not shown). The CPU 154 also may receive scheduling signals from a clock, such as 32 KHz real time clock (not shown).

The CPU 154 forwards the timing signals to the signal generation module 159 when therapy signals are to be produced. The CPU 154 also may forward information about the configuration of the electrode arrangement 108 to the signal generation module 159. For example, the CPU 154 can forward information obtained from the external charger 101 via the internal coil 105 and the telemetry module 155.

The signal generation module 159 provides control signals to an output module 161 to produce therapy signals. In an embodiment, the control signals are based at least in part on the timing signals received from the CPU 154. The control signals also can be based on the electrode configuration information received from the CPU 154.

The output module 161 produces the therapy signals based on the control signals received from the signal generation module 159. In an embodiment, the output module 161 produces the therapy signals by amplifying the control signals. The output module 161 then forwards the therapy signals to the lead arrangement 108.

In an embodiment, the signal generation module 159 receives power via a first power regulator 156. The power regulator 156 regulates the voltage of the power to a predetermined voltage appropriate for driving the signal generation module 159. For example, the power regulator 156 can regulate the voltage in a range of 1-20 volts.

In an embodiment, the output module 161 receives power via a second power regulator 160. The second power regulator 160 may regulate the voltage of the power in response to instructions from the CPU 154 to achieve specified constant voltage levels. The second power regulator 160 also may provide the voltage necessary to deliver constant current to the output module 161.

The output module 161 can measure the voltage of the therapy signals being outputted to the lead arrangement 108 and report the measured voltage to the CPU 154. A capacitive divider 162 may be provided to scale the voltage measurement to a level compatible with the CPU 154. In another embodiment, the output module 161 can measure the impedance of the lead arrangement 108 to determine whether the leads 106, 106a are in contact with tissue. This impedance measurement also may be reported to the CPU 154.

Another embodiment of a circuit is shown in FIG. 3B. The therapy algorithm is divided into a number of very small time segments and the corresponding voltage or current value of that therapy waveform segment is stored into a Field Programmable Gate Array 204. The therapy algorithm voltage or current values may be absolute values or changes relative to the previous voltage or current values. There is an option to retrieve alternate waveforms from an EEPROM 203. The clock oscillator 201 determines the time between successive therapy waveform segments and provides various clock signals for other circuits. The charge pump 205 provides the necessary voltage levels from the battery voltage for operating the circuits, the High Voltage (HV) generator 207 and a current source 208 provide the applicable voltage and current levels for the therapy waveform which may be programmable by the user. Various voltage monitors 202, regulators (not shown) and impedance detectors 206 measure and control the correct operation of the circuits. Some of the functionality is optional such as the memory 203 and telemetry blocks 155.

In addition, the power consumption needs of the neuroregulator 104, 104' can change over time due to differences in activity. For example, the neuroregulator 104, 104' will require less power to transmit data to the external charger 101 or to generate therapy signals than it will need to recharge the internal battery 151.

b. Electrodes

Multipolar Electrodes

In embodiments, the disclosure provides a multipolar electrode assembly. Multipolar electrodes include, for example, a bipolar, a tripolar, a quadruple polar, and five polar electrode. One of the advantages of using multipolar electrodes is that rapid firing of action potentials at the beginning of HFAC may be reduced and sustained firing of action potentials during a prolonged application of HFAC may be minimized, resulting in a more effective block. A multipolar electrode has many advantages in terms of flexibility in procedures involving neuromodulation therapies.

Tripolar Electrodes

In the case of using tripolar electrodes to deliver a high frequency alternating current (HFAC) neuronal conduction block, the outer two electrodes can have the same polarity, with the middle electrode having the opposite polarity of the outer two electrodes (tripolar configuration).

As an example of a tripolar electrode assembly, it may be desirable for only two of the electrodes to deliver HFAC and the third to act as a ground. In embodiments, the two electrodes delivering HFAC can either be adjacent (i.e., next to each other) or the outer two electrodes. In embodiments, if another electrode or electrode assembly is placed on another branch of a nerve, another nerve or anatomical feature, the device could be configured to send current from one of the electrode assemblies to the other in a monopolar configuration. A monopolar configuration could also be achieved by sending current from one, or both, of the electrode assemblies to the pulse generator at the same or different times.

In another embodiment using a tripolar electrode assembly, the electrodes could also be configured to stimulate. In embodiments, configurations of one polarity on the outer two electrodes and the opposite polarity on the middle electrode could be applied. Another configuration could include a bipolar configuration between two adjacent electrodes or a bipolar configuration between the outer two electrodes. The third electrode not delivering current could be grounded to the pulse generator.

An alternative embodiment of a tripolar electrode assembly could be configured to have the current flowing out of the electrodes to produce conduction block and directional stimulation. The inner and one of the outer electrodes could deliver HFAC while the other outer electrode is delivering stimulation. In one stimulation configuration, one pole would be the outer electrode and the other pole the pulse generator. If another electrode or electrode assembly is on another branch of a nerve, another nerve or anatomical feature, the opposite pole could be one or multiple electrodes in the other assembly. The assembly on another branch of a nerve, another nerve or anatomical feature could also be configured to be in a block and directional stimulation mode during the same time as the other assembly is doing the equivalent or is quiescent.

In the block and directional stimulation configuration, either afferent nerve fibers (axons that send information toward central nervous system) or efferent nerve fibers (axons that send information in a peripheral direction from the central nervous system) could be activated. If two tripolar electrode assemblies are on two different branches of a nerve, another nerve or anatomical feature, then they could independently (or concurrently) be in any of the above configurations which allows for a sink to a current source.

If two tripolar electrode assemblies are on two different branches of a nerve, another nerve or anatomical feature, then any of the above configurations could be applied with different temporal patterns. Examples include, but not limited to, blocking a first nerve and stimulating a second and then switching to stimulating the first nerve and blocking the second. Blocking one nerve and stimulating a second followed by blocking both nerves or vice versa. Blocking both nerves followed by stimulating both nerves or vice versa. Using directional block and stimulation on a nerve and then switching the direction of the stimulation and block. Using directional block and stimulation on two nerves and then switching the direction of the stimulation and block on one or both of the nerves.

Five Polar Electrodes

A 5 polar electrode would be beneficial for various types of neuromodulation. In terms of HFAC conduction block a 5 polar electrode may help decrease onset responses or repetitive firing during long durations of HFAC. One configuration to do this would be the middle and outer two electrodes having the same polarity and the other two electrodes having the opposite polarity. In another configuration the outer two electrodes would be grounded to the pulse generator, the middle electrode with one polarity and the adjacent electrodes to the middle having the opposite polarity. In another configuration, one of the outer electrodes and its adjacent electrode would be grounded to the pulse generator and the other three electrodes delivering HFAC in a tripolar configuration. Another grounding method would be to have an outer electrode and its adjacent electrode blocking in a bipolar configuration while the other three are grounded to the pulse generator. The 5 polar electrode assembly could also block in a monopolar configuration with one or multiple electrodes sending current to the pulse generator.

A 5 polar electrode assembly can also be configured to stimulate. One configuration to do this would be the middle and outer two electrodes having the same polarity and the other two the opposite polarity. In another configuration the outer two electrodes would be grounded to the pulse generator, the middle electrode with one polarity and the adjacent electrodes to the middle having the opposite polarity. In another configuration one of the outer electrodes and its adjacent electrode would be grounded to the pulse generator and the other three electrodes stimulating in a tripolar configuration. Another grounding method would be to have an outer electrode and its adjacent electrode stimulating in a bipolar configuration while the other three are grounded to the pulse generator. The 5 polar electrode assembly could also stimulate in a monopolar configuration with one or multiple electrodes sending current to the pulse generator.

Directional block and stimulation could also be accomplished with a 5 polar electrode assembly. An outer and its adjacent electrode could be delivering stimulation in a bipolar configuration while the other three are delivering high HFAC conduction block in a tripolar configuration. Likewise, an outer and its adjacent electrode could be delivering HFAC conduction block in a bipolar configuration while the other three are delivering stimulation in a tripolar configuration. An outer and its adjacent electrode could be delivering stimulation in a bipolar configuration while two out of the other three are delivering HFAC conduction block in a bipolar configuration while the other electrode (either the one next to the blocking electrodes or one next to the stimulation electrodes) is grounded to the pulse generator. In the block and directional stimulation configuration, either afferent nerve fibers (axons that send information toward central nervous system) or efferent nerve fibers (axons that send information in a peripheral direction from the central nervous system) could be activated.

If two 5 polar electrode assemblies are on two different branches of a nerve, another nerve or anatomical feature, a monopolar configuration could be achieved for stimulation or HFAC conduction block by sending current from one, or both, of the electrode assemblies to the pulse generator at the same or different times. A monopolar configuration could also be achieved by sending current from one, or more than one electrode of one assembly to one, or more than one electrode of the other assembly.

If two 5 polar electrode assemblies are on two different branches of a nerve, another nerve or anatomical feature, then they could independently (or concurrently) be in any of the above configurations which allows for a sink to a current source.

If two 5 polar electrode assemblies are on two different branches of a nerve, another nerve or anatomical feature, then any of the above configurations could be applied with different temporal patterns. Examples include, but not limited to, blocking a first nerve and stimulating a second and then switching to stimulating the first nerve and blocking the second. Blocking one nerve and stimulating a second followed by blocking both nerves or vice versa. Blocking both nerves followed by stimulating both nerves or vice versa. Using directional block and stimulation on a nerve and then switching the direction of the stimulation and block. Using directional block and stimulation on two nerves and then switching the direction of the stimulation and block on one or both of the nerves.

When low duty cycle electrical signal algorithms are applied, energy savings can be improved by also increasing impedance of the electrodes. Increasing impedance of the electrodes can be accomplished by varying electrode size and/or by coating electrodes with a coating having a resistivity that is at least $10^2 \times cm^2$. For example, a 2500 Hz 90 microsecond algorithm is considered a low duty cycle (LDC) algorithm whereas a 5000 Hz 90 microsecond algorithm is considered a high duty cycle (HDC) algorithm. Note that the amount of current required to produce a 50% block is similar for the LDC and HDC algorithms with the high impedance range (at least 6000 Ohms). With a lower impedance range (3000-6000 Ohms) it takes more current to block 50% of the nerve with the LDC algorithm as with the HDC algorithm.

In other embodiments, the electrode size is such that the impedance between the tissue and the electrode is at least 2000 Ohms. In some embodiments, the electrode has a size of less than about 10 mm$^2$. Decreasing electrode size provides a higher impedance and lower energy requirements. Increasing impedance can improve the blocking effectiveness of a low duty cycle algorithm compared to a high duty cycle algorithm by shifting the current effect relationship curve (of blocking) for a low duty cycle algorithm closer to that of a high duty cycle algorithm (figure z). High impedance electrodes sizes, for example, can range from 0.1 to 9.99 mm$^2$. Electrodes having an impedance of at least 2000 Ohms can be employed in any of the multipolar configurations described herein. Smaller size electrodes may also decrease prolonged repetitive firing during HFAC.

In other embodiments, the impedance of the electrode is increased through the use of a coating that has a resistivity of at least $10^2$ ohms per cm$^2$. Such coatings include Teflon, silicon, polyethylene, paralene as described in US20140214129, which is hereby incorporated by reference.

2. Electrical Signal Parameters

This disclosure describes systems and methods of providing electrical signal therapy for downregulating and/or upregulating nerve activity in a subject. The systems and methods provide for layered patterns of electrical signal including microsecond inactive phases, millisecond inactive phases, and/or off times in order to vary how and when charge is applied to the nerve, and to save energy.

In embodiments, a system and method comprises more than one microsecond cycle, each microsecond cycle comprising more than one period, each period comprising a charge and recharge phase and optionally, a pulse delay, each period having a frequency of at least 1000 Hz; and a microsecond inactive phase.

In other embodiments, a system and method comprises delivering more than one microsecond cycle to form a millisecond cycle, each millisecond cycle separated by a millisecond inactive phase. The length of time of the microsecond and/or millisecond inactive phases provides for the ability to vary how often electrical signal treatment is applied to the nerve during an on time and allows for energy savings as compared to electrical signal therapy not having inactive phases.

In embodiments, a system and method of applying an electrical signal having parameters that downregulate and/or upregulate nerve activity to a nerve in a subject comprises: applying the electrical signal to the nerve during an on time, wherein the electrical signal comprises more than one microsecond cycle comprising more than one period, each period comprising a charge recharge phase which may or may not have pulse delays, each period having a frequency of at least 1000 Hz; and a microsecond inactive phase. In embodiments, a microsecond cycle has a period comprising a charge and recharge phase, and optionally, includes one or more pulse delays. The period of a charge recharge phase is based on the frequency selected and the presence of pulse delays. For example, a charge recharge phase having a frequency of 5000 Hz without any pulse delay would have a period of at 200 microseconds based on 1 divided by the frequency. In other cases, the period of each charge and recharge phase for a frequency of 5000 Hz is 200 microseconds including a first pulse delay of 10 microseconds and a second pulse delay of 10 microseconds and a charge phase of 90 microseconds and recharge phase of 90 microseconds.

Figure 7:
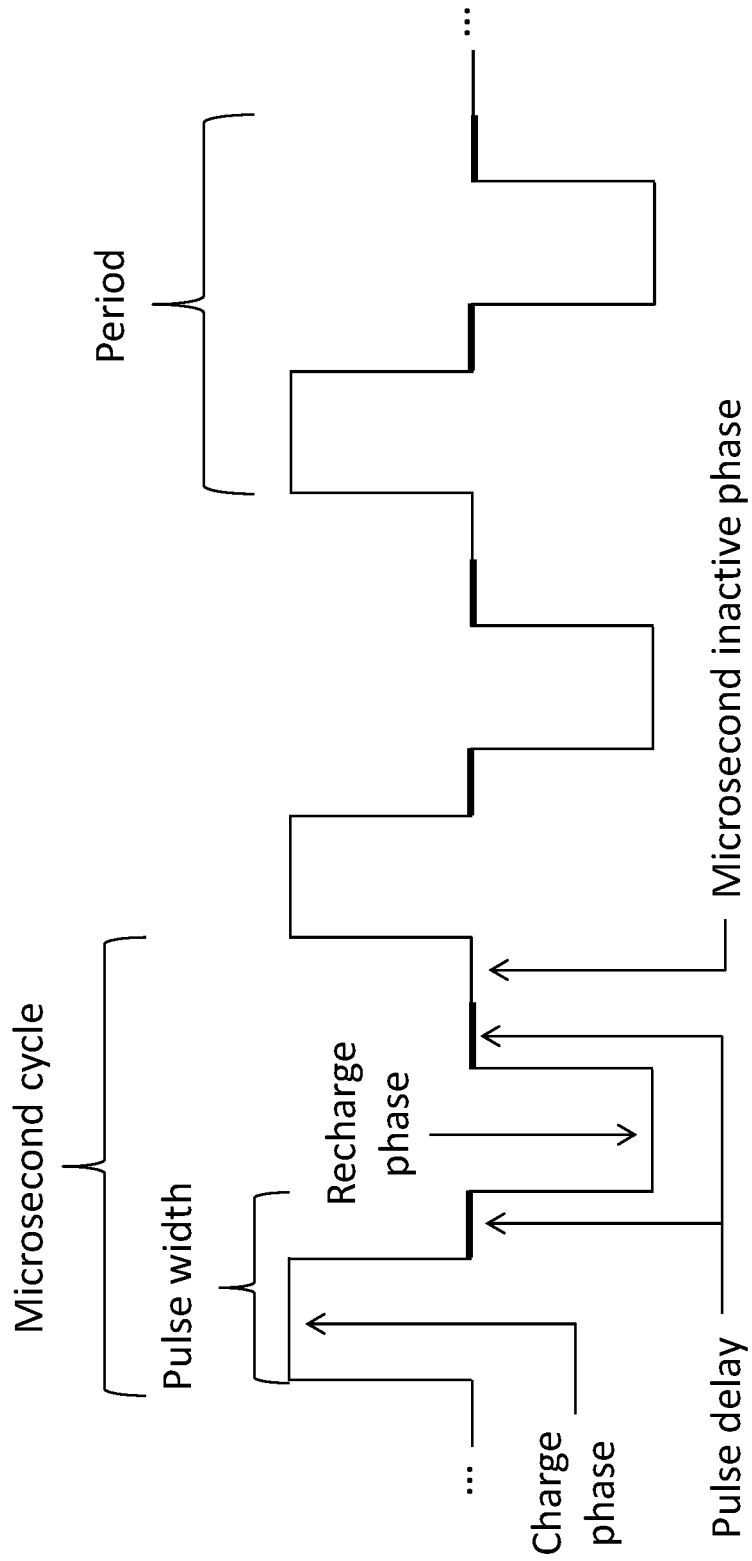
FIG. 7 is a representation of a pattern of electrical signals displaying a low duty cycle HFAC/HFAV which contains microsecond cycles. Within the microsecond cycles are charge and recharge phases separated by pulse delays and microsecond inactive phases following the pulse delay that follows the recharge phase. The charge recharge phase and the pulse delays form a period. The pulse delay between the charge and recharge phase is equal in time to the pulse delay following the recharge phase.

In some embodiments, a first pulse delay occurs after the charge phase and/or a second pulse delay occurs after the recharge phase. In embodiments, the first and second pulse delays are the same length. In embodiments, the length of the first and/or second pulse delay is selected to allow for a charge balanced alternating current signal to be delivered to the nerve. In embodiments, a pulse delay is about 30 microseconds or less. An exemplary embodiment is shown in FIG. 7. FIG. 7 shows three microsecond cycles, each microsecond cycle comprises a period comprising a charge phase followed by a pulse delay, a recharge phase and a pulse delay; and a microsecond inactive phase.

In embodiments, the electrical signal has a frequency in each period of a microsecond cycle of at least 200 Hz, at least 250 Hz, at least 300 Hz, at least 400 Hz, at least 500 Hz, at least 1000 Hz, at least 2000 Hz, at least 3000 Hz, at least 4000 Hz, or at least 5000 Hz or more. In other embodiments, the frequencies range from about 200 Hz to 25 kHz, 200 Hz to 20 kHz, 200 Hz to 15 kHz, 200 Hz to 10 kHz, 200 to 5 kHz, 200 to 2.5 kHz, 200 to 1 kHz, or 200 to 500 Hz. In other embodiments, the frequencies range from about 1000 Hz to 25 kHz, 1000 Hz to 20 kHz, 1000 Hz to 15 kHz, 1000 Hz to 10 kHz, 1000 to 5 kHz, or 1000 Hz to 2.5 kHz. In other embodiments, the frequencies range from about 1000 Hz to 10 kHz, 1000 Hz to 9000 Hz, 1000 Hz to 8000 Hz, 1000 Hz to 7000 Hz, 1000 to 6000 Hz, 1000 Hz to 5000 Hz, 1000 Hz to 4000 Hz, 1000 Hz to 3000 Hz, or 1000 Hz to 2000 Hz. In embodiments, electrical signals at such frequencies can downregulate nerve activity.

In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

In embodiments, the amplitude of the signal is at least 1 mAmp. In other embodiments, the amplitude ranges from about 0.1 to 20 mAmps, 0.1 to 15 mAmps, 0.1 to 10 mAmps, 0.1 to 8 mAmps, or 0.1 to 5 mAmps.

In embodiments, the amplitude is at least 1 volt. In other embodiments, the amplitude ranges from about 1 to 20 volts, 1 to 15 volts, 1 to 10 volts, 1 to 8 volts, or 1 to 5 volts.

In embodiments, the on time is at least about 30 seconds. In other embodiments, the on time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include on times of varying amounts. For example, a therapy cycle can include 1 minutes of on time, 1 minute of off time, 2 minutes of on time, followed by 5 minutes of off time.

In embodiments, the off time is selected in order to allow at least partial recovery of the nerve. In embodiments, the off time may be minimized due to the presence of microsecond inactive phases and/or millisecond inactive phases. In embodiments, off times are at least about 30 seconds. In other embodiments, the off time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include off times of varying amounts. For example, a therapy cycle can include 1 minute of on time, 1 minute of off time, 2 minutes of on time, followed by 5 minutes of off time.

In embodiments, the microsecond cycle comprises more than one period which comprises a charge recharge phase and may or may not contain pulse delays; and a microsecond inactive phase. In some embodiments, the inactive phase is longer than the period. In embodiments, the length of the inactive phase can vary between each period.

In embodiments, the period is about 1000 microseconds or less, about 500 microseconds or less, or about 200 microseconds or less.

In embodiments, the microsecond inactive phase is in a ratio to the charge recharge phase of about 10 to 1, 8 to 1, 6 to 1, 4 to 1, or 2 to 1. In embodiments, the microsecond inactive phase is at least about 80 microseconds. In embodiments, the microsecond inactive phase is at least 80 microseconds up to 10,000 microseconds, 200 microseconds up to 10,000 microseconds, or 400 microseconds up to 10,000 microseconds. In embodiments, the microsecond inactive phase is about 10 microseconds to 10,000 microseconds. In embodiments, a microsecond inactive phase is 10,000 microseconds or less, 1000 microseconds or less, or 500 microseconds or less. In embodiments, the microsecond inactive phase is at least 20 microseconds up to 10,000 microseconds, 20 microseconds up to 5000 microseconds, 20 microseconds up to 1000 microseconds, 20 microseconds up to 500 microseconds, or 20 microseconds up to 100 microseconds.

In embodiments, the frequency is at least 1000 Hz, 2000 Hz, 3000 Hz, 4000 Hz, 5000 Hz, 6000 Hz, 7000 Hz, 8000 Hz, 9000 Hz, or 10,000 Hz or more.

In embodiments, multiple periods can be administered in a single microsecond cycle. In other embodiments, the application of the electrical signal includes multiple microsecond cycles.

Figure 5:
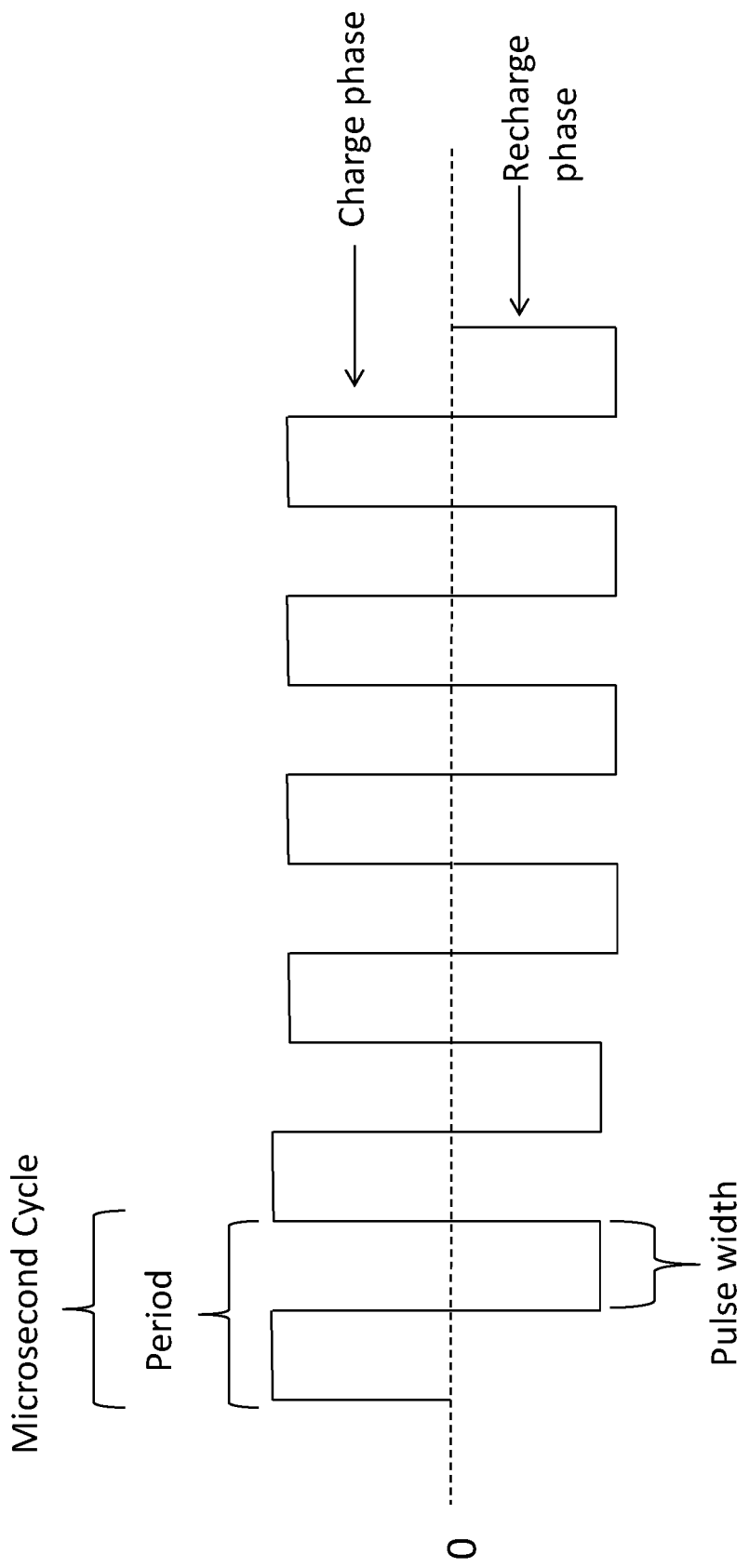
FIG. 5 is a representation of a prior art waveform displaying a high duty cycle HFAC/HFAV signal. In this example the period is 5 milliseconds or less making the frequency 200 Hz or greater which is considered a high frequency signal.
Figure 6:
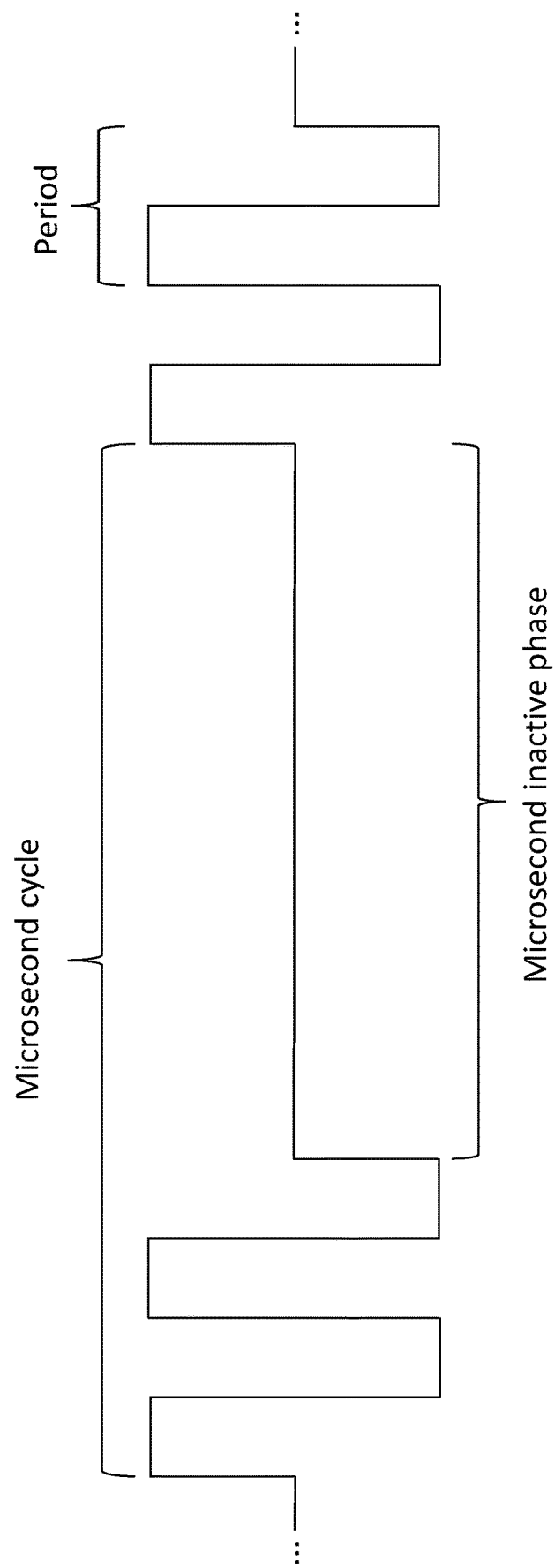
FIG. 6 is a representation of a pattern of electrical signals displaying a repetitive low duty cycle HFAC/HFAV on the microsecond scale wherein the charge/recharge phases are followed by a substantially longer microsecond inactive phase to form a microsecond cycle. The microsecond cycle includes more than one period. This pattern repeats itself for the duration of an on time.

An exemplary embodiment is shown in FIG. 6. In FIG. 6, 2 microsecond cycles are shown. The first microsecond cycle comprises 2 periods, and a microsecond inactive phase. Each charge recharge phase in the microsecond cycle has a period equal to 1 divided by the frequency without any pulse delays. Energy savings are realized by including microsecond inactive phases between the periods as can be seen by comparison with FIG. 5. In FIG. 5, the standard HFAC therapy involves application of charge recharge phases during an on time without any microsecond inactive phases. In addition, the length of the microsecond inactive phases and/or the number of periods in a microsecond cycle can be varied to provide application of a total amount of charge during an on time while varying the impact on the nerve.

In other embodiments, a system and method of applying an electrical signal having parameters that downregulate and/or upregulate nerve activity to a nerve in a subject comprises: applying the electrical signal to the nerve during an on time, wherein the electrical signal comprises more than one microsecond cycle to form a millisecond active phase, and applying more than one millisecond active phase during the on time, wherein each millisecond active phase is separated by a millisecond inactive phase during the on time.

In embodiments, the electrical signal has a frequency of a period in a microsecond cycle. In embodiments, a period has a frequency of at least 200 Hz, at least 250 Hz, at least 300 Hz, at least 400 Hz, at least 500 Hz, at least 1000 Hz, at least 2000 Hz, at least 3000 Hz, at least 4000 Hz, or at least 5000 Hz. In other embodiments, the frequencies range from about 200 Hz to 25 kHz, 200 Hz to 20 kHz, 200 Hz to 15 kHz, 200 Hz to 10 kHz, 200 to 5 kHz, 200 to 2.5 kHz, 200 to 1 kHz, or 200 to 500 Hz. In other embodiments, the frequencies range from about 1000 Hz to 25 kHz, 1000 Hz to 20 kHz, 1000 Hz to 15 kHz, 1000 Hz to 10 kHz, 1000 to 5 kHz, or 1000 Hz to 2.5 kHz. In other embodiments, the frequencies range from about 1000 Hz to 10 kHz, 1000 Hz to 9000 Hz, 1000 Hz to 8000 Hz, 1000 Hz to 7000 Hz, 1000 to 6000 Hz, 1000 Hz to 5000 Hz, 1000 Hz to 4000 Hz, 1000 Hz to 3000 Hz, or 1000 Hz to 2000 Hz. In embodiments, electrical signals at such frequencies can downregulate nerve activity.

In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

In embodiments, the amplitude of the signal is at least 1 mAmp. In other embodiments, the amplitude ranges from about 1 to 20 mAmps, 1 to 15 mAmps, 1 to 10 mAmps, 1 to 8 mAmps, or 1 to 5 mAmps.

In embodiments, the amplitude is at least 1 volt. In other embodiments, the amplitude ranges from about 1 to 20 volts, 1 to 15 volts, 1 to 10 volts, 1 to 8 volts, or 1 to 5 volts.

In embodiments, the on time is at least about 30 seconds. In other embodiments, the on time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include on times of varying amounts. For example, a therapy cycle can include 1 minutes of on time, 1 minute of off time, 2 minutes of on time, followed by 5 minutes of off time.

In embodiments, the off time is selected in order to allow at least partial recovery of the nerve. In embodiments, the off time may be minimized due to the presence of microsecond inactive phases and/or millisecond inactive phases. In embodiments, off times are at least about 30 seconds. In other embodiments, the off time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include off times of varying amounts. For example, a therapy cycle can include 1 minutes of on time, 1 minute of off time, 2 minutes of on time, followed by 5 minutes of off time.

In embodiments, a microsecond cycle has a period comprising a charge and recharge phase, and optionally, includes one or more pulse delays. The time of a period includes the time of a charge recharge phases and the presence or absence of pulse delays. For example, a period with a single charge recharge phase without any pulse delays and having a frequency of 5000 Hz has a period of 200 microseconds based on 1 divided by the frequency. In other cases, the period of each charge and recharge phase for a frequency of 5000 Hz is 200 microseconds including a 90 microsecond charge phase followed by a first 10 microsecond pulse delay, followed by a 90 microsecond discharge phase and a second pulse delay of 10 microseconds.

Figure 9:
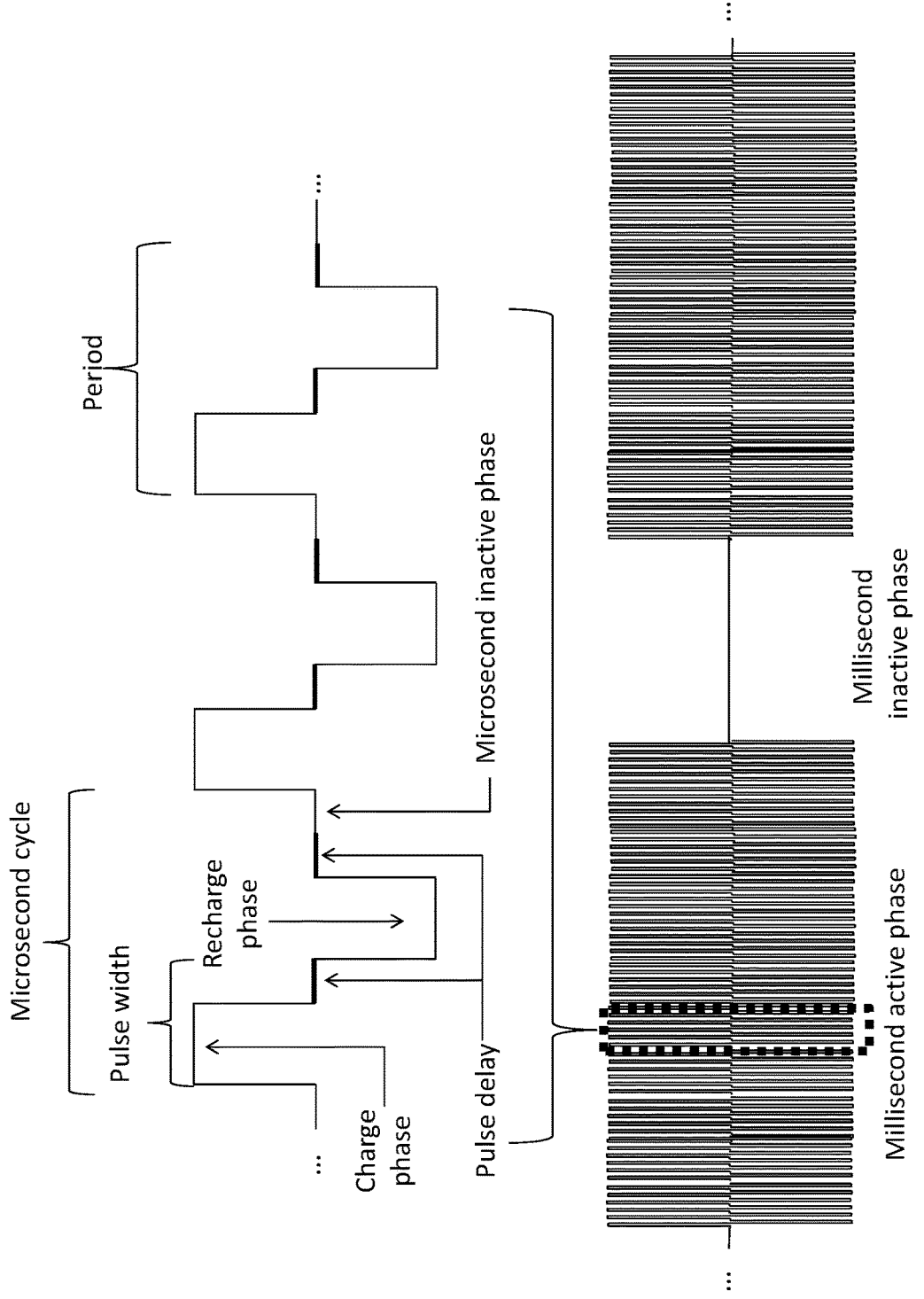
FIG. 9 is a representation of a pattern of layered electrical signals displaying a low duty cycle HFAC/HFAV which contains repetitive microsecond cycles which form a millisecond active phase. Within the microsecond cycles are charge and recharge phases separated by pulse delays and microsecond inactive phases following the pulse delay that follows the recharge phase. The pulse delay between the charge and recharge phase is equal in time to the pulse delay following the recharge phase.

In some embodiments, a first pulse delay occurs after the charge phase and/or a second pulse delay occurs after the recharge phase. In embodiments, the first and second pulse delays are the same length. In embodiments, the length of the first and/or second pulse delay is selected to allow for a charge balanced alternating current signal to be delivered to the nerve and without sending unwanted signals. In embodiments, a pulse delay is about 30 microseconds or less. An exemplary embodiment is shown in FIG. 9. FIG. 9 shows three microsecond cycles, each microsecond cycle comprises a charge phase followed by a pulse delay, a recharge phase and a pulse delay; and a microsecond inactive phase. Multiple microsecond cycles form a millisecond active phase.

In embodiments, a millisecond active phase is separated from another millisecond active phase by a millisecond inactive phase. In embodiments, the millisecond inactive phase is longer than the millisecond active phase. In embodiments, the millisecond inactive phase can vary in time between each millisecond active phase.

In embodiments, the millisecond active phase is at least 0.16 millisecond. In embodiments, the millisecond active phase is 0.16 millisecond to 1,100 milliseconds, 0.16 millisecond to 900 milliseconds, 0.16 millisecond to 800 milliseconds, 0.16 millisecond to 700 milliseconds, 0.16 millisecond to 600 milliseconds, 0.16 millisecond to 500 milliseconds, 0.16 to 400 milliseconds, 0.16 to 300 milliseconds, 0.16 to 200 milliseconds, 0.16 to 100 milliseconds, 0.16 to 50 milliseconds, 0.16 to 40 milliseconds, 0.16 to 30 milliseconds, 0.16 to 20 milliseconds, 0.16 to 10 milliseconds, or 0.16 to 5 milliseconds. In embodiments, the millisecond active phase is at least 1 millisecond. In other embodiments, the millisecond active phase is 1 to 1,100 milliseconds, 1 millisecond to 900 milliseconds, 1 millisecond to 800 milliseconds, 1 millisecond to 700 milliseconds, 1 millisecond to 600 milliseconds, 1 millisecond to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, 1 to 10 milliseconds, or 1 to 5 milliseconds.

In embodiments, the millisecond active phase comprises at least 2 to 100 microsecond cycles, at least 2 to 90, at least 2 to 80, at least 2 to 70, at least 2 to 60, at least 2 to 50, at least 2 to 40, at least 2 to 30, at least 2 to 20, at least 2 to 10, at least 2 to 5, or at least 2 to 4 microsecond cycles.

In embodiments, the millisecond inactive phase is in a ratio to the millisecond active phase of about 10 to 1, 8 to 1, 6 to 1, 4 to 1, 2 to 1 or 1 to 2. In embodiments, the millisecond inactive phase is at least 0.08 milliseconds. In embodiments, the millisecond inactive phase is 0.08 millisecond to 11,000 milliseconds, 0.08 millisecond to 9000 milliseconds, 0.08 millisecond to 8000 milliseconds, 0.08 millisecond to 7000 milliseconds, 0.08 millisecond to 6000 milliseconds, 0.08 millisecond to 5000 milliseconds, 0.08 to 4000 milliseconds, 0.08 to 3000 milliseconds, 0.08 to 2000 milliseconds, 0.08 to 1000 milliseconds, 0.08 to 500 milliseconds, 0.08 to 400 milliseconds, 0.08 to 300 milliseconds, 0.08 to 200 milliseconds, 0.08 to 100 milliseconds, 0.08 to 50 milliseconds, 0.08 to 40 milliseconds, 0.08 to 30 milliseconds, 0.08 to 20 milliseconds, or 0.08 to 10 milliseconds. In embodiments, the millisecond inactive phase is 1 millisecond to 11,000 milliseconds, 1 millisecond to 9000 milliseconds, 1 millisecond to 8000 milliseconds, 1 millisecond to 7000 milliseconds, 1 millisecond to 6000 milliseconds, 1 millisecond to 5000 milliseconds, 1 to 4000 milliseconds, 1 to 3000 milliseconds, 1 to 2000 milliseconds, 1 to 1000 milliseconds, 1 to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, or 1 to 10 milliseconds.

Figure 8:
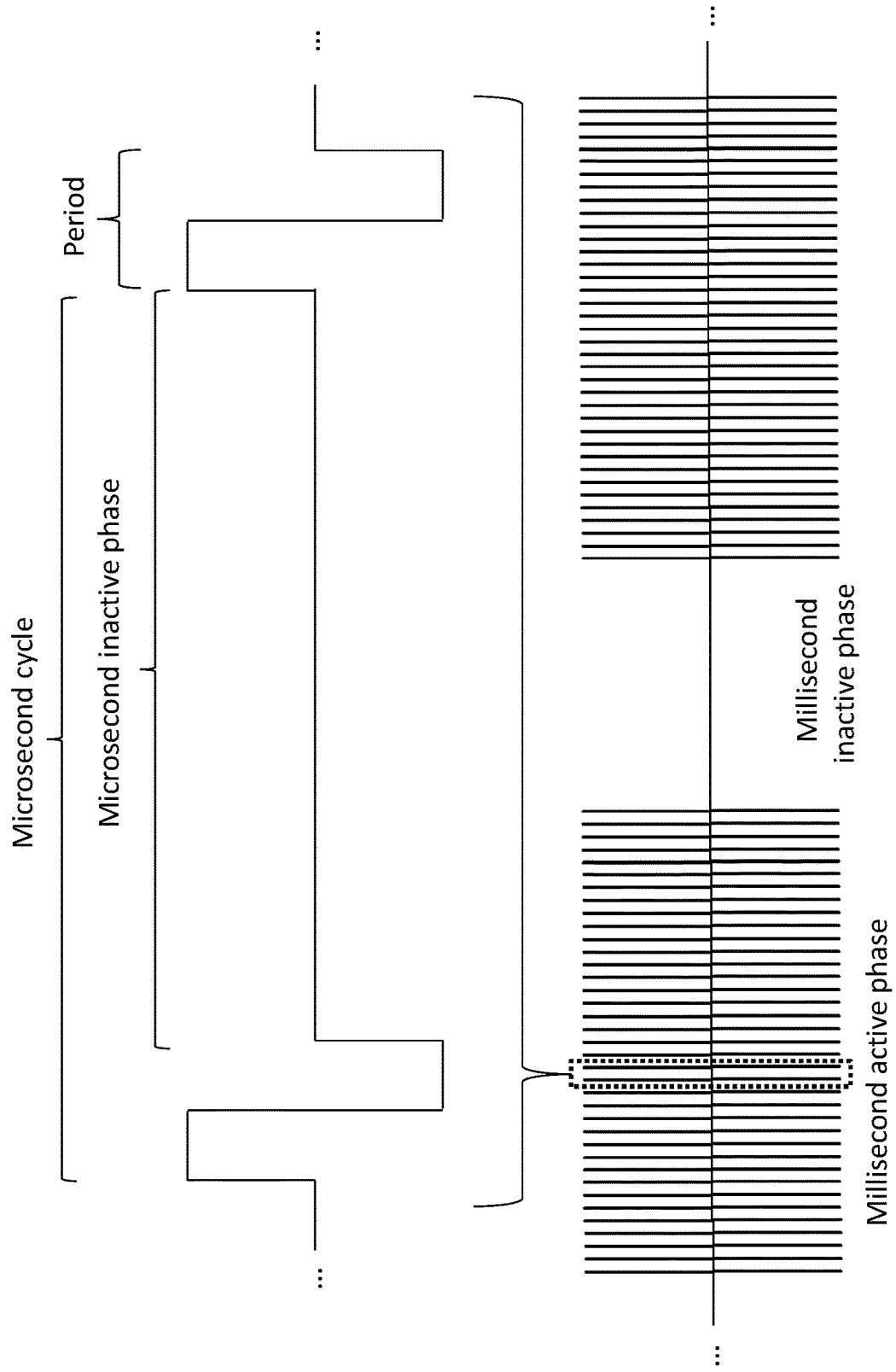
FIG. 8 is a representation of a layered pattern of electrical signals displaying a low duty cycle HFAC/HFAV algorithm which contains microsecond cycles, with long microsecond inactive phases, which are repeated to form a millisecond active phase which is followed by a millisecond inactive phase. This pattern repeats itself for the duration of an on time.

An exemplary embodiment is shown in FIG. 8. As shown in FIG. 8, a microsecond cycle comprises at least one period; and a microsecond inactive phase. The millisecond cycle comprises a millisecond active phase that includes more than one microsecond cycles and a millisecond inactive phase. Energy savings are realized by including microsecond inactive phases between the charge recharge phases as well as between millisecond inactive phases between millisecond active phases. In addition, the length of the microsecond inactive phases, millisecond inactive phases and/or the number of periods can be varied to provide application of a total amount of charge during an on time while varying the impact on the nerve. In embodiments, the frequency of the electrical signal treatment is selected to downregulate activity on the nerve and is at least 200 Hz, 300 Hz, 400 Hz, 500 Hz, 600 Hz, 700 Hz, 800 Hz, 900 Hz, 1000 Hz or more.

In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

In yet other embodiments, a system and method of applying an electrical signal having parameters to downregulate and/or upregulate nerve activity to a nerve in a subject comprises: applying the electrical signal to the nerve during an on time, wherein the electrical signal comprises a first pattern and a second pattern which differ from one another. In embodiments, the first pattern comprises at least one microsecond cycle. In other embodiments, the first pattern comprises more than one millisecond active phase, wherein each millisecond active phase comprises more than one microsecond cycle, and each millisecond active phase is separated by a millisecond inactive phase. In embodiments, the second pattern comprises at least one microsecond cycle.

In embodiments, the second pattern comprises more than one millisecond active phase, wherein each millisecond active phase comprises more than one microsecond cycle, and each millisecond active phase is separated by a millisecond inactive phase.

In yet other embodiments, a system and method of applying an electrical signal having parameters to downregulate and/or upregulate nerve activity to a nerve in a subject comprises: applying the electrical signal to the nerve during an on time, wherein the electrical signal comprises a first pattern comprising at least one microsecond cycle; and a second pattern comprising more than one millisecond active phase, wherein each millisecond active phase comprises more than one microsecond cycle, and each millisecond active phase is separated by a millisecond inactive phase, wherein the first and second patterns have a different amplitude and/or different on times. In embodiments, the microsecond cycle comprises at least one period comprising a charge recharge phase and optionally, a pulse delay, wherein each period has a frequency of at least 200 Hz; and a microsecond inactive phase.

In embodiments, the electrical signal has a frequency of a period which comprises a charge recharge phase and may have pulse delays, wherein the frequency is at least 200 Hz, at least 250 Hz, at least 300 Hz, at least 400 Hz, at least 500 Hz, at least 1000 Hz, at least 2000 Hz, at least 3000 Hz, at least 4000 Hz, or at least 5000 Hz. In other embodiments, the frequencies range from about 200 Hz to 25 kHz, 200 Hz to 20 kHz, 200 Hz to 15 kHz, 200 Hz to 10 kHz, 200 to 5 kHz, 200 to 2.5 kHz, 200 to 1 kHz, or 200 to 500 Hz. In other embodiments, the frequencies range from about 1000 Hz to 25 kHz, 1000 Hz to 20 kHz, 1000 Hz to 15 kHz, 1000 Hz to 10 kHz, 1000 to 5 kHz, or 1000 Hz to 2.5 kHz. In embodiments, electrical signals at such frequencies can downregulate nerve activity.

In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

In embodiments, the amplitude of the signal is at least 1 mAmp. In other embodiments, amplitudes ranges from about 1 to 20 mAmps, 1 to 15 mAmps, 1 to 10 mAmps, 1 to 8 mAmps, or 1 to 5 mAmps.

In embodiments, the amplitude is at least 1 volt. In other embodiments, the amplitude ranges from about 1 to 20 volts, 1 to 15 volts, 1 to 10 volts, 1 to 8 volts, or 1 to 5 volts.

In embodiments, the on time is at least about 30 seconds. In other embodiments, the on time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include on times of varying amounts. For example, a therapy cycle can include 1 minutes of on time, 1 minute of off time, 2 minutes of on time, followed by 5 minutes of off time.

In embodiments, the off time is selected in order to allow at least partial recovery of the nerve. In embodiments, the off time may be minimized due to the presence of microsecond inactive phases and/or millisecond inactive phases. In embodiments, off times are at least about 30 seconds. In other embodiments, the off time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include off times of varying amounts. For example, a therapy cycle can include 1 minutes of on time, 1 minute of off time, 2 minutes of on time, followed by 5 minutes of off time.

In embodiments, the first pattern has an amplitude greater than the second pattern. In embodiments, the ratio of the amplitude of the first pattern to the amplitude of the second pattern is at least 10 to 1, 8 to 1, 6 to 1, 4 to 1, 2 to 1 or 4 to 3. In embodiments, the amplitude of the first embodiment is maintained or held constant during the time the first pattern is applied. In other embodiments, the amplitude of the second embodiment, while different than the first pattern, is maintained or held constant during the time period the second pattern of electrical signal is applied.

Figure 10:
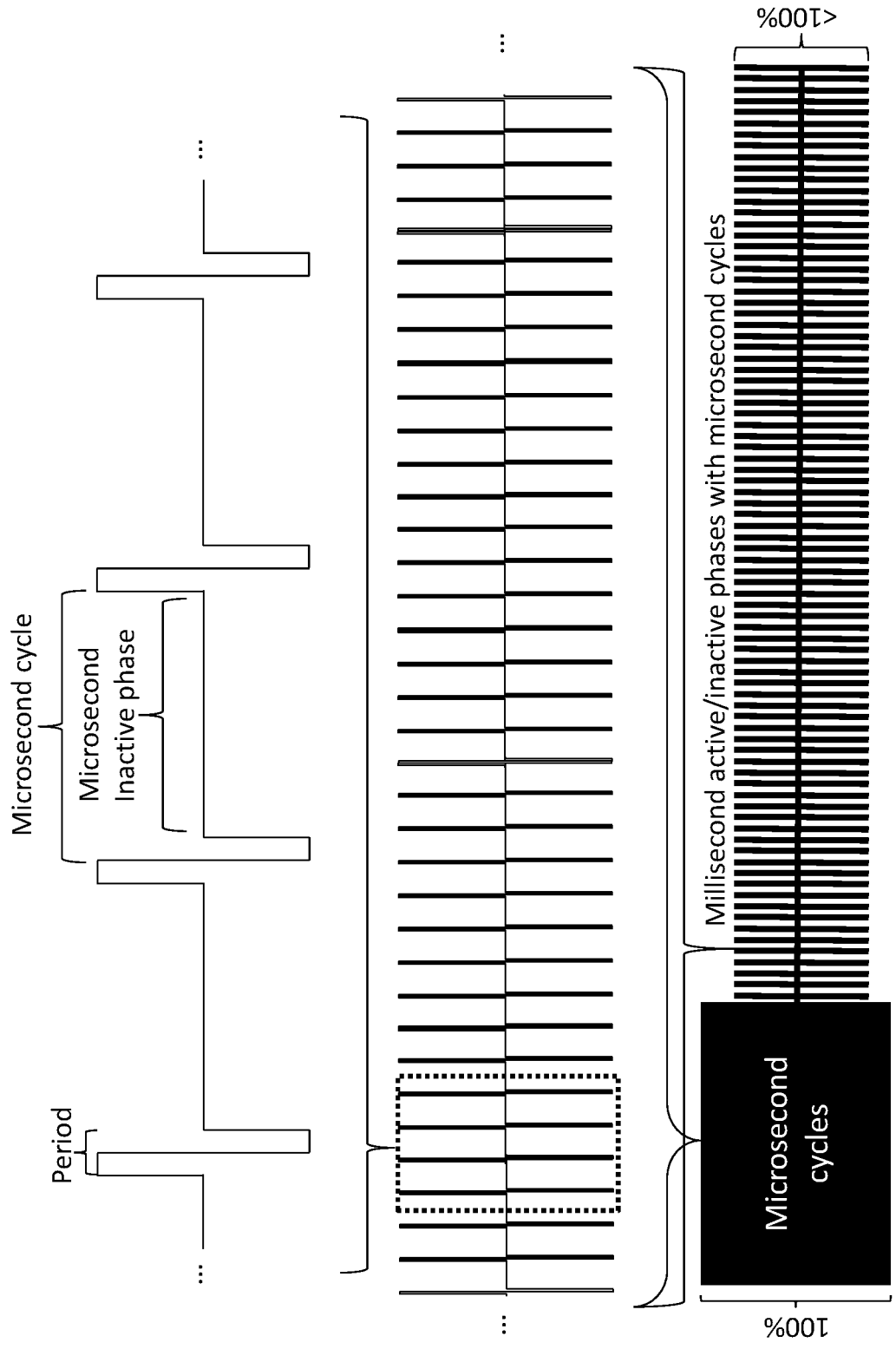
FIG. 10 is a representation of a layered pattern of electrical signals displaying a HFAC/HFAV low duty cycle with microsecond cycles that contain a charge and recharge phase followed by a long microsecond inactive phase. The microsecond cycles are repeated at first pulse amplitude for a period of time (on the order of seconds). Following this (on the order of seconds) the pulse amplitude is decreased to a second pulse amplitude and the repeated microsecond cycles form millisecond active phases. Each millisecond active phase is followed by a millisecond inactive phase at the second amplitude.

An exemplary embodiment is shown in FIG. 10. FIG. 10 shows a first pattern of electrical signals that comprise more than one microsecond cycle, each microsecond cycle having at least one period and a microsecond inactive phase. The period of each microsecond cycle is 5000 microseconds or less. The amplitude of the microsecond cycles is at least about 1 to 20 mAmps, 1 to 15 mAmps, 1 to 10 mAmps, 1 to 8 mAmps, or 1 to 5 mAmps.

FIG. 10 shows a second pattern of electrical signals that comprise one or more millisecond active phases, each millisecond active phase comprising one or more microsecond cycles. Each millisecond active phase has an amplitude that is different than the first pattern. The amplitude of the microsecond cycles in the millisecond active phase is at least about 1 to 20 mAmps, 1 to 15 mAmps, 1 to 10 mAmps, 1 to 8 mAmps, or 1 to 5 mAmps.

In any of the systems and methods described herein, application of an electrical signal can be initiated using a ramp up and/or ramp down of amplitude and/or pulse width. In embodiments, such ramp up and ramp down times are useful to minimize sensations or discomfort from application of an electrical signal to a nerve. In embodiments, a ramp up includes multiple charge recharge phases, each charge recharge phase has an increasing increment of amplitude or an increasing increment of pulse width. In embodiments, a ramp down includes multiple charge recharge phases, each charge recharge phase has a decreasing increment of amplitude or a decreasing increment of pulse width.

The amplitudes can range from about 0.1 to 20 mA, 0.1 to 20 mAmps, 0.1 to 15 mAmps, 0.1 to 10 mAmps, 0.1 to 8 mAmps, or 0.1 to 5 mAmps. In a ramp up, the initial amplitude can be higher than 0.1, for example starting at 3 mAmps. In a ramp down, the initial amplitude can be lower than 20, for example starting at 10 mAmps. In ramp up and/or ramp down the amplitude is changing during the ramp up or down time, whereas in the other methods described herein once a specific amplitude is reached it is maintained for the duration of the first pattern, followed by change to the second amplitude which is then maintained for the duration of the second pattern. In some embodiments, the time period for a ramp up and/or ramp down is about 120 microseconds to 11,000 milliseconds. In some embodiments, a ramping up of the amplitude occupies all of the time of the on time of a first and/or second pattern.

Figure 11:
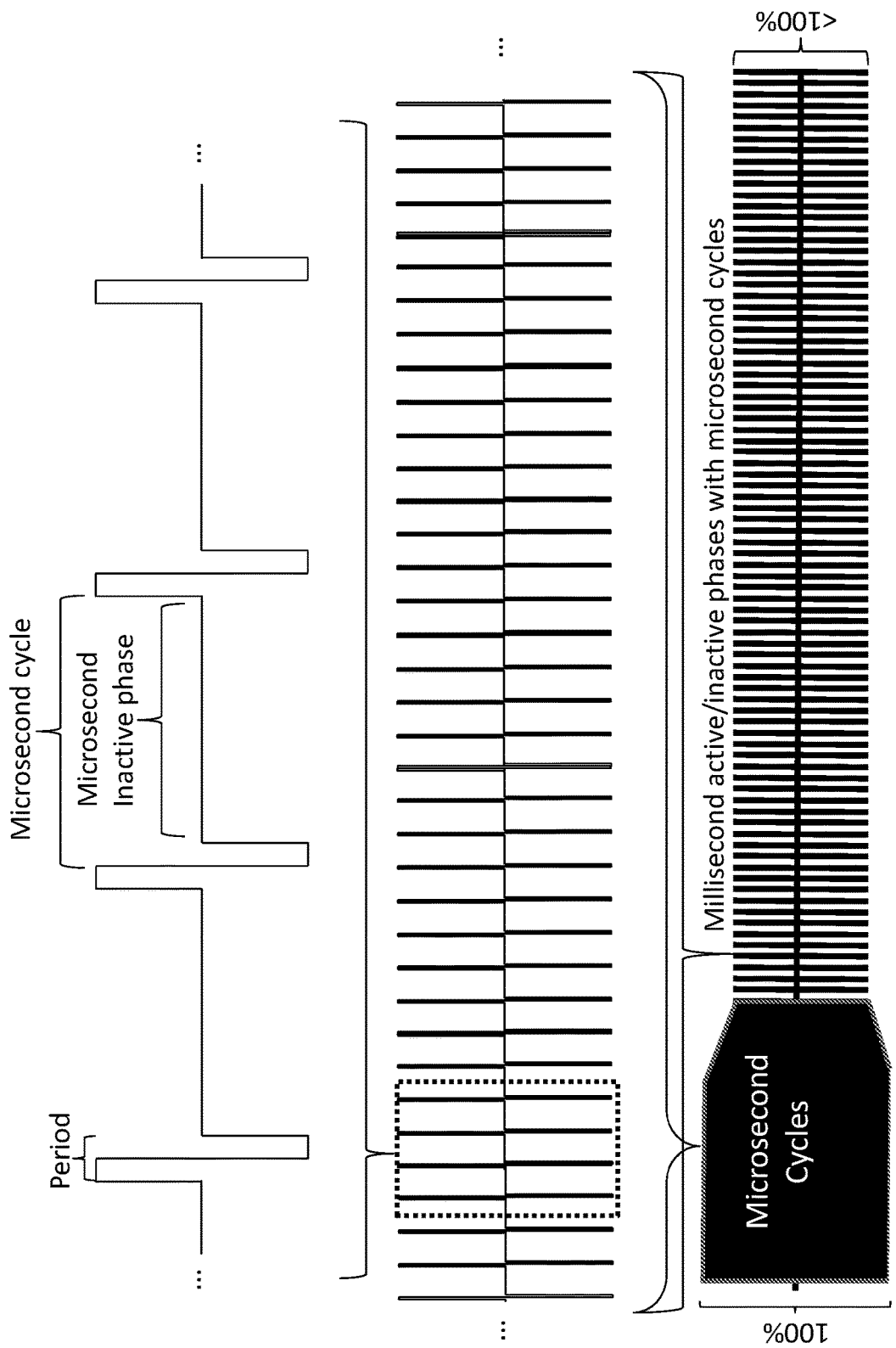
FIG. 11 is a representation of a layered pattern of electrical signals displaying a HFAC/HFAV low duty cycle with microsecond cycles that contain a charge and recharge phase followed by a long microsecond inactive phase. The microsecond cycles are repeated at first pulse amplitude for a period of time (on the order of seconds). Following this (on the order of seconds) the pulse amplitude is decreased to a second amplitude using a ramp down and the repeated microsecond cycles form millisecond active phases. Each millisecond active phase is followed by a millisecond inactive phase at the second amplitude.

An exemplary embodiment is shown in FIG. 11. FIG. 11 shows a first pattern of electrical signals that comprise more than one microsecond cycle, each microsecond cycle having at least one period and a microsecond inactive phase. The period of each microsecond cycle is at least 5000 microseconds. The amplitude of the microsecond cycles is at least about 1 to 20 mAmps, 1 to 15 mAmps, 1 to 10 mAmps, 1 to 8 mAmps, or 1 to 5 mAmps. FIG. 11 shows a ramp down in amplitude from the first pattern to the amplitude of the second pattern. The change is amplitude is applied in increments.

FIG. 11 shows a second pattern of electrical signals that are applied after a ramp down and that comprise one or more millisecond active phases, each millisecond active phase comprising one or more microsecond cycles. Each millisecond active phase has an amplitude that is different than the first pattern. The amplitude of the microsecond cycles in the millisecond active phase is at least about 1 to 20 mAmps, 1 to 15 mAmps, 1 to 10 mAmps, 1 to 8 mAmps, or 1 to 5 mAmps.

3. Duty Cycle

An alternative way to characterize the addition of microsecond and/or millisecond inactive phases is to characterize the addition as a change in a duty cycle. A duty cycle is measured by the percentage of time charge is being delivered to the nerve during one cycle, including either a microsecond cycle, a millisecond cycle, or both. A cycle can also be the length of an on time as in FIGS. 10 and 11. If a signal is being delivered to the nerve with no microsecond inactive phases, pulse delays, or millisecond inactive phases the duty cycle is characterized as 100%. To determine the percentage of the duty cycle being applied during an on time, the pulse widths of the charge and recharge phases of a cycle during an on time (not including any pulse delays) are added and divided by total time of the microsecond and/or millisecond cycle.

In an embodiment, a HFAC/HFAV low duty cycle is illustrated by FIG. 6. If, for example, the pulse width in FIG. 6 is 200 microseconds for each charge and recharge phase, and the microsecond inactive phase is 1600 microseconds the duty cycle can be calculated. The microsecond cycle comprises 400 microseconds of a charge and recharge phase, followed by an inactive phase of 1600 microseconds for a total of 2000 microseconds. The cycle repeats itself for the duration of the on time. The duty cycle is calculated:

(400 microseconds/2000 microseconds)×100=20 percent

This decrease in duty cycle due to microsecond inactive phases is as compared to 100% as shown in FIG. 5.

Yet another embodiment of a HFAC/HFAV low duty cycle with microsecond cycles and pulse delays is illustrated in FIG. 7. As an example, the pulse width is 70 microseconds with 30 microsecond pulse delays between the charge and recharge phase and following the recharge phase. The total time period of the charge recharge phase and pulse delays is 200 microseconds making the frequency 5000 Hz. There is a microsecond inactive phase between the charge/recharge phases of 20 microseconds. During the microsecond cycle charge is delivered for 140 microseconds. The microsecond cycle is 220 microseconds long. The duty cycle is (140 microseconds/220 microseconds)×100=64%.

Another embodiment of a HFAC/HFAV low duty cycle with microsecond cycles forming a millisecond active phase followed by a millisecond inactive phase is illustrated in FIG. 8. As an example of this electrical signal pattern, on the millisecond scale, one repetitive cycle is 60 milliseconds long including a millisecond inactive phase of 20 milliseconds and a millisecond active phase of 40 milliseconds. Each millisecond active phase includes 40 microsecond cycles. Turning to the microsecond cycle, this example has a pulse width of 100 microseconds with one charge and one recharge cycle (making period 200 microseconds and the frequency 5000 Hz) followed by a 800 microsecond inactive phase. For 1000 microseconds charge is being delivered for 200 microseconds. This repeats itself 40 times before the 20 millisecond inactive phase. The amount of time charge is being delivered during the 60 millisecond repetitive cycle is 200 microseconds×40 (total microsecond cycles)=8000 microseconds. Thus, the duty cycle is (8000 microseconds/60 milliseconds)×100=13.3%.

Another embodiment of a HFAC/HFAV low duty cycle with microsecond cycles forming millisecond active phases followed by millisecond inactive phases is illustrated in FIG. 9. On the microsecond scale, the pulse width is 70 microseconds with 30 microsecond pulse delays between the charge and recharge phase and following the recharge phase. The period is 200 microseconds making the frequency 5000 Hz. There is a microsecond inactive phase between the charge/recharge phases of 20 microseconds. The microsecond cycle is 220 microseconds long. The microsecond cycles form a 70.4 millisecond active phase followed by a 29.6 millisecond inactive phase. In the 70.4 millisecond active phase there are 70.4/0.22=320 microsecond cycles. Each microsecond cycle is delivering charge for 140 microseconds. For each millisecond active phase charge is delivered for 140 microseconds×320 microsecond cycles=44,800 microseconds. One repetitive cycle is 100 milliseconds long so the duty cycle is (44,800 microseconds/100 milliseconds)×100=44.8%.

Yet another embodiment of an HFAC/HFAV low duty cycle is illustrated in FIG. 10. The total on time is 120 seconds. As an example, the first pattern is delivered for 30 seconds. The first pattern comprises more than one microsecond cycle, where the pulse amplitude is delivered at first amplitude for 30 seconds, followed by the second pattern of 90 seconds at a second amplitude. The second pattern comprises microsecond cycles which form millisecond active phases followed by millisecond inactive phases with the pulse amplitude reduced 25%. For the first pattern, the microsecond cycles are 1000 microseconds long with a 100 microsecond pulse width for each charge and recharge phase (making the period 200 microseconds and the frequency 5000 Hz) and an 800 microsecond inactive phase. For the second pattern the microsecond cycles are 1000 microseconds long with a 100 microsecond pulse width, one charge and discharge phase (making the period 200 microseconds and the frequency 5000 Hz) and an 800 microsecond inactive phase and form millisecond active phases of 40 milliseconds long followed by a 20 millisecond inactive phases.

The total time charge is being delivered can be broken into two parts and then added together for the example given for FIG. 10. For the first 30 seconds the total time charge is being delivered is calculated as such: for every 1000 microseconds, 200 microseconds of charge is being delivered. This micro repetitive pattern occurs for 30 seconds. Thus, the time that charge is being delivered for the first 30 seconds is 200 (microseconds)/1000 microseconds×30 (seconds)=6 seconds. Calculating the time charge is being delivered for the next 90 seconds is as follows: here there are repetitive phases on the millisecond time scale (60 milliseconds) and on the microsecond time scale (1000 microseconds). On the microsecond time scale the active phase is 200 microseconds long followed by an 800 microseconds inactive phase. This repeats itself 60 times every 60 milliseconds. Thus, for 60 milliseconds the amount of time charge is being delivered is 200 (microseconds)×60 (active phases)

=12,000 microseconds (or 12 milliseconds). In 90 seconds, there are 90×60 milliseconds=1500 of these 60 millisecond repetitive cycles. The total time charge is being delivered for the last 90 seconds of this second pattern would then be 12 milliseconds×1500=18 seconds. For the total 120 seconds of this algorithm the duty cycle would be ((6 seconds+18 seconds)/120 seconds)×100=16.7%.

It should be noted that lowering the duty cycle decreases the amount of energy delivered, but in addition to this, lowering the current amplitude for the last 90 seconds decreases the amount of energy delivered even more.

Decreasing the duty cycle using microsecond and/or millisecond inactive phases results in downregulating activity on the nerve while minimizing the energy requirements needed to downregulate the nerve and maintain down regulation during an on time.

In embodiments, a duty cycle including at least one microsecond and/or millisecond inactive phase is a low duty cycle of about 75% or less, 70% or less, 60% or less, 50% or less, 40% or less, 30% or less, 20% or less, and 10% or less.

In some embodiments, the disclosure provides a low duty cycle high frequency alternating current (HFAC) signal algorithm by utilizing a pulse width that is shorter than the period of the signal. The period of the signal is the length of time of one charge phase and one recharge phase, which can include one or more pulse delays. A shorter pulse width equates with a lower duty cycle and greater energy efficiency is realized. A lower duty cycle can be utilized for frequencies of about 200 Hz to about 25 kHz. The pulse width for a biphasic signal that has a 100% duty cycle for a given frequency is 1 divided by the frequency and further divided by 2.

Figure 18:
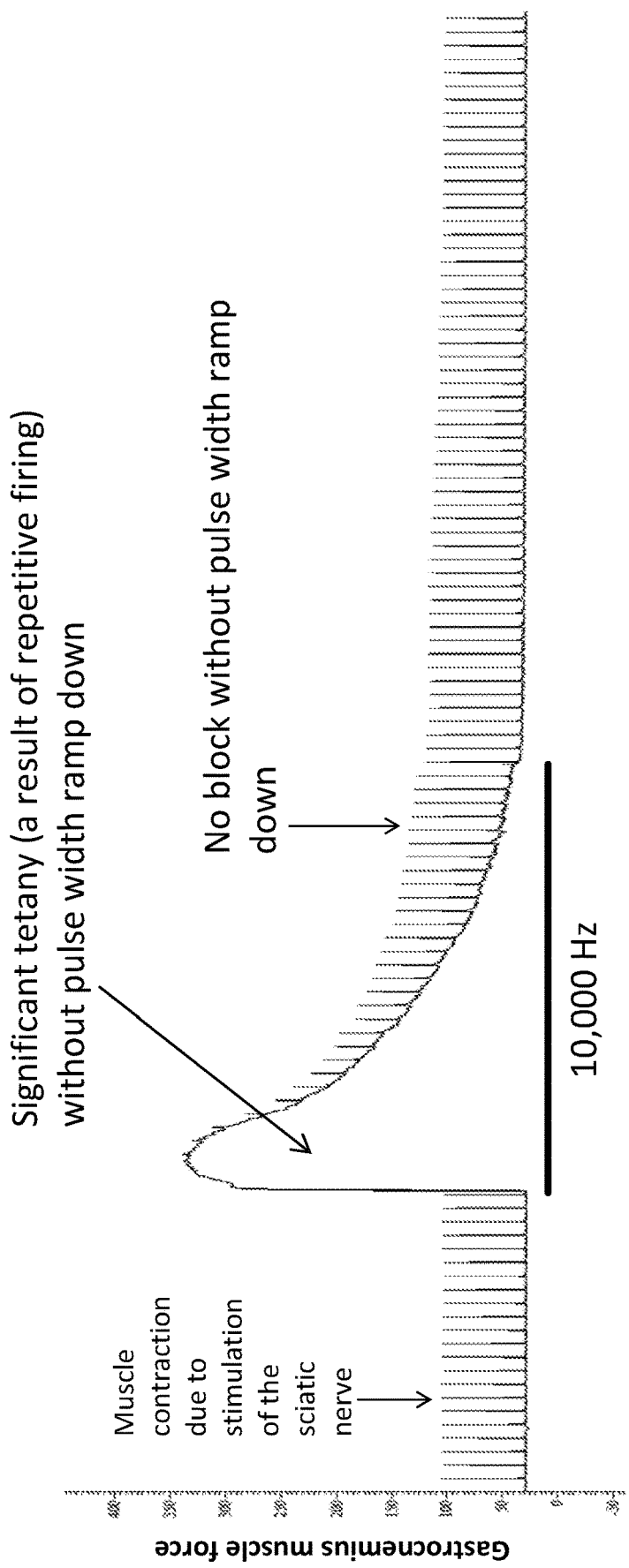
FIG. 18 is a representation of a pulse width of 10 microseconds at a frequency of 10,000 Hz with no pulse ramp down. At a pulse width of 10 microseconds, repetitive firing and tetany is observed, and no block of nerve conduction is seen. This profile represents a pulse width at or below a lower boundary threshold.

In embodiments, the pulse width is selected to be above a lower boundary threshold. While not mean to limit the invention, it is believed that an undesirable end organ response can occur when the duty cycle reaches a lower boundary threshold pulse width. This lower boundary threshold pulse width is substantially below the pulse width for a selected blocking frequency at a 100% duty cycle and is one at which no blocking of the nerve is observed or expected and/or at which repetitive firing is observed. The lower boundary threshold can be determined by applying HFAC for a period of time at a pulse width that is substantially shorter than a pulse width that is 100% of the duty cycle (e.g. 10% duty cycle). An example of this would be a pulse width of 10 microseconds at a frequency of 10,000 Hz with no pulse ramp down (FIG. 18). As shown in FIG. 18, at a pulse width of 10 microseconds, repetitive firing and tetany is observed, and no block of nerve conduction is seen. This profile represents a pulse width at or below a lower boundary threshold.

In embodiments, a lower boundary threshold can be determined by application of a variety of pulse widths without any pulse width ramp down or up and determining whether the patient feels a sensation. Pulse widths resulting in a sensation are at or below a boundary threshold for that frequency. For example, a pulse width is selected for a given frequency at a 10% duty cycle and applied to a patient to determine if the patient feels a sensation. If a sensation is felt, HFAC delivery is then stopped for a period of time to allow patient recovery and applied again at the same frequency as the first application but at a longer pulse width (e.g. 1-10 microseconds longer) than the first application. This would be repeated until the patient does not feel sensations. The pulse width at which the patient no longer feels sensations is above the lower boundary threshold. If at the first application, the patient does not feel sensations the same process would be conducted but the pulse widths would be decreased between each HFAC application. The lower boundary threshold or a pulse width that is at or below the lower boundary threshold would be determined by the pulse width in which the patient first experiences sensations.

In embodiments, employing a pulse width ramp down or ramp up provides for nerve conduction block pulse width at or below a lower boundary threshold. (FIG. 19) Pulse widths with no pulse width ramp down below the blocking lower boundary threshold do not induce conduction block. Going below this boundary and inducing conduction block can be achieved by starting at a pulse width above (e.g. at least 1% longer than the lower boundary threshold up to 100% of the duty cycle) the boundary threshold and ramping down the pulse width until a constant pulse width is reached below the boundary threshold. In embodiments, the ramp down occurs in steps with a duration of about 1 second to 60 seconds at a rate that is linear or non-linear. In other embodiments, the pulse width ramp down could also be continuous which means each successive pulse has a decreased pulse width, and the rate of the continuous pulse width ramp down can be linear or non-linear. In embodiments, the incremental decrease in pulse width would be around 1 to 10 microseconds. In yet other embodiments, during the pulse width ramp down or ramp up the current amplitude (or voltage) can either be increased or decreased. In embodiments, during the pulse width ramp down the time between pulses can either be increased or decreased at a linear or non-linear rate. In other embodiments, during the ramp down the duty cycle can be fixed, increased or decreased.

Figure 19:
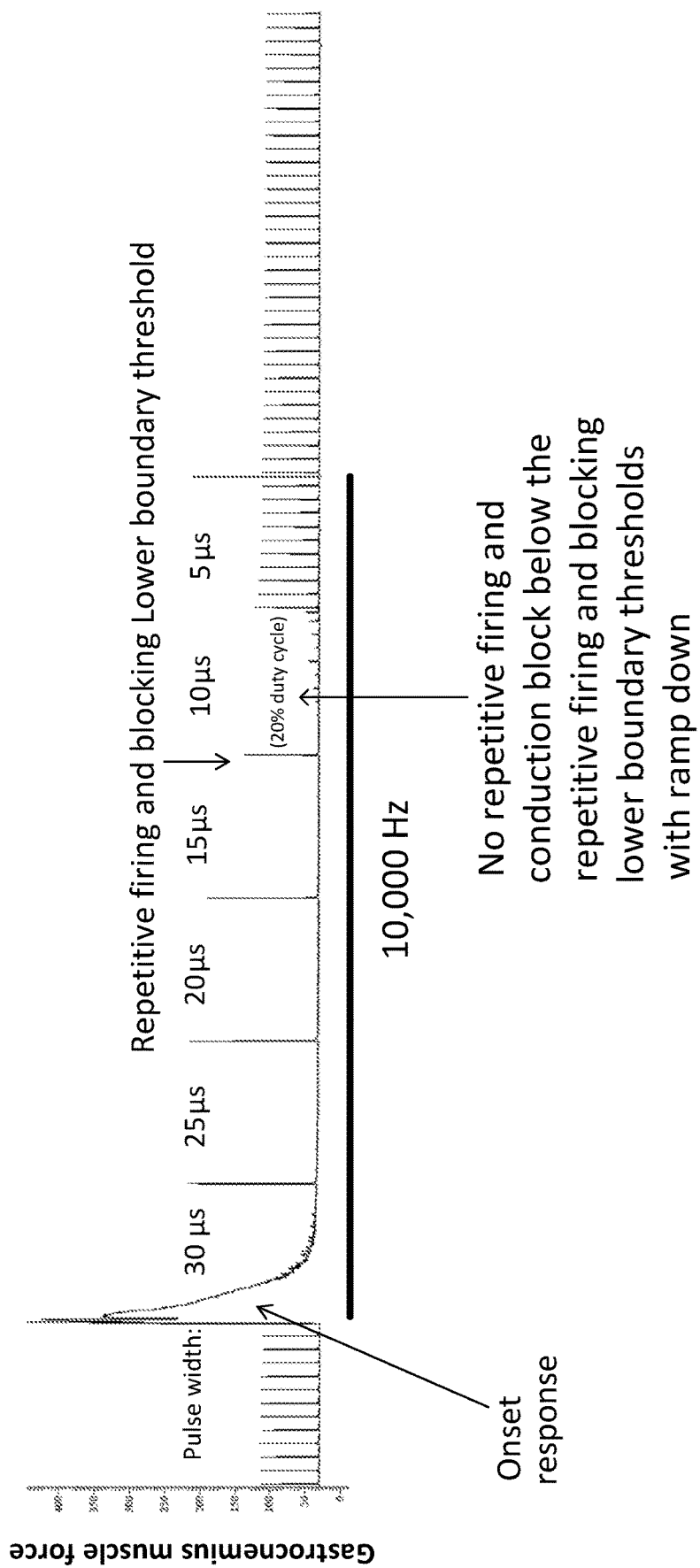
FIG. 19 is a representation of an example of ramping down pulse width to a pulse width below the boundary threshold. At a frequency of 10,000 Hz and an initial pulse width of 30 microseconds (60% duty cycle) the pulse width is decreased to 25 microseconds for 20 seconds. Next the pulse width would decrease to 20 microseconds for 20 seconds and next to 15 microseconds for 20 seconds and follow the same pattern until the pulse width reaches 5 microseconds (10% duty cycle) and is constant for the duration of the on time. Blocking of the nerve occurs at pulse width of 5 microseconds at a frequency of 10,000 Hz with a current amplitude of 0.1 mA to 20 mA.

FIG. 19 is an example of ramping down pulse width to a pulse width below the boundary threshold. For example, at a frequency of 10,000 Hz and an initial pulse width of 30 microseconds the pulse width is decreased to 25 microseconds for 20 seconds. Next the pulse width would decrease to 20 microseconds for 20 seconds and next to 15 microseconds for 20 seconds and follow the same pattern until the pulse width reaches 5 microseconds and is constant for the duration of the on time. Blocking of the nerve occurs at pulse width of 5 microseconds at a frequency of 10,000 Hz with a current amplitude of 0.1 mA to 20 mA depending on electrode placement and impedance.

Figure 20:
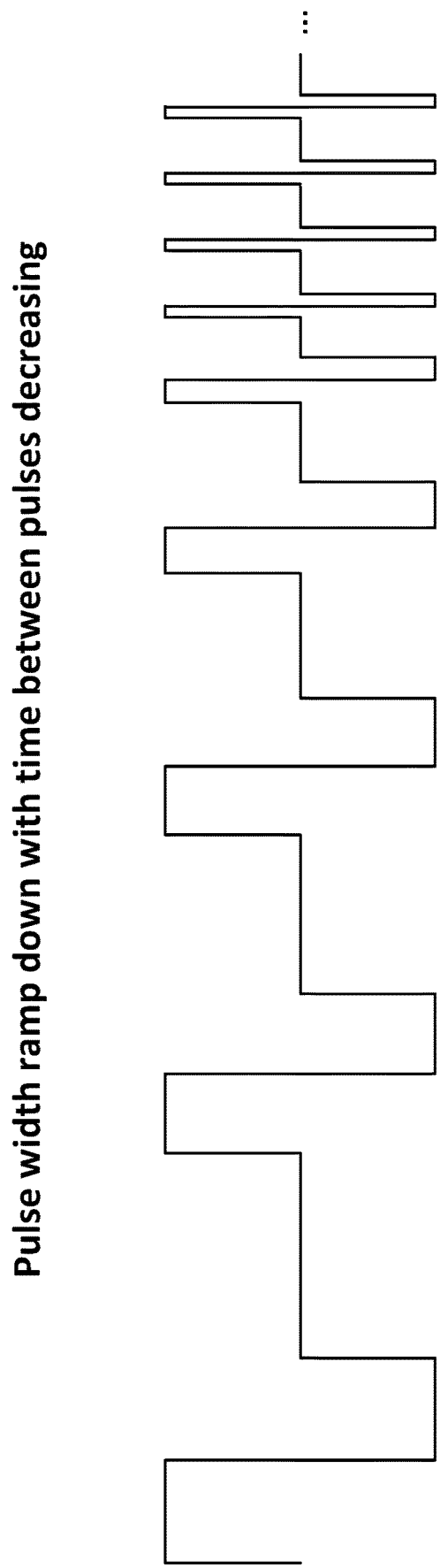
FIG. 20 is a representation of an exemplary embodiment of a pulse width ramp down with time between pulses decreasing.

In some embodiments, a pulse width ramp down or ramp up can vary not only in the pulse width but also in the time between pulses. For example, FIG. 20 shows a pulse width ramp down with time between pulses decreasing. In embodiments, decreasing the time between pulses and the pulse width duration at the same time the duty cycle remains constant. In other embodiments, in a pulse width ramp up the time between the pulses can be increasing at the same time and the duty cycle would remain constant.

Figure 21:
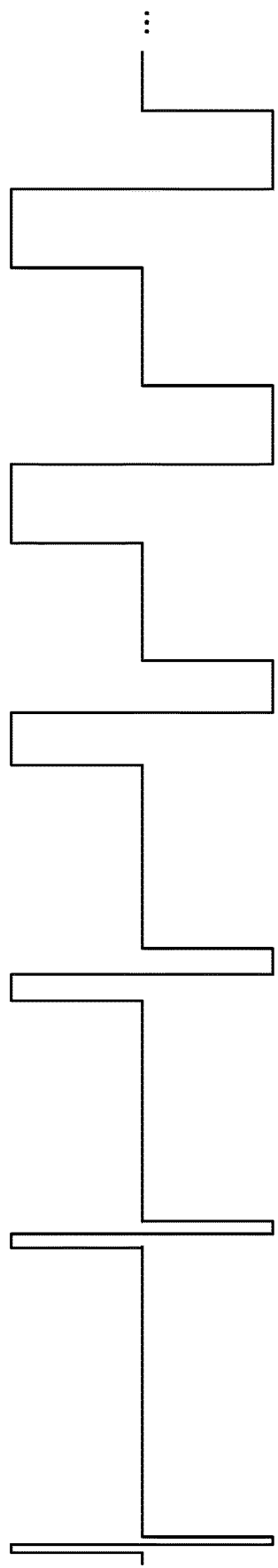
FIG. 21 is a representation of an exemplary embodiment of a pulse width ramp up with time between pulses decreasing.

In some embodiments, ramping up of pulse widths is desired (see FIG. 21). In this embodiment, the pulse width at the start of HFAC delivery would be lower than the lower boundary threshold. Starting with pulse widths lower than the lower boundary threshold and ramping up pulse width durations may eliminate the repetitive firing. In embodiments, the ramp up can occur in steps with a duration of about 1 second to 60 seconds at a rate that is linear or non-linear. In other embodiments, the pulse width ramp up could also be continuous which means each successive pulse has an increased pulse width. The rate of the continuous pulse width ramp up can be linear or non-linear. In embodiments, the incremental increase in pulse width would be around 1 to 10 microseconds. In embodiments, during the pulse width ramp up the current amplitude (or voltage) can either be increased or decreased. In other embodiments, during the pulse width ramp up the time between pulses can either be increased or decreased at a linear or non-linear rate. During the ramp up the duty cycle can be fixed, increased or decreased.

To eliminate nerve activity, and undesirable sensations, during or at the initiation of a high frequency alternating current conduction block (HFAC), a pulse width ramp down can be used in combination with a current (or voltage) ramp down. Initiation of HFAC with an amplitude that is substantially (about 5 times) above a blocking threshold may eliminate an onset response. A blocking threshold is a current (or voltage) amplitude in which conduction block is realized with a HFAC signal at or above the current (or voltage) threshold and no blockade (or a partial block) occurs below this amplitude. The power consumption of a HFAC pulse generator is considerable and a sustained current (or voltage) output that is substantially greater than the blocking threshold would not be desirable. Initiation of HFAC with a considerably high current (or voltage) amplitude and decreasing the level, in a linear or non-linear rate, may avoid an onset response and sustain blockade when the current (or voltage) amplitude is lowered to the blocking threshold.

Lower energy consumption can also be realized by a low duty cycle in which the pulse width of the HFAC signal is substantially lower than half of the period of the signal. However, sustained repetitive firing of action potentials for the duration of the signal and non-realization of conduction block may occur at short pulse widths (below the lower boundary pulse width threshold, FIG. 18). The probability of these unwanted effects decreases at pulse widths that are half (100% duty cycle), or close to half (approximately 90% duty cycle), of the duration of the period of the HFAC signal. Initiation of HFAC with pulse widths at or close to a 100% duty and ramping down the duration of the pulse width to a low duty cycle, below the lower boundary threshold, may eliminate continuous repetitive firing of action potentials for the duration of the HFAC signal and un-realized blockade (FIG. 19). With this method energy savings would be realized without the aforementioned unwanted side effects.

A combination of current (or voltage) ramp down with a concurrent pulse width ramp down (FIGS. 22 and 23) would decrease repetitive firing at the onset of block as well as during the course of the block with using a low duty cycle signal. $A_x$ indicates the area of the charge and recharge phases. The area of the charge phase equals the area of the recharge phase for each cycle to avoid a direct current offset. The areas progressively decrease due to the decrease in pulse width in combination with a decrease in amplitude. X depicts that the time from the start of the charge phase to the start of the recharge phase remains constant. However, this can vary in a linear or non-linear rate. The current (or voltage) ramp down could occur continuously with the pulse width ramp down. The current (or voltage) ramp down could precede or follow the pulse width ramp down. The rate of the current (or voltage) ramp down could be the same or different than the pulse width ramp downs. The rates of the current (or voltage) ramp downs may be linear or non-linear or switch from linearity to non-linearity during the ramps, or vice versa. In other instances a current (or voltage) ramp down could occur with a fixed low duty cycle HFAC signal. In other instances the pulse width ramp down could occur with a fixed current (or voltage).

Figure 22:
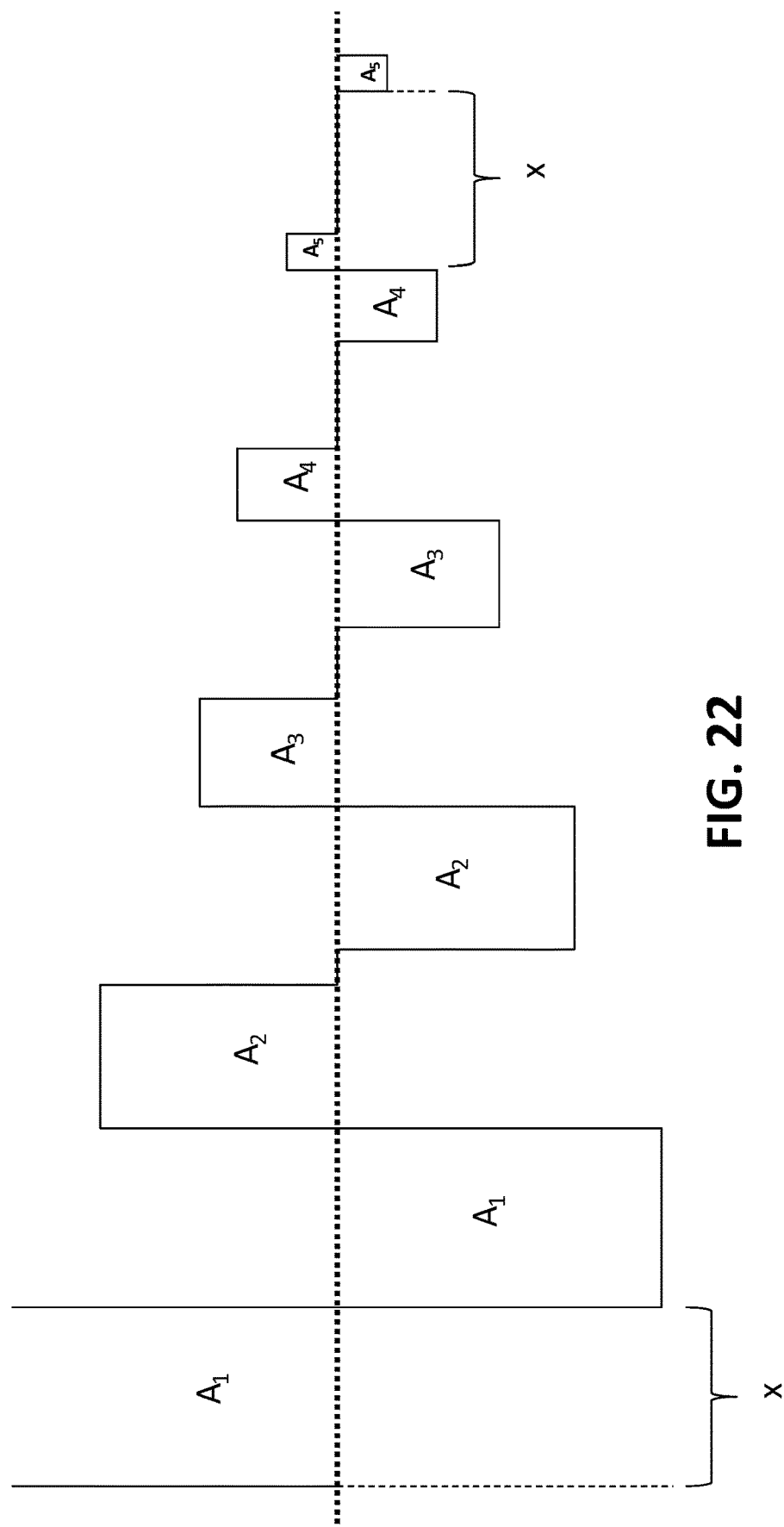
FIG. 22 is a representation of an exemplary embodiment of a pulse width ramp down in combination with current/voltage ramp down and no pulse delays.
Figure 23:
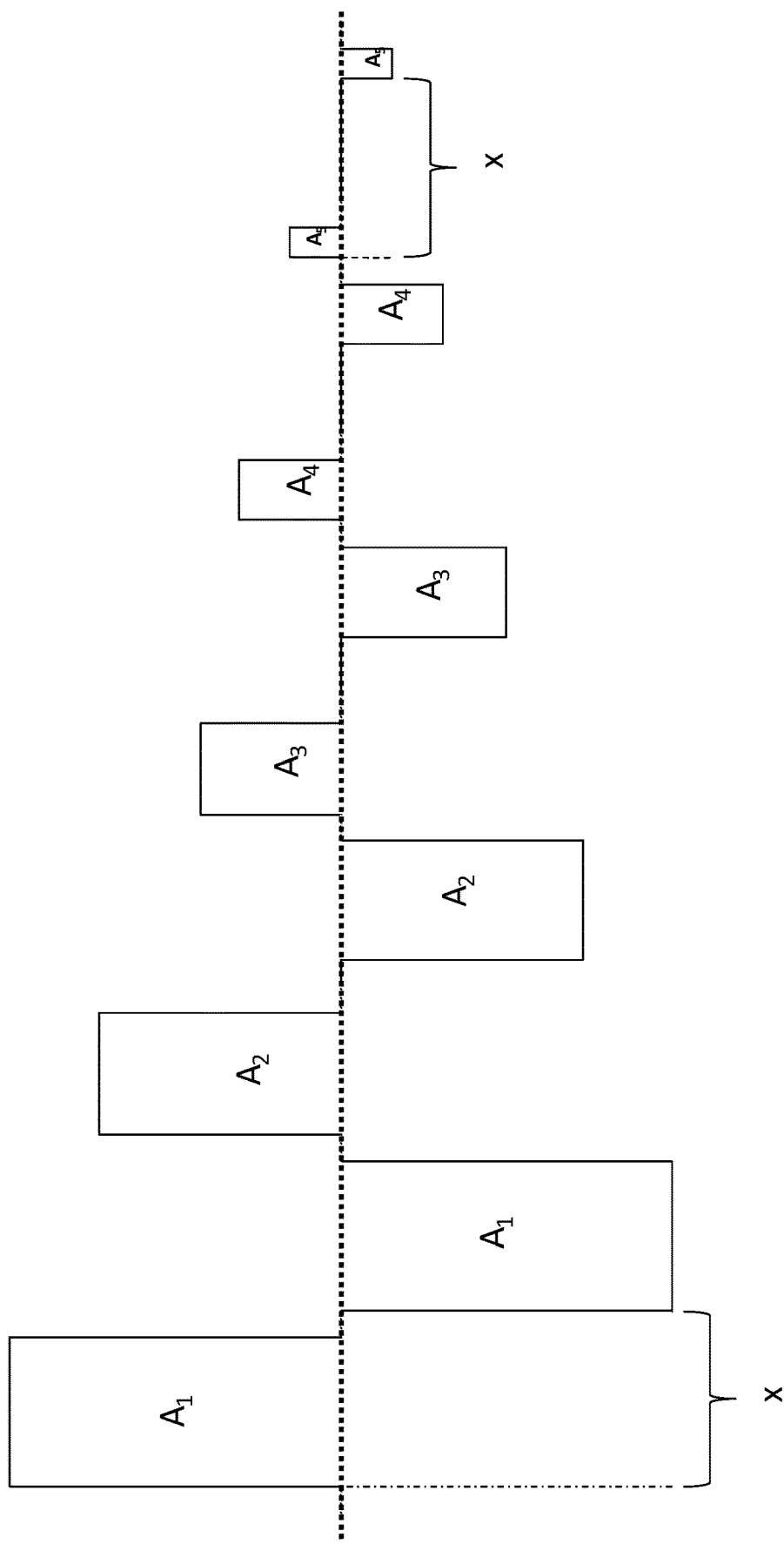
FIG. 23 is a representation of an exemplary embodiment of a pulse width ramp down in combination with current/voltage ramp down and pulse delays.
Figure 24:
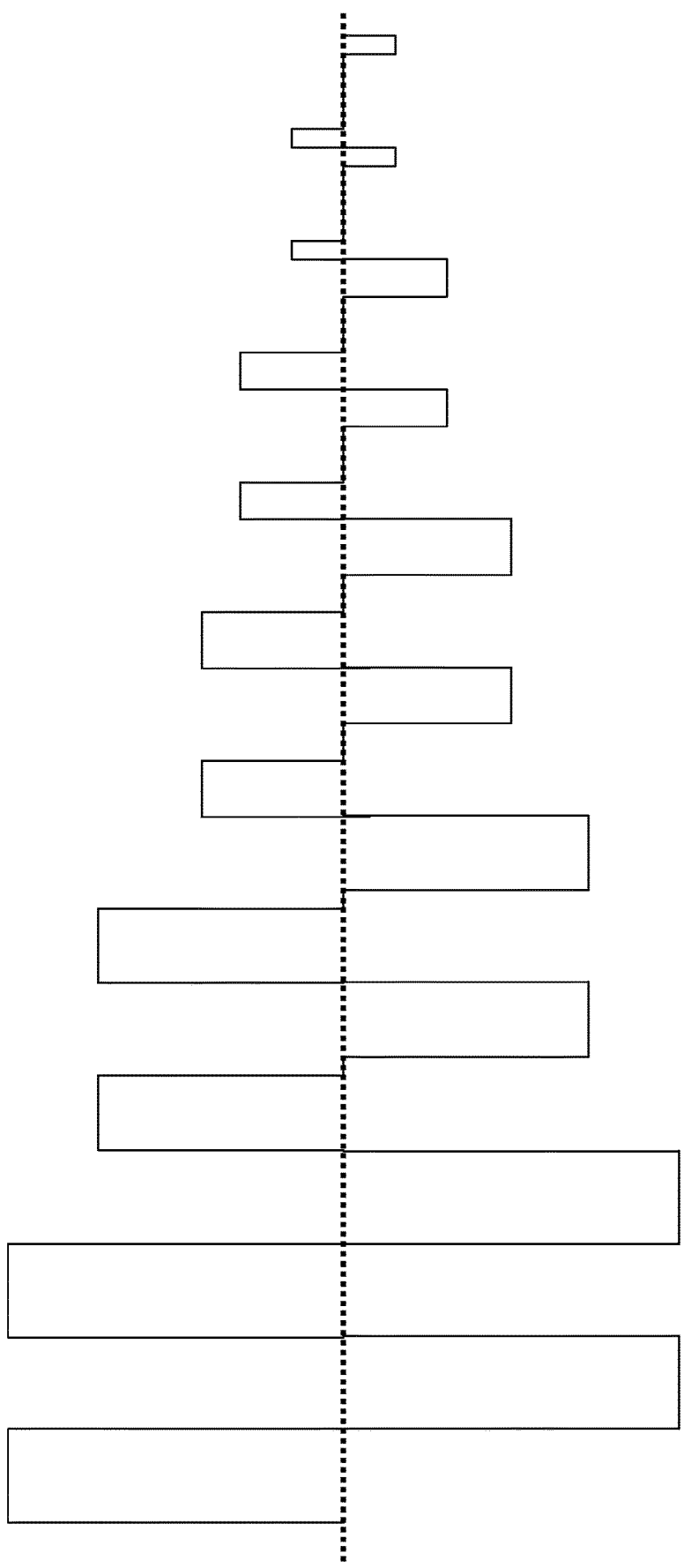
FIG. 24 is a representation of an exemplary embodiment of a pulse width ramp down in combination with current/voltage ramp down and no pulse delays in 2 cycle steps.

The current (or voltage) and/or pulse width ramp down can be continuous or occur in steps (FIG. 24). FIG. 24 describes a pulse width ramp down in combination with current/voltage ramp down and no pulse delays in 2 cycle steps. Cycles per steps can range up to the number of cycles to fill an about 5 min period. Steps for the pulse width ramp down and/or current (or voltage) ramp down could be as low as two cycles or as many cycles that fill about 5 minutes. Steps for the duration of the pulse widths can be 1% to 99% of the initial pulse width. The steps for the current (or voltage) ramp down can be from 0.1 mA (or volts) to 19.9 mA (or volts). For each cycle the area of the charge and recharge phase are the same (FIGS. 22 and 23). The entire time of the current (or voltage) and/or pulse width ramps can range from about 5 seconds to 30 minutes. Current amplitudes at the initiation of the ramp down can range from about 0.2 mA to about 20 mA. Voltage amplitudes can range from about 0.2 volts to about 20 volts. Frequencies can range from about 200 Hz to 25 kHz.

Figure 25:
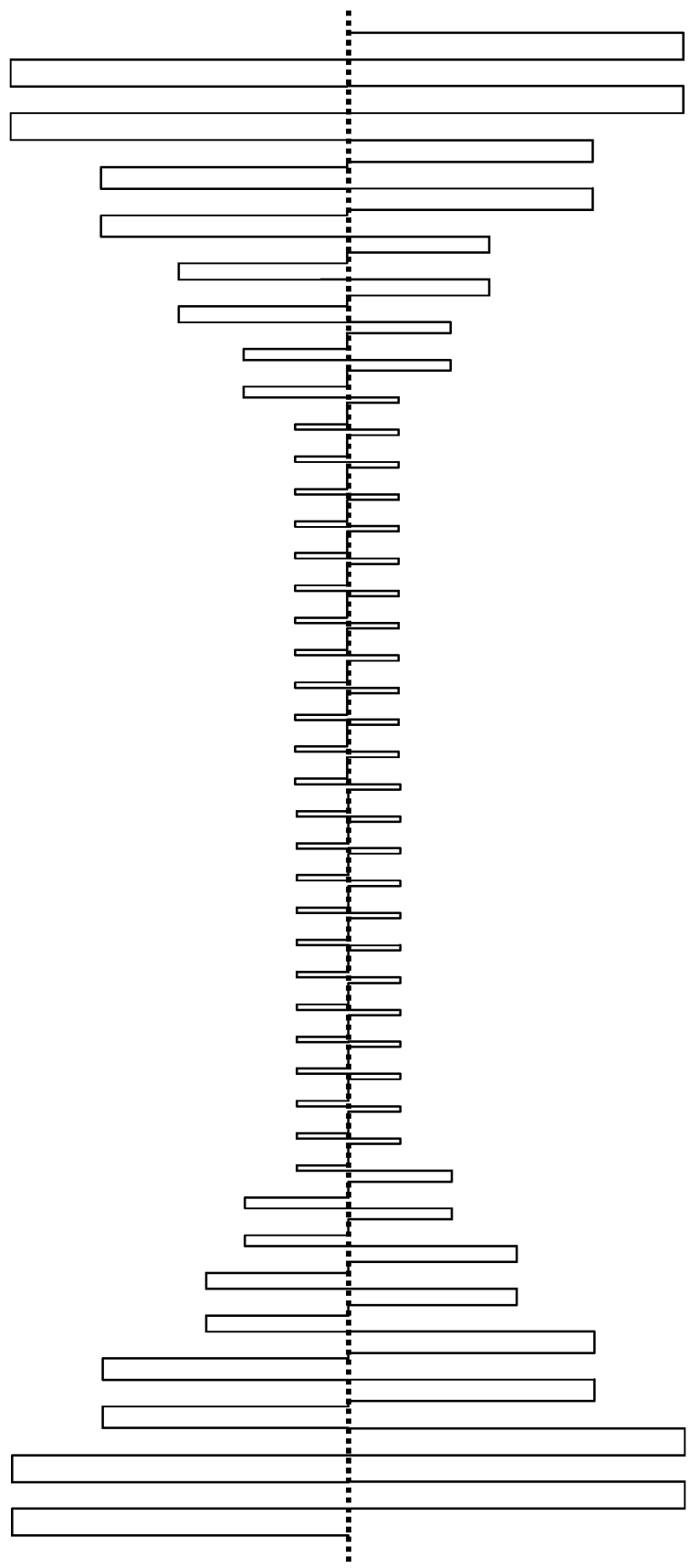
FIG. 25 is a representation of an exemplary embodiment of a pulse width and current (or voltage) ramp down followed by a steady state low duty cycle signal and a pulse width and current (or voltage) ramp up before termination of the signal.
Figure 26:
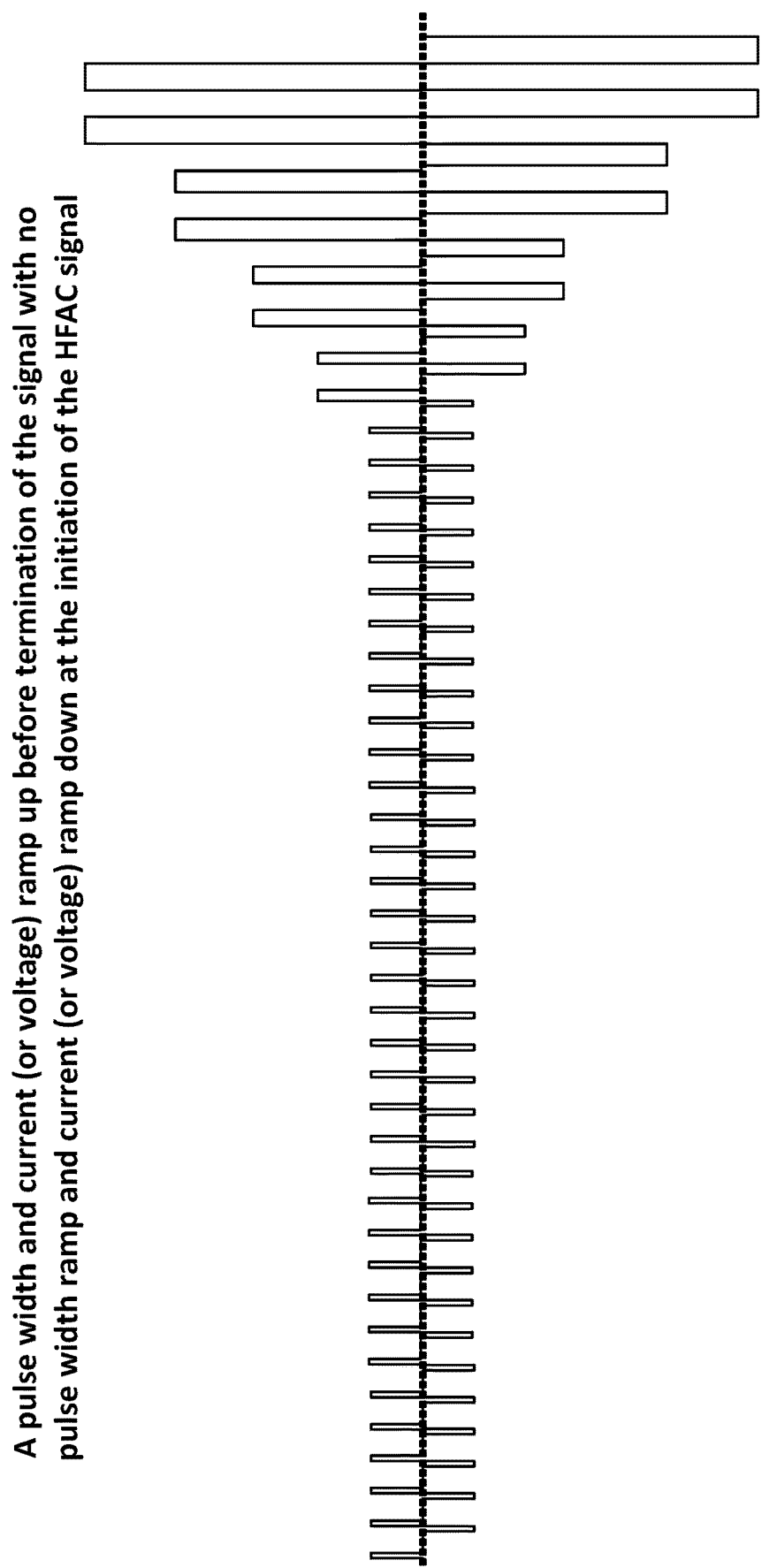
FIG. 26 is a representation of an exemplary embodiment of a steady state low duty cycle followed by a ramp up of pulse width and current (or voltage) before termination of the signal.

Nerve activity can occur at the termination of HFAC. To avoid this a ramp up of current (or voltage) and/or pulse width ramp up can occur prior to the cessation of 5000 Hz (FIG. 25). The ramps can occur about 5 second to 30 min prior to the termination of the HFAC signal. The rate of the ramp ups can be linear or non-linear or switch from linearity to non-linearity, or vice versa, during the ramp. The voltage and current ramps can be concurrent or non-concurrent. For example the voltage ramp can precede or follow the pulse width ramp. The ramp up can be continuous or occur in steps. Steps for the pulse width ramp up and/or current (or voltage) ramp up could be as low as two cycles or as many cycles that fill about 5 minutes. Steps for the duration of the pulse widths can be 1% of the duty cycle to 99% of the final pulse width. The steps for the current (or voltage) ramp up can be from 0.1 mA (or volts) to 19.9 mA (or volts). For each cycle the area of the charge and recharge phase are the same. In other instances a current (or voltage) ramp up could occur with a fixed duty cycle HFAC signal. In other instances the pulse width ramp up could occur with a fixed current (or voltage).

4. Therapy Programs

The external charger 101 and/or the neuroregulator 104, 104' contain software to permit use of the therapy system 100 in a programmable variety of therapy schedules, electrical signal delivery, therapy programs, operational modes, system monitoring and interfaces as will be described herein.

In embodiments, system software can be stored on a variety of computer devices, such as an external smartphone or tablet, external programmer, the neuroregulator, and/or external charger.

Figure 12:
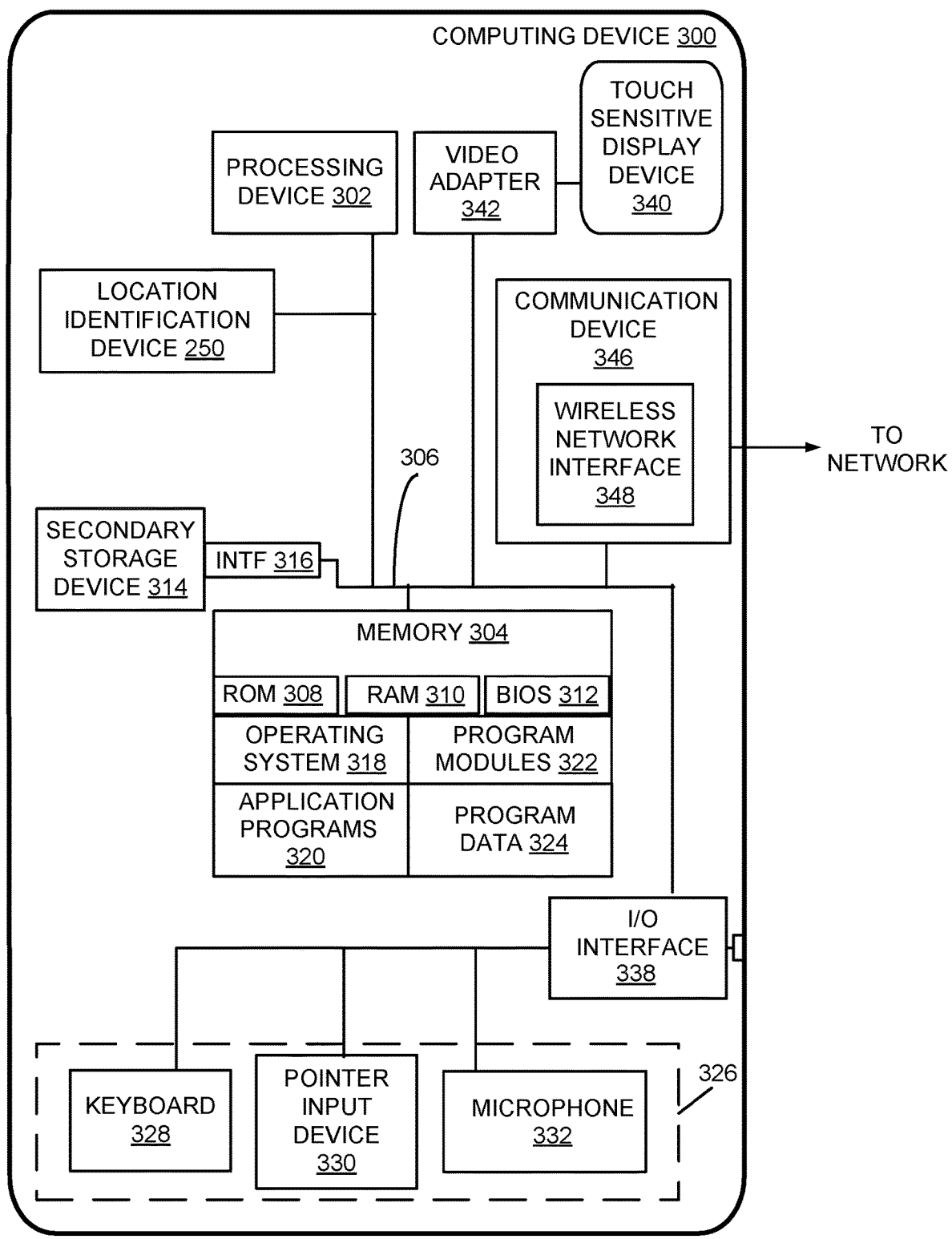
FIG. 12 illustrates an exemplary architecture of a computing device that can be used to implement aspects of the present disclosure.

Referring to FIG. 12, an exemplary architecture of a computing device that can be used to implement aspects of the present disclosure is illustrated. For example, the external charger 101, the neuroregulator 104, 104', an external programmer, an external smartphone of tablet, or various systems and devices of the therapy system 100 can be implemented with at least some of the components of the computing device as illustrated in FIG. 12. Such a computing device is designated herein as reference numeral 300. The computing device 300 is used to execute the operating system, application programs, and software modules (including the software engines) described herein.

The computing device 300 includes, in some embodiments, at least one processing device 302, such as a central processing unit (CPU). A variety of processing devices are available from a variety of manufacturers, for example, Intel or Advanced Micro Devices. In this example, the computing device 300 also includes a system memory 304, and a system bus 306 that couples various system components including the system memory 304 to the processing device 302. The system bus 306 is one of any number of types of bus structures including a memory bus, or memory controller; a peripheral bus; and a local bus using any of a variety of bus architectures.

Examples of computing devices suitable for the computing device 300 include a desktop computer, a laptop computer, a tablet computer, a mobile device (such as a smart phone, an iPod® mobile digital device, or other mobile devices), or other devices configured to process digital instructions.

The system memory 304 includes read only memory 308 and random access memory 310. A basic input/output system 312 containing the basic routines that act to transfer information within computing device 300, such as during start up, is typically stored in the read only memory 308.

The computing device 300 also includes a secondary storage device 314 in some embodiments, such as a hard disk drive, for storing digital data. The secondary storage device 314 is connected to the system bus 306 by a secondary storage interface 316. The secondary storage devices and their associated computer readable media provide nonvolatile storage of computer readable instructions (including application programs and program modules), data structures, and other data for the computing device 300.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 314 or memory 304, including an operating system 318, one or more application programs 320, other program modules 322, and program data 324.

In some embodiments, computing device 300 includes input devices to enable a user to provide inputs to the computing device 300. Examples of input devices 326 include a keyboard 328, pointer input device 330, microphone 332, and touch sensitive display 340. Other embodiments include other input devices 326. The input devices are often connected to the processing device 302 through an input/output interface 338 that is coupled to the system bus 306. These input devices 326 can be connected by any number of input/output interfaces, such as a parallel port, serial port, game port, or a universal serial bus. Wireless communication between input devices and interface 338 is possible as well, and includes infrared, BLUETOOTH® wireless technology, WiFi technology (802.11a/b/g/n etc.), cellular, or other radio frequency communication systems in some possible embodiments.

In this example embodiment, a touch sensitive display device 340 is also connected to the system bus 306 via an interface, such as a video adapter 342. The touch sensitive display device 340 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 340, the computing device 300 can include various other peripheral devices (not shown), such as speakers or a printer.

The computing device 300 further includes a communication device 346 configured to establish communication across the network. In some embodiments, when used in a local area networking environment or a wide area networking environment (such as the Internet), the computing device 300 is typically connected to the network through a network interface, such as a wireless network interface 348. Other possible embodiments use other wired and/or wireless communication devices. For example, some embodiments of the computing device 300 include an Ethernet network interface, or a modem for communicating across the network. In yet other embodiments, the communication device 346 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 300 typically includes at least some form of computer-readable media. Computer readable media includes any available media that can be accessed by the computing device 300. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 300.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

As described above, the computing device typically includes at least some form of computer-readable media. Computer readable media includes any available media that can be accessed by the computing device. By way of example, computer-readable media include computer readable storage media and computer readable communication media.

The computer implemented methods as described herein are implemented by storing a series of instructions on the neuroregulator, external programmer, and/or the external charger. In embodiments, a user may select parameters of the electrical signal therapy and upon selection, selects a combination of electrical signal treatments including at least one micro second cycle, and/or at least one millisecond cycle and/or at least one millisecond inactive phase.

Figure 13:
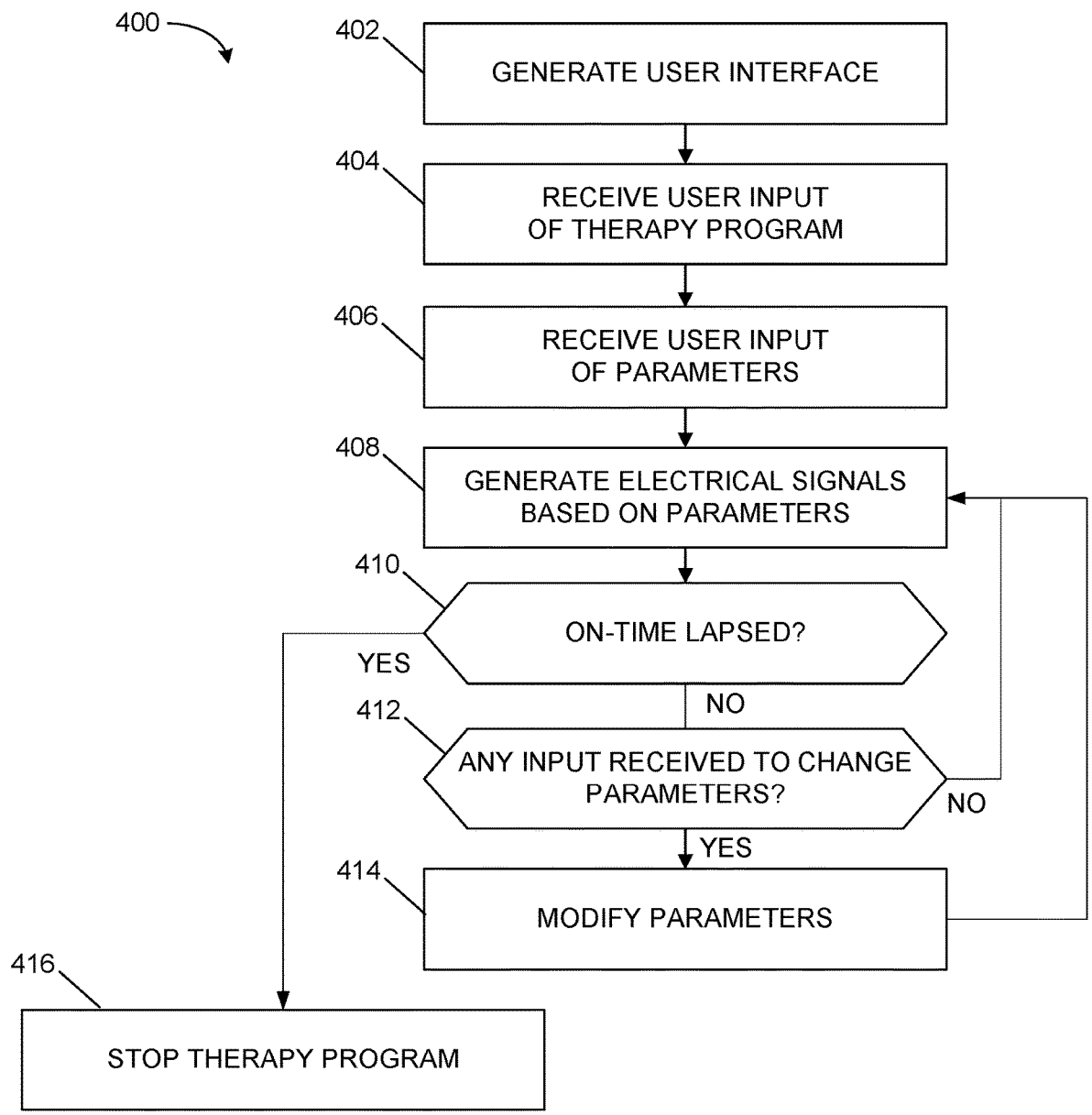
FIG. 13 is a flowchart illustrating an exemplary method of operating the therapy system.

Referring to FIG. 13, an example method 400 of operating the therapy system 100 is illustrated. At operation 402, the system 100 generates a user interface configured to receive various inputs from a user, such as one or more parameters, therapy programs, schedules, and any other information usable for system operation. At operation 404, the system 100 receives a user input of a therapy program via the user interface. As described herein, the system 100 is configured to provide a plurality of therapy programs, and the user can select one of the therapy programs available through the user interface. At operation 406, the system 100 receives a user input of one or more parameters that determine the characteristics of a therapy program.

Examples of the parameters are described with reference to FIG. 14. At operation 408, the system 100 generates electrical signals based on the selected parameters, which implement the therapy program selected by the user. At operation 410, it is determined whether the on-time has lapsed. If so ("YES" at the operation 410), the system 100 stops the therapy program. If not ("NO" at the operation 410), the system 100 determines if there is any input for changing one or more of the parameters, at operation 412. If so ("YES" at the operation 412), the system 100 modifies the parameters based on the input, and continues the operation 408 and the subsequent operations. If not ("NO" at the operation 412), the system 100 continues the operation 408 and the subsequent operations.

Figure 14:
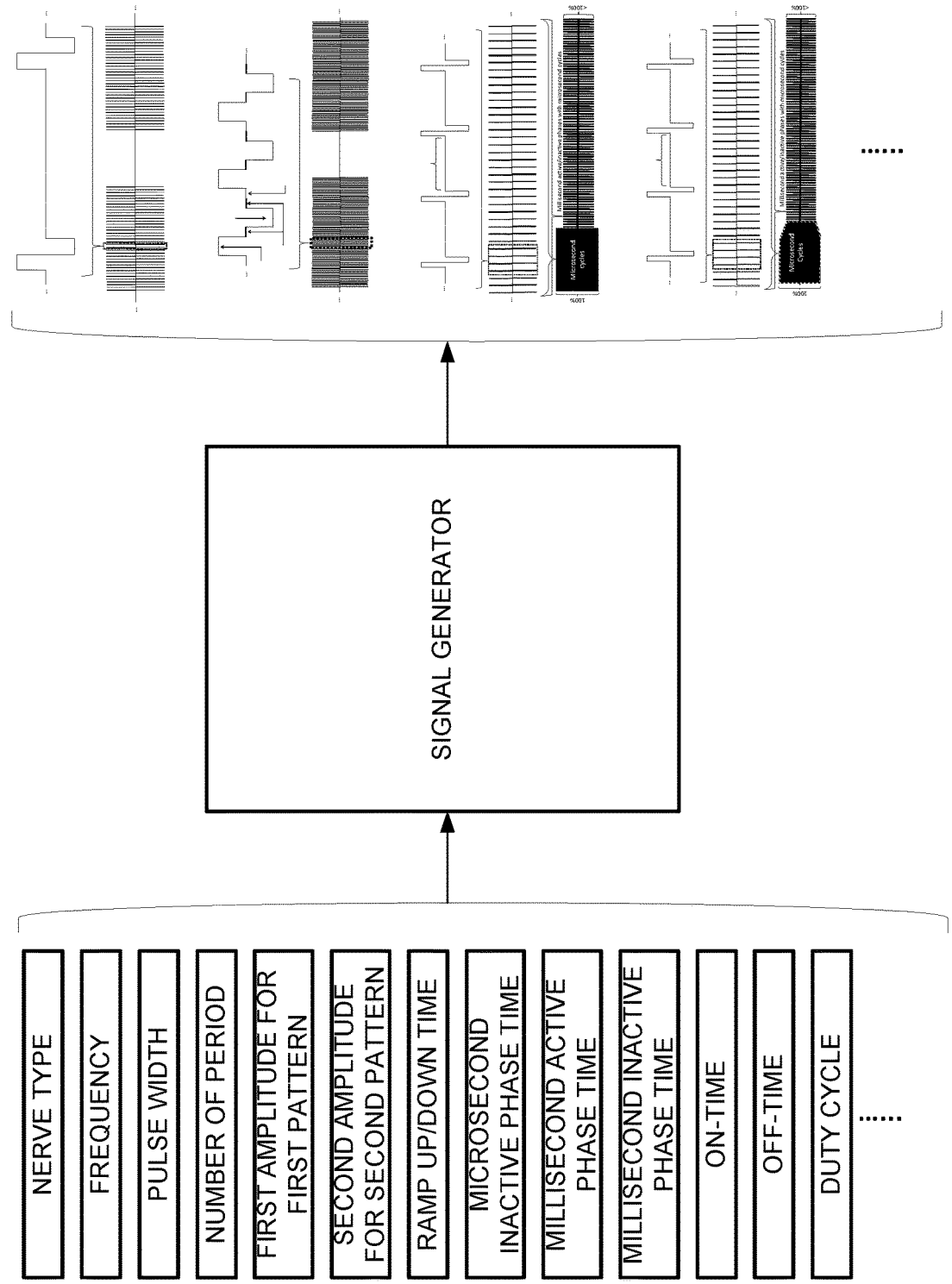
FIG. 14 illustrates a plurality of parameters usable for various types of therapy treatment signals.

As illustrated in FIG. 14, the system 100 receives and utilizes a plurality of parameters to generate various patterns of electrical signals for different therapy programs. Examples of the parameters are described as follows:

Parameters that are selected by a user include type of nerve. In embodiments, the type of nerve is selected from vagus nerve, renal nerve, renal artery, sympathetic nerves, and glossopharyngeal nerve.

In embodiments, a user selects a frequency of at least 200 Hz. In embodiments, the frequency choices in each period of a microsecond cycle are at least 200 Hz, at least 250 Hz, at least 300 Hz, at least 400 Hz, at least 500 Hz, at least 1000 Hz, at least 2000 Hz, at least 3000 Hz, at least 4000 Hz, or at least 5000 Hz. In other embodiments, the frequencies range from about 200 Hz to 25 kHz, 200 Hz to 20 kHz, 200 Hz to 15 kHz, 200 Hz to 10 kHz, 200 to 5 kHz, 200 to 2.5 kHz, 200 to 1 kHz, or 200 to 500 Hz. In other embodiments, the frequencies range from about 1000 Hz to 25 kHz, 1000 Hz to 20 kHz, 1000 Hz to 15 kHz, 1000 Hz to 10 kHz, 1000 to 5 kHz, or 1000 Hz to 2.5 kHz. In other embodiments, the frequencies range from about 1000 Hz to 10 kHz, 1000 Hz to 9000 Hz, 1000 Hz to 8000 Hz, 1000 Hz to 7000 Hz, 1000 to 6000 Hz, 1000 Hz to 5000 Hz, 1000 Hz to 4000 Hz, 1000 Hz to 3000 Hz, or 1000 Hz to 2000 Hz.

In some embodiments, a user selects a frequency of 300 Hz or less. In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

Optionally, a user may select a pulse width for each charge and recharge phase. The pulse width chosen for a particular frequency will depend on whether one or more pulse delays are included within the period. In embodiments, pulse delay selections include at least 5 microseconds, 10 microseconds, 20 microseconds, or 30 microseconds.

In embodiments, a user may select the number of periods in a microsecond cycle. In embodiments, the number of periods is at least 2 periods. In embodiments, the number periods in a microsecond cycle can range for 2 to 20, 2 to 15, 2 to 10, or 2 to 5 periods in a microsecond cycle.

A user may also select a first and/or second amplitude. In embodiments, the first selected amplitude is applied to first pattern of electrical signal treatment. In embodiments, a second selected amplitude is applied to a second pattern of electrical signal treatment, where the first and second amplitudes are different from one another. The selections of amplitudes include about 1 to 20 mAmps, 1 to 15 mAmps, 1 to 10 mAmps, 1 to 8 mAmps, or 1 to 5 mAmps. In embodiments, the first and/or second amplitude is constant during the time period of the electrical signal treatment. In embodiments, the amplitude is at least 1 volt. In other embodiments, the amplitude ranges from about 1 to 20 volts, 1 to 15 volts, 1 to 10 volts, 1 to 8 volts, or 1 to 5 volts. In embodiments, a single amplitude or voltage is selected.

In yet other embodiments, a user can select a ramp up and/or a ramp down time for amplitude and/or pulse width. During the ramp up and ramp down time the amplitude or pulse width is changing. In embodiments, the amplitudes for ramp up include about 0.1 to 20 mAmps, 0.1 to 15 mAmps, 0.1 to 10 mAmps, 0.1 to 8 mAmps, or 0.1 to 5 mAmps. In embodiments, the amplitude for a ramp up is at least 1 volt. In other embodiments, the amplitude ranges from about 1 to 20 volts, 1 to 15 volts, 1 to 10 volts, 1 to 8 volts, or 1 to 5 volts. In embodiments, the time or ramp up and/or ramp down is about 200 microseconds to 25 milliseconds.

In embodiments, a user can select a microsecond inactive phase time. In embodiments, the microsecond inactive phase is at least about 80 microseconds. In embodiments, the microsecond inactive phase is at least 80 microseconds up to 10,000 microseconds, 200 microseconds up to 10,000 microseconds, or 400 microseconds up to 10,000 microseconds.

In embodiments, a user can select a millisecond active phase. In embodiments, the millisecond active phase is at least 0.16 millisecond. In embodiments, the millisecond active phase is 0.16 millisecond to 1,100 milliseconds, 0.16 millisecond to 900 milliseconds, 0.16 millisecond to 800 milliseconds, 0.16 millisecond to 700 milliseconds, 0.16 millisecond to 600 milliseconds, 0.16 millisecond to 500 milliseconds, 0.16 to 400 milliseconds, 0.16 to 300 milliseconds, 0.16 to 200 milliseconds, 0.16 to 100 milliseconds, 0.16 to 50 milliseconds, 0.16 to 40 milliseconds, 0.16 to 30 milliseconds, 0.16 to 20 milliseconds, 0.16 to 10 milliseconds, or 0.16 to 5 milliseconds. In embodiments, the millisecond active phase is at least 1 millisecond. In other embodiments, the millisecond active phase is 1 to 1,100 milliseconds, 1 millisecond to 900 milliseconds, 1 millisecond to 800 milliseconds, 1 millisecond to 700 milliseconds, 1 millisecond to 600 milliseconds, 1 millisecond to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, 1 to 10 milliseconds, or 1 to 5 milliseconds.

In embodiments, a user can select the time of a millisecond inactive phase. In embodiments, the millisecond inactive phase is at least 0.08 milliseconds. In embodiments, the millisecond inactive phase is 0.08 millisecond to 11,000 milliseconds, 0.08 millisecond to 9000 milliseconds, 0.08 millisecond to 8000 milliseconds, 0.08 millisecond to 7000 milliseconds, 0.08 millisecond to 6000 milliseconds, 0.08 millisecond to 5000 milliseconds, 0.08 to 4000 milliseconds, 0.08 to 3000 milliseconds, 0.08 to 2000 milliseconds, 0.08 to 1000 milliseconds, 0.08 to 500 milliseconds, 0.08 to 400 milliseconds, 0.08 to 300 milliseconds, 0.08 to 200 milliseconds, 0.08 to 100 milliseconds, 0.08 to 50 milliseconds, 0.08 to 40 milliseconds, 0.08 to 30 milliseconds, 0.08 to 20 milliseconds, or 0.08 to 10 milliseconds. In embodiments, the millisecond inactive phase is 1 millisecond to 11,000 milliseconds, 1 millisecond to 9000 milliseconds, 1 millisecond to 8000 milliseconds, 1 millisecond to 7000 milliseconds, 1 millisecond to 6000 milliseconds, 1 millisecond to 5000 milliseconds, 1 to 4000 milliseconds, 1 to 3000 milliseconds, 1 to 2000 milliseconds, 1 to 1000 milliseconds, 1 to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, or 1 to 10 milliseconds.

In embodiments, a user can select an on time. In embodiments, an on time can be selected from 30 seconds to about 30 minutes, 30 seconds to about 15 minutes, 30 seconds to about 10 minutes, 30 seconds to about 5 minutes, 30 seconds to about 2 minutes, or 30 seconds to about 1 minute.

In embodiments, a user can select an off time. In embodiments, off times are at least about 30 seconds. In other embodiments, the off time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute.

Optionally, a user may select a % of duty cycle for a microsecond and/or millisecond cycle. In embodiments, a user can select a duty cycle of 100% or less, 90% or less, 80% or less, 70% or less, 60% or less, 50% or less, 40% or less, 30% or less, 20% or less, or 10% or less. In embodiments, a user can select a duty cycle of 75% or less.

Figure 15:
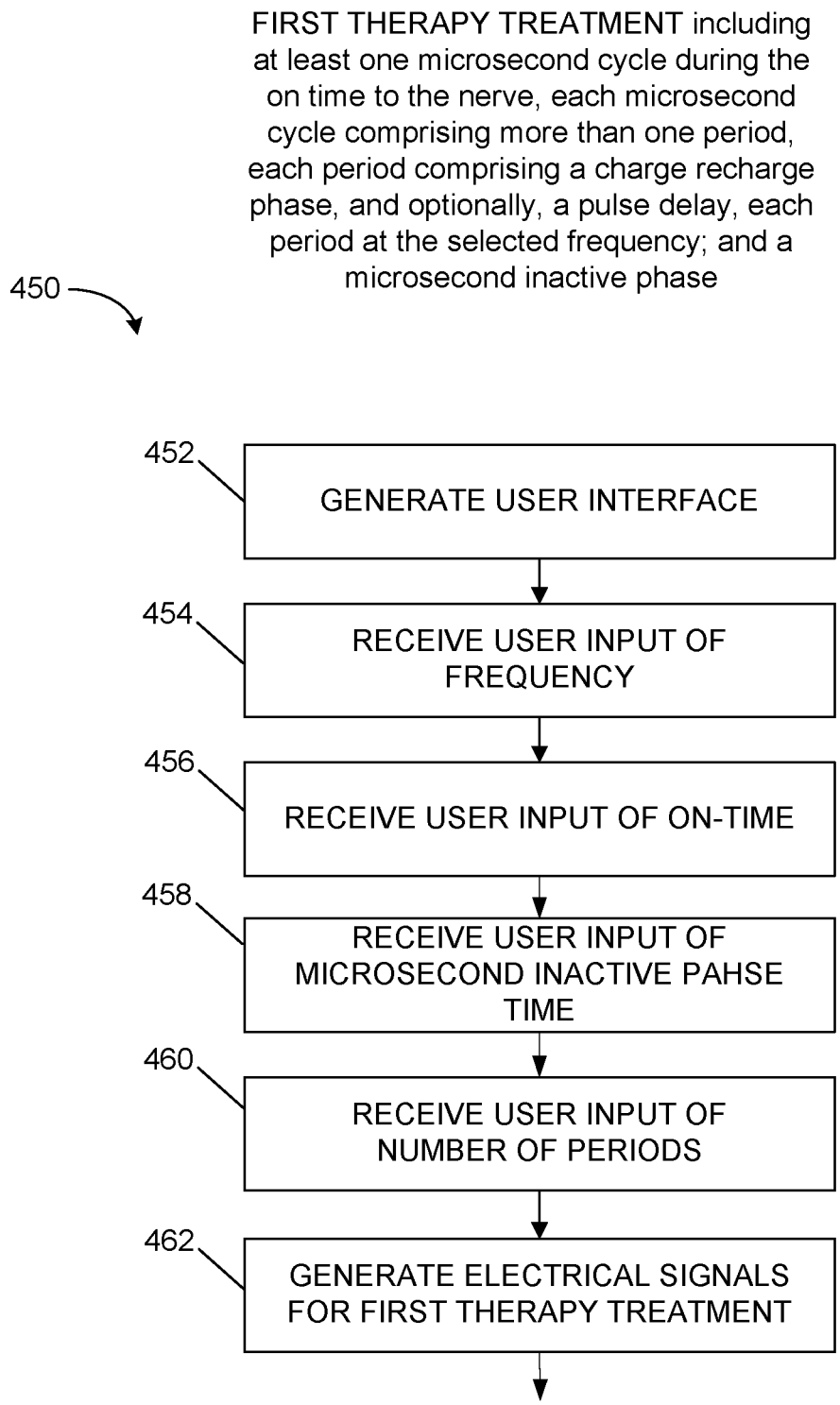
FIG. 15 is a flowchart illustrating an exemplary method for operation the therapy system for a first therapy program for regulating nerve activity.
Figure 16:
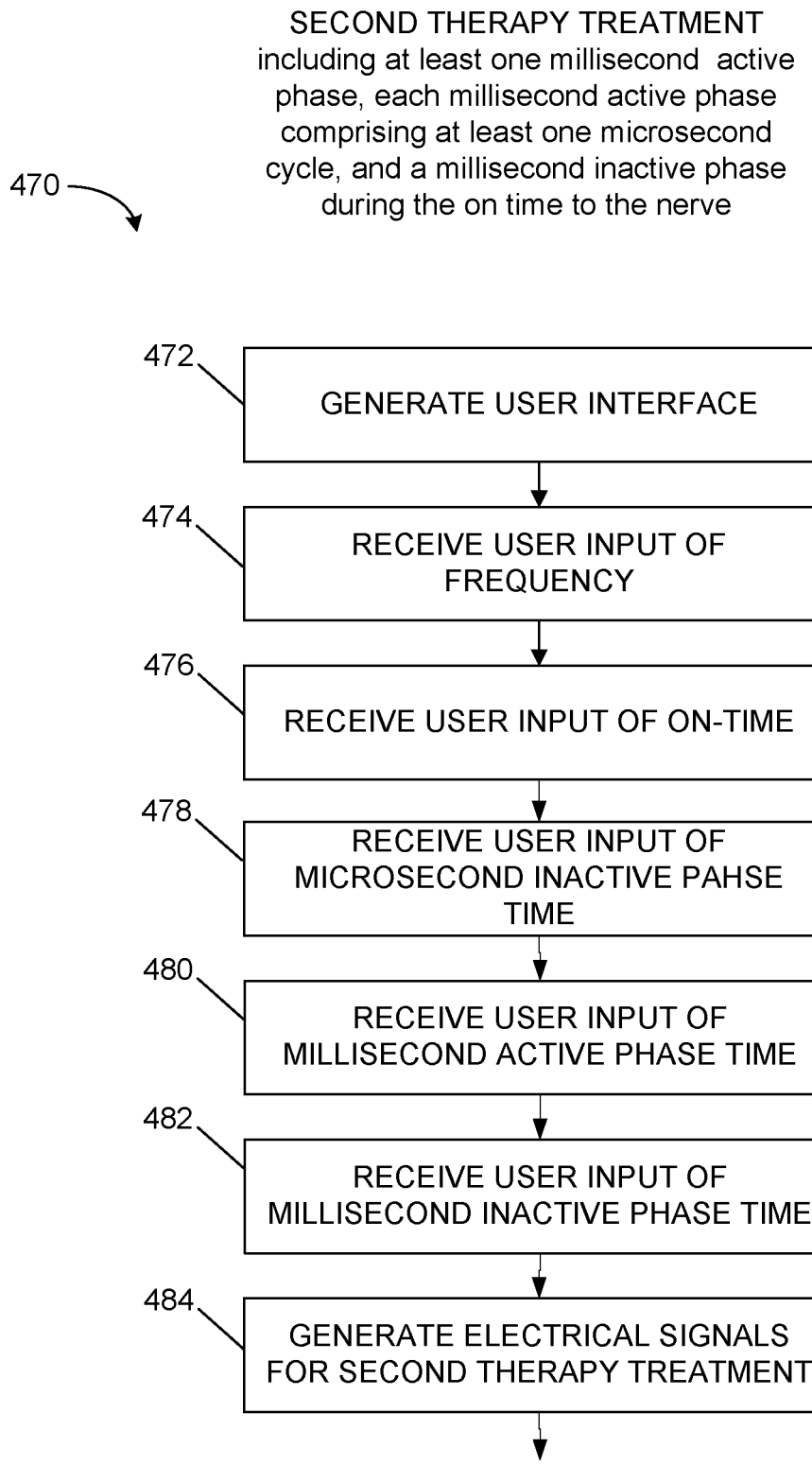
FIG. 16 is a flowchart illustrating an example method 470 for operation the therapy system for a second therapy program for regulating nerve activity.
Figure 17:
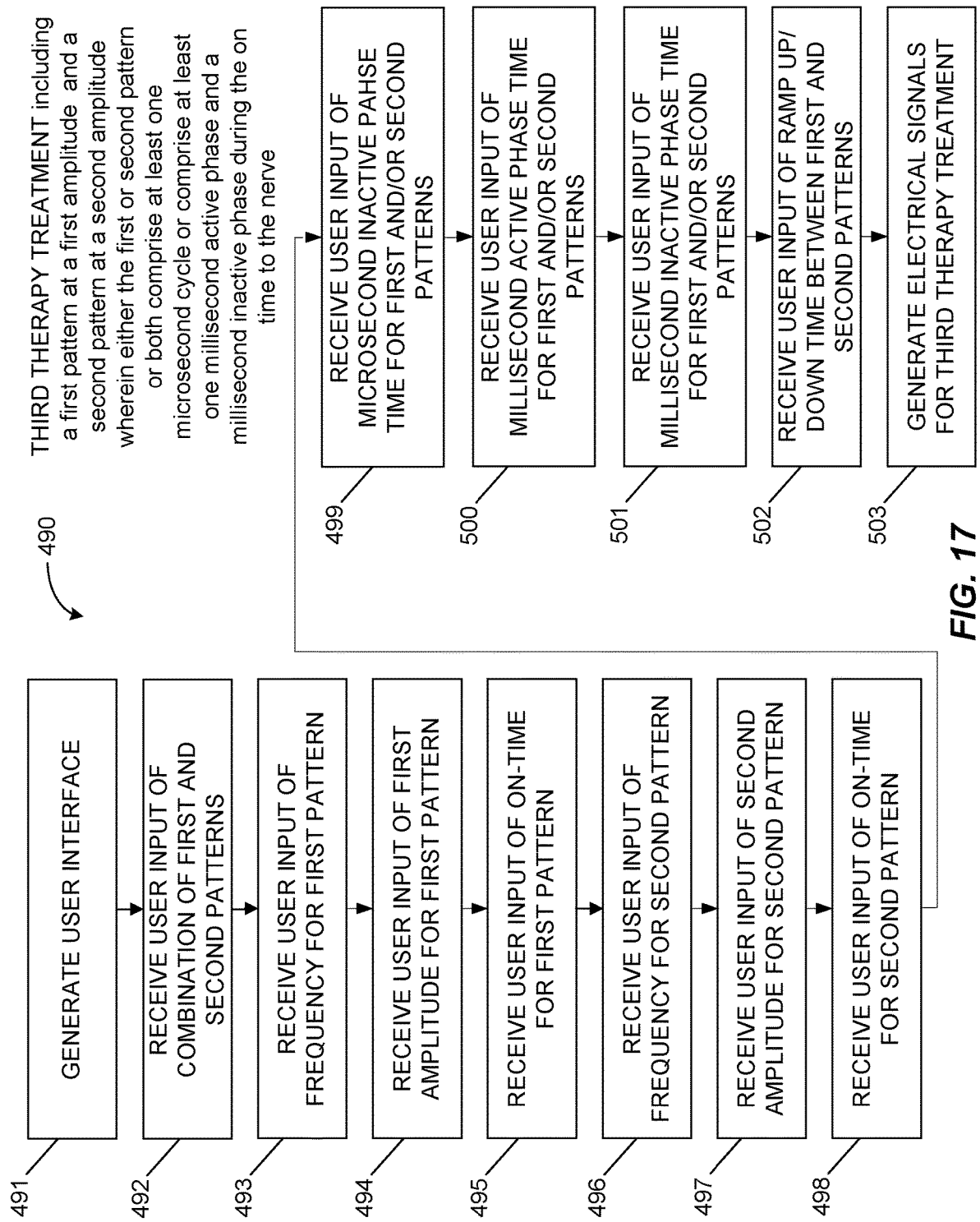
FIG. 17 is a flowchart illustrating an example method 490 for operation the therapy system for a third therapy program for regulating nerve activity.

Referring to FIGS. 15-17, example methods for operating the therapy system 100 are described for different therapy programs. In the illustrated examples, three different therapy programs are described. However, the system 100 can operate to provide other therapy programs in accordance with the present disclosure.

FIG. 15 is a flowchart illustrating an example method 450 for operating the therapy system 100 for a first therapy program. At operation 452, the system 100 generates a user interface for enabling a user to input one or more parameters for the first therapy program. At operation 454, the system 100 receives a user input of a frequency parameter via the user interface. At operation 456, the system 100 receives a user input of an on-time parameter via the user interface. At operation 458, the system 100 receives a user input of a microsecond inactive time parameter via the user interface. At operation 460, the system 100 receives a user input of a number of periods via the user interface. In some embodiments, the system 100 receives additional parameters including, but not limited to, amplitude, a pulse width or pulse delay time, and a ramp up/down time. In other embodiments, the system 100 receives only some of the parameters described above. At operation 462, the system 100 generates electrical signals for the first therapy treatment based on the inputted parameters. The first therapy treatment can include at least one microsecond cycle during the on time to the nerve, each microsecond cycle comprising more than one period, each period comprising a charge recharge phase, and optionally, a pulse delay, each period at the selected frequency; and a microsecond inactive phase.

The method 450 illustrates one example operation of the system 100 for the first therapy program. In some embodiments, the method 450 includes only some of the operations described above. In other embodiments, the method 450 includes additional operations along with all or some of the operations described above.

FIG. 16 is a flowchart illustrating an example method 470 for operating the therapy system 100 for a second therapy program. At operation 472, the system 100 generates a user interface for enabling a user to input one or more parameters for the second therapy program. At operation 474, the system 100 receives a user input of a frequency parameter via the user interface. At operation 476, the system 100 receives a user input of an on-time parameter via the user interface. At operation 478, the system 100 receives a user input of a microsecond inactive time parameter via the user interface. At operation 480, the system 100 receives a user input of a millisecond active phase time via the user interface. At operation 482, the system 100 receives a user input of a millisecond inactive phase time via the user interface. In some embodiments, the system 100 receives additional parameters. In other embodiments, the system 100 receives only some of the parameters described above. At operation 462, the system 100 generates electrical signals for the second therapy treatment based on the inputted parameters. The second therapy treatment can include at least one millisecond active phase, each millisecond active phase comprising at least one microsecond cycle, and a millisecond inactive phase during the on time to the nerve The method 470 illustrates one example operation of the system 100 for the second therapy program. In some embodiments, the method 470 includes only some of the operations described above. In other embodiments, the method 470 includes additional operations along with all or some of the operations described above.

FIG. 17 is a flowchart illustrating an example method 490 for operating the therapy system 100 for a third therapy program. At operation 491, the system 100 generates a user interface for enabling a user to input one or more parameters for the third therapy program. At operation 492, the system 100 receives a user selection of a combination of first and second patterns via the user interface. At operation 493, the system 100 receives a user input of a first frequency parameter for the first pattern via the user interface. At operation 494, the system 100 receives a user input of a first amplitude for the first pattern via the user interface. At operation 495, the system 100 receives a user input of an on-time parameter for the first pattern via the user interface. At operation 496, the system 100 receives a user input of a second frequency parameter for the second pattern via the user interface. At operation 497, the system 100 receives a user input of a second amplitude for the second pattern via the user interface. At operation 498, the system 100 receives a user input of an on-time parameter for the second pattern via the user interface. At operation 499, the system 100 receives a user input of a microsecond inactive phase time parameter for the first and/or second patterns via the user interface. At operation 500, the system 100 receives a user input of a millisecond active phase time for the first and/or second patterns via the user interface. At operation 501, the system 100 receives a user input of a millisecond inactive phase time for the first and/or second patterns via the user interface. At operation 502, the system 100 receives a user input of a ramp up and/or down time parameters via the user interface. In some embodiments, the system 100 receives additional parameters. In other embodiments, the system 100 receives only some of the parameters described above. At operation 503, the system 100 generates electrical signals for the third therapy treatment based on the inputted parameters. The third therapy treatment can include a first pattern at a first amplitude and a second pattern at a second amplitude wherein either the first or second pattern or both comprise at least one microsecond cycle or comprise at least one millisecond active phase and a millisecond inactive phase during the on time to the nerve.

The method 490 illustrates one example operation of the system 100 for the third therapy program. In some embodiments, the method 490 includes only some of the operations described above. In other embodiments, the method 470 includes additional operations along with all or some of the operations described above.

As described herein, a user interface provides any one or all of the above parameters. In some embodiments, the parameters may have default values. In other embodiments, each parameters can have one or more options for selection as described herein.

In embodiments, a user interface can provide at least three different therapy programs. If a first therapy program is selected, a user may select a frequency, an on time, the number of periods, a microsecond inactive time, an amplitude, and optionally, a pulse width or pulse delay time and ramp up/down time. The first program then provides an electrical signal treatment comprising multiple microsecond cycles during the on time at the selected frequency, each microsecond cycle comprising more than one period, each period comprising a charge recharge phase, and optionally, a pulse delay, each period at the selected frequency; and a microsecond inactive phase.

If a second therapy program is selected, a user selects the frequency, an amplitude, a microsecond inactive phase time, a millisecond active phase time, a millisecond inactive phase time, and an on time. In embodiments, the second program then provides an electrical signal treatment that comprises at least one millisecond active phase during an on time, each millisecond active phase comprising at least microsecond cycle; and a millisecond inactive phase.

If a third therapy program is selected, a user selects a first pattern comprising a frequency, a first amplitude, and an on time; and a second pattern comprising a second frequency, a second amplitude; and a second on time. A user then further selects for either the first or second pattern or both, a microsecond inactive phase time, a millisecond active phase time, and a millisecond inactive phase time. Optionally a user selects a ramp up and/or ramp down time between the first and second patterns. In embodiments, the third program provides an electrical signal treatment that comprises a first pattern of electrical signal at a first amplitude and a second pattern at a second amplitude.

In another aspect of the disclosure, a computer implemented method and a computer readable medium are provided. In embodiments, the computer readable medium comprises executable instructions for implementing an electrical signal therapy for downregulating and/or upregulating activity on a nerve in a subject comprising providing at least one frequency for selection, providing at least one on time for selection, providing at least one microsecond inactive phase time for selection, providing for a number of periods, and once selections are made, providing instructions for applying an electrical signal treatment comprising at least one microsecond cycle during the on time to the nerve, each microsecond cycle comprising more than one period, each period comprising a charge recharge phase, and optionally, a pulse delay, each period at the selected frequency; and a microsecond inactive phase.

In other embodiments, a computer readable medium comprises executable instructions for implementing an electrical signal therapy for downregulating and/or upregulating activity on a nerve in a subject comprising providing at least one frequency for selection, providing at least one on time for selection, providing at least one microsecond inactive phase time for selection, providing at least one millisecond active phase time for selection, providing at least one millisecond inactive phase time for selection; and once selections are made, providing instructions for applying an electrical signal treatment comprising at least one millisecond active phase, each millisecond active phase comprising at least one microsecond cycle, and a millisecond inactive phase during the on time to the nerve.

In yet other embodiments, a computer readable medium comprises executable instructions for implementing an electrical signal therapy for downregulating and/or upregulating activity on a nerve comprising providing a first pattern of electrical signal comprising providing at least one frequency for selection, providing a first amplitude for selection, and providing a first on time; providing a second pattern for selection comprising providing at least one frequency, providing a second amplitude, and providing a second on time. Further embodiments, comprise providing for microsecond inactive phase time for selection in the first or second pattern or both, providing at least one millisecond active phase time for selection in the first or second pattern or both, providing at least one millisecond inactive phase time for selection in the first or second pattern or both; and once selections are made, providing instructions for applying an electrical signal treatment comprising a first pattern at a first amplitude and a second pattern at a second amplitude wherein either the first or second pattern or both comprise at least one microsecond cycle or comprise at least one millisecond active phase and a millisecond inactive phase during the on time to the nerve. Embodiments further comprise providing for a ramp up and ramp down time, and once selections are made providing instructions to apply a ramp up or ramp down time between the first and second pattern.

In embodiments, a computer implemented method comprises applying an electrical signal to a nerve at a selected frequency, a selected on time, a selected number of periods, and a selected microsecond inactive phase time, wherein the electrical signal comprises at least one microsecond cycle during an on time, each microsecond cycle comprising more than one period, each period comprising a charge recharge phase, and optionally, a pulse delay, each period having a frequency of at least 1000 Hz; and a microsecond inactive phase. In embodiments, the method comprises selecting a frequency, selecting an on time, selecting the number of periods, and selecting a microsecond inactive phase time.

In embodiments, a computer implemented method comprises applying an electrical signal to a nerve at a selected frequency, a selected on time, a selected microsecond inactive phase time, a selected millisecond active phase time, and a selected millisecond inactive phase time, wherein the electrical signal comprises at least one millisecond active phase, each millisecond active phase comprising at least one microsecond cycle, and a millisecond inactive phase during the on time to the nerve.

In yet other embodiments, a computer implemented method comprises applying an electrical signal therapy for downregulating activity on a nerve comprising applying a first pattern of electrical signal comprising a selected frequency, a selected on time, a selected first amplitude, applying a second pattern of electrical signal comprising a selected second frequency, a selected second amplitude, and a second selected on time; further providing for a selected microsecond inactive phase time in the first or second pattern or both, providing a selected millisecond active phase time in the first or second pattern or both, providing a selected millisecond inactive phase time in the first or second pattern or both; and applying an electrical signal treatment comprising a first pattern at a first amplitude and a second pattern at a second amplitude, wherein either the first or second pattern or both comprise at least one microsecond cycle or comprise at least one millisecond active phase and a millisecond inactive phase during the on time to the nerve. Embodiments further comprises applying a selected ramp up and/ramp down time between the first and second pattern.

5. Therapy Schedule

In embodiments, to initiate the therapy regimen, the clinician downloads therapy parameters and/or one or more therapy programs, and a therapy schedule from an external computer, smartphone or tablet 107 to the external charger 101. In general, the therapy parameters indicate configuration values for the neuroregulator 101. For example, in the case of vagal nerve therapy for obesity, the therapy parameters may define the pulse amplitude with a fixed but selectable voltage or current, frequency, microsecond inactive phase time, millisecond active phase time, millisecond inactive phase time, pulse width, pulse delay, ramp up, ramp down, on time, off time, waveform shape and pattern of electrical pulses in a cycle for the electrical signals emitted by the implanted neuroregulator 104.

In general, the therapy schedule indicates a therapy cycle start time, the number of therapy cycles, timing of therapy cycles and duration of the delivery of therapy cycles for at least one day of the week. A therapy cycle refers to a discrete period of time (e.g. on the order of minutes) that contains one or more on times and off times. The pattern of on and off times can be repetitive, non-fixed or randomized throughout a therapy schedule. Preferably, the clinician programs a therapy schedule start time and duration for each day of a predetermined period, such as a week, month, time patient is on vacation, or time to next follow-up visit. In an embodiment, multiple therapy cycles can be scheduled within a single day. Therapy can also be withheld for one or more days at the determination of the clinician.

During a therapy schedule the neuroregulator 104 completes one or more therapy cycles. Typically, each therapy schedule includes multiple therapy cycles. The clinician has the ability to program the duration of each therapy cycle (i.e., via the clinician computer, smartphone or tablet 107).

When configured in the "on" state, the neuroregulator applies therapy (i.e., emits an electrical signal) as has been described herein. The neuroregulator 104 is then cycled to an "off" state, during which no signal is emitted by the neuroregulator 104, at intermittent periods (on the order of minutes). Such a therapy cycle may mitigate the chances of accommodation by the patient's body. A long off state also has the advantage of saving energy.

The therapy schedule indicates the times during the day when one or multiple therapy cycles are scheduled to be applied to a patient. In one embodiment, as an illustrative example, one or multiple therapy cycles can be scheduled between 8 AM and 9 AM. In certain embodiments, the therapy parameters indicates details of the pulse amplitude with a fixed but selectable voltage or current, frequency, pulse width, pulse delays, microsecond inactive phase time, millisecond active phase time, millisecond inactive phase time, ramp up, ramp down, on time, off time, waveform shape and pattern of active/inactive phases in a cycle. As an illustrative example, a therapy cycle may define an on period wherein one or more sets of pulses are delivered to the nerve for two minutes, followed by an off period of one minute where no pulses are delivered. A second on period of two minutes may follow the initial off period, followed by an off period of five minutes, wherein the cycle repeats itself. The therapy schedule may then continue for a period of six to twenty four hours as determined by the physician.

B. Methods

In another aspect of the disclosure, the systems and methods of the disclosure are useful to downregulate and/or upregulate activity on a nerve of a subject including but not limited to the vagus nerve, renal nerve, renal artery, sympathetic nerves, glossopharyngeal nerve, celiac nerve, and combinations thereof. The systems and methods are useful in treating gastrointestinal disorders, obesity and eating disorders, pancreatitis and other inflammatory conditions, ulcerative colitis, Crohn's disease, diabetes, prediabetes, hypertension, and congestive heart failure.

In embodiments, a method of treating gastrointestinal disorders comprises applying an electrical signal to downregulate nerve activity to a nerve of a subject by applying the electrical signal to the nerve during an on time, wherein the electrical signal comprises more than one microsecond cycle comprising more than one period, each period comprising a charge recharge phase, and optionally, a pulse delay, each period having a frequency of at least 1000 Hz; and a microsecond inactive phase. In embodiments, parameters of the electrical signal downregulate activity of the nerve. In embodiments, the nerve is selected from the group consisting of the vagus nerve, the renal nerve, the renal artery, splanchnic nerve, celiac plexus, and combinations thereof.

In other embodiments, the method of treating gastrointestinal disorders comprises applying an electrical signal to a nerve of a subject, wherein the electrical signal comprises more than one microsecond cycle to form a millisecond active phase, and applying more than one millisecond active phase during the on time, wherein each millisecond active phase is separated by a millisecond inactive phase during the on time. In embodiments, the millisecond inactive phase is longer than the millisecond active phase. In embodiments, the millisecond inactive phase can vary in time between each millisecond active phase. In embodiments, parameters of the electrical signal downregulate activity of the nerve. In embodiments, the nerve is selected from the group consisting of the vagus nerve, the renal nerve, the renal artery, splanchnic nerve, celiac plexus, and combinations thereof.

In yet other embodiments, a method of treating gastrointestinal disorders comprises applying an electrical signal to a nerve of a subject by applying the electrical signal to the nerve during an on time, wherein the electrical signal comprises a first pattern comprising at least one microsecond cycle; and a second pattern comprising more than one millisecond active phase, wherein each millisecond active phase comprises more than one microsecond cycle, and each millisecond active phase is separated by a millisecond inactive phase. In embodiments, the first and second patterns have a different amplitude. In embodiments, the microsecond cycle comprises at least one period comprising a charge recharge phase, and optionally, a pulse delay, each period having a frequency of at least 200 Hz; and a microsecond inactive phase. In embodiments, the first pattern has an amplitude greater than the second pattern. In embodiments, the first pattern has an on time and the second pattern has on times that differ from one another. In embodiments, the nerve is selected from the group consisting of the vagus nerve, the renal nerve, the renal artery, splanchnic nerve, celiac plexus, and combinations thereof.

In embodiments, methods for treating gastrointestinal conditions are performed where the nerve is selected from the vagus nerve and its individual branches and/or splanchnic nerve, and/or celiac complex. In embodiments, at least one electrode is placed on or near the vagus nerve. In embodiments, gastrointestinal disease includes obesity, overweight, pancreatitis, dysmotility, bulimia, gastrointestinal disease with an inflammatory basis such as ulcerative colitis and Crohn's disease, low vagal tone, gastroparesis, reflux disease, peptic ulcers, or combinations thereof. In embodiments, the electrical signal therapy can be combined with administration of therapeutic agents that affect energy regulation. In embodiments, the methods include the electrical signal parameters, systems, computer readable media, and computer implemented methods as described herein.

In embodiments, a method of treating disorders of blood glucose regulation comprises applying an electrical signal having parameters that downregulate nerve activity to a nerve of a subject by applying the electrical signal to the nerve during an on time, wherein the electrical signal comprises more than one microsecond cycle comprising at least one period comprising a charge recharge phase and optionally, a pulse delay, each period having a frequency of at least 1000 Hz; and a microsecond inactive phase.

In other embodiments, the method of treating disorders of blood glucose regulation comprises applying an electrical signal to a nerve of a subject, wherein the electrical signal comprises more than one microsecond cycle to form a millisecond active phase, and applying more than one millisecond active phase during the on time, wherein each millisecond active phase is separated by a millisecond inactive phase during the on time. In embodiments, the millisecond inactive phase is longer than the millisecond active phase. In embodiments, the millisecond inactive phase can vary in time between each millisecond active phase.

In yet other embodiments, a method of treating disorders of blood glucose regulation comprises applying an electrical signal having a frequency to downregulate nerve activity to a nerve of a subject by applying the electrical signal to the nerve during an on time, wherein the electrical signal comprises a first pattern comprising at least one microsecond cycle; and a second pattern comprising more than one millisecond active phase, wherein each millisecond active phase comprises more than one microsecond cycle, and each millisecond active phase is separated by a millisecond inactive phase, wherein the first and second patterns have a different amplitude. In embodiments, the microsecond cycle comprises at least one period comprising a charge recharge phase, and optionally, a pulse delay, wherein each period has a frequency of at least 200 Hz; and a microsecond inactive phase. In embodiments, the first pattern has an amplitude greater than the second pattern.

In embodiments, the methods for treating disorders of glucose regulation, the nerve is selected from the group consisting of the vagus nerve, sympathetic nerves, splanchnic nerve, celiac plexus, and combinations thereof. In embodiments, at least one electrode is placed on or near the vagus nerve.

In embodiments, disorders of glucose regulation include diabetes, prediabetes, metabolic syndrome or combinations thereof. In embodiments, the methods of treating disorders of glucose regulation include also treating the disorders in combinations with drugs used to treat, diabetes, or prediabetes such as insulin and analogs thereof, GLP1 agonists, sulfonylureas, and the like. In embodiments, the methods include the electrical signal parameters, systems, computer readable media, and computer implemented methods as described herein.

In embodiments, a method of treating disorders of blood pressure and/or congestive heart failure comprises applying an electrical signal having parameters that downregulate nerve activity to a nerve in a subject by applying the electrical signal to the nerve during an on time, wherein the electrical signal comprises at more than one microsecond cycle comprising more than one period comprising a charge recharge phase, and optionally, a pulse delay, each period has a frequency of at least 1000 Hz; and a microsecond inactive phase.

In other embodiments, the method of treating disorders of blood pressure and/or congestive heart failure comprises applying an electrical signal to a nerve of a subject, wherein the electrical signal comprises more than one microsecond cycle to form a millisecond active phase, and applying more than one millisecond active phase during the on time, wherein each millisecond active phase is separated by a millisecond inactive phase during the on time. In embodiments, the millisecond inactive phase is longer than the millisecond active phase. In embodiments, the millisecond inactive phase can vary in time between each millisecond active phase.

In yet other embodiments, a method of treating disorders of blood pressure and/or congestive heart failure comprises applying an electrical signal having a frequency to downregulate nerve activity to a nerve of a subject by applying the electrical signal to the nerve during an on time, wherein the electrical signal comprises a first pattern comprising at least one microsecond cycle; and a second pattern comprising more than one millisecond active phase, wherein each millisecond active phase comprises more than one microsecond cycle, and each millisecond active phase is separated by a millisecond inactive phase. In embodiments, the first and second patterns have a different amplitude. In embodiments, the microsecond cycle comprises at least one period comprising a charge recharge phase, and optionally, a pulse delay, wherein each period has a frequency of at least 200 Hz; and a microsecond inactive phase. In embodiments, the first pattern has an amplitude greater than the second pattern. In embodiments, the method further comprises applying a ramp up and/or ramp down time between the first and second patterns.

In embodiments, the methods for treating disorders of blood pressure and/or congestive, the nerve is selected from the group consisting of the vagus nerve, renal nerve, renal artery, sympathetic nerves, baroreceptors, glossopharyngeal nerve, and combinations thereof. In embodiments, at least one electrode is placed on or near the vagus nerve. In other embodiments, at least one electrode is placed on or near renal nerve, renal artery, sympathetic nerves, baroreceptors, glossopharyngeal nerve, and/or on the vagus nerve.

In embodiments, disorders of blood pressure and/or congestive heart failure include hypertension, prehypertension, congestive heart failure, and combinations thereof. In embodiments, the methods of treating disorders of blood pressure include also treating the disorders in combinations with drugs used to treat hypertension and congestive heart failure including ACE inhibitors, diuretics, beta blockers, alpha blockers, angiotensin II receptor blockers, calcium channel blockers or combinations thereof. In embodiments, the methods include the electrical signal parameters, systems, computer readable media, and computer implemented methods as described herein.

In embodiments, the methods of treating disorders described above include the parameters as described herein with regard to methods of downregulating and/or upregulating nerve activity of nerve includes those of frequency, on times, amplitudes, ramp up and ramp down times.

In embodiments, the electrical signal has a frequency in each period of a microsecond cycle of at least 200 Hz, at least 250 Hz, at least 300 Hz, at least 400 Hz, at least 500 Hz, at least 1000 Hz, at least 2000 Hz, at least 3000 Hz, at least 4000 Hz, or at least 5000 Hz. In other embodiments, the frequencies range from about 200 Hz to 25 kHz, 200 Hz to 20 kHz, 200 Hz to 15 kHz, 200 Hz to 10 kHz, 200 to 5 kHz, 200 to 2.5 kHz, 200 to 1 kHz, or 200 to 500 Hz. In other embodiments, the frequencies range from about 1000 Hz to 25 kHz, 1000 Hz to 20 kHz, 1000 Hz to 15 kHz, 1000 Hz to 10 kHz, 1000 to 5 kHz, or 1000 Hz to 2.5 kHz. In other embodiments, the frequencies range from about 1000 Hz to 10 kHz, 1000 Hz to 9000 Hz, 1000 Hz to 8000 Hz, 1000 Hz to 7000 Hz, 1000 to 6000 Hz, 1000 Hz to 5000 Hz, 1000 Hz to 4000 Hz, 1000 Hz to 3000 Hz, or 1000 Hz to 2000 Hz.

In some embodiments, a user selects a frequency of 300 Hz or less. In embodiments, the electrical signal has a frequency of a period in a microsecond cycle. In embodiments, a period has a frequency of 300 Hz or less, 250 Hz or less, 200 Hz or less, 150 Hz or less, 100 Hz or less, 50 Hz or less, 10 Hz or less, 1 Hz or less. In embodiments, the electrical signal has a frequency of about 0.1 to 300 Hz, 0.1 to 250 Hz, 0.1 to 200 Hz, 0.1 to 150 Hz, 0.1 to 100 Hz, 0.1 to 50 Hz, 0.1 to 10 Hz, or 0.1 to 1 Hz. In embodiments, electrical signals at such frequencies can stimulate nerve activity.

In embodiments, the amplitude of the signal is at least 1 mAmp. In other embodiments, the amplitude ranges from about 1 to 20 mAmps, 1 to 15 mAmps, 1 to 10 mAmps, 1 to 8 mAmps, or 1 to 5 mAmps.

In embodiments, the amplitude is at least 1 volt. In other embodiments, the amplitude ranges from about 1 to 20 volts, 1 to 15 volts, 1 to 10 volts, 1 to 8 volts, or 1 to 5 volts.

In yet other embodiments, a user can select a ramp up and/or a ramp down time and amplitude. During the ramp up and ramp down time the amplitude is changing. In embodiments, the amplitudes for ramp up include about 0.1 to 20 mAmps, 0.1 to 15 mAmps, 0.1 to 10 mAmps, 0.1 to 8 mAmps, or 0.1 to 5 mAmps. In embodiments, the amplitude for a ramp up is at least 1 volt. In other embodiments, the amplitude ranges from about 1 to 20 volts, 1 to 15 volts, 1 to 10 volts, 1 to 8 volts, or 1 to 5 volts. In embodiments, the time or ramp up and/or ramp down is about 200 microseconds to 25 milliseconds.

In embodiments, the microsecond inactive phase is at least about 80 microseconds. In embodiments, the microsecond inactive phase is at least 80 microseconds up to 10,000 microseconds, 200 microseconds up to 10,000 microseconds, or 400 microseconds up to 10,000 microseconds.

In embodiments, the millisecond active phase is at least 0.16 millisecond. In embodiments, the millisecond active phase is 0.16 millisecond to 1,100 milliseconds, 0.16 millisecond to 900 milliseconds, 0.16 millisecond to 800 milliseconds, 0.16 millisecond to 700 milliseconds, 0.16 millisecond to 600 milliseconds, 0.16 millisecond to 500 milliseconds, 0.16 to 400 milliseconds, 0.16 to 300 milliseconds, 0.16 to 200 milliseconds, 0.16 to 100 milliseconds, 0.16 to 50 milliseconds, 0.16 to 40 milliseconds, 0.16 to 30 milliseconds, 0.16 to 20 milliseconds, 0.16 to 10 milliseconds, or 0.16 to 5 milliseconds. In embodiments, the millisecond active phase is at least 1 millisecond. In other embodiments, the millisecond active phase is 1 to 1,100 milliseconds, 1 millisecond to 900 milliseconds, 1 millisecond to 800 milliseconds, 1 millisecond to 700 milliseconds, 1 millisecond to 600 milliseconds, 1 millisecond to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, 1 to 10 milliseconds, or 1 to 5 milliseconds.

In embodiments, the millisecond active phase comprises at least 2 to 100 microsecond cycles, at least 2 to 90, at least 2 to 80, at least 2 to 70, at least 2 to 60, at least 2 to 50, at least 2 to 40, at least 2 to 30, at least 2 to 20, at least 2 to 10, at least 2 to 5, or at least 2 to 4 microsecond cycles.

In embodiments, the millisecond inactive phase is in a ratio to the millisecond active phase of about 10 to 1, 8 to 1, 6 to 1, 4 to 1, 2 to 1 or 1 to 2. In embodiments, the millisecond inactive phase is at least 0.08 milliseconds. In embodiments, the millisecond inactive phase is 0.08 millisecond to 11,000 milliseconds, 0.08 millisecond to 9000 milliseconds, 0.08 millisecond to 8000 milliseconds, 0.08 millisecond to 7000 milliseconds, 0.08 millisecond to 6000 milliseconds, 0.08 millisecond to 5000 milliseconds, 0.08 to 4000 milliseconds, 0.08 to 3000 milliseconds, 0.08 to 2000 milliseconds, 0.08 to 1000 milliseconds, 0.08 to 500 milliseconds, 0.08 to 400 milliseconds, 0.08 to 300 milliseconds, 0.08 to 200 milliseconds, 0.08 to 100 milliseconds, 0.08 to 50 milliseconds, 0.08 to 40 milliseconds, 0.08 to 30 milliseconds, 0.08 to 20 milliseconds, or 0.08 to 10 milliseconds. In embodiments, the millisecond inactive phase is 1 millisecond to 11,000 milliseconds, 1 millisecond to 9000 milliseconds, 1 millisecond to 8000 milliseconds, 1 millisecond to 7000 milliseconds, 1 millisecond to 6000 milliseconds, 1 millisecond to 5000 milliseconds, 1 millisecond to 4000 milliseconds, 1 to 3000 milliseconds, 1 to 2000 milliseconds, 1 to 1000 milliseconds, 1 to 500 milliseconds, 1 to 400 milliseconds, 1 to 300 milliseconds, 1 to 200 milliseconds, 1 to 100 milliseconds, 1 to 50 milliseconds, 1 to 40 milliseconds, 1 to 30 milliseconds, 1 to 20 milliseconds, or 1 to 10 milliseconds.

In embodiments, the on time is at least about 30 seconds. In other embodiments, the on time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include on times of varying amounts. For example, a therapy cycle can include 1 minutes of on time, 1 minute of off time, 2 minutes of on time, followed by 5 minutes of off time.

In embodiments, the off time is selected in order to allow at least partial recovery of the nerve. In embodiments, the off time may be minimized due to the presence of microsecond inactive phases and/or millisecond inactive phases. In embodiments, off times are at least about 30 seconds. In other embodiments, the off time is about 30 seconds to 30 minutes, about 30 seconds to 25 minutes, about 30 seconds to 20 minutes, about 30 seconds to 15 minutes, about 30 seconds to 10 minutes, about 30 seconds to 5 minutes, about 30 seconds to 4 minutes, about 30 seconds to 3 minutes, about 30 seconds to 2 minutes, or about 30 seconds to one minute. In embodiments, a therapy cycle can include off times of varying amounts. For example, a therapy cycle can include 1 minutes of on time, 1 minute of off time, 2 minutes of on time, followed by 5 minutes of off time.

EXAMPLES

Experiments to test the ability of low duty cycle as illustrated in the exemplary embodiments in the figures to block a nerve as compared to high duty cycle were conducted on an isolated rat vagus nerve. Compound action potentials (hereinafter CAP) were elicited with a bipolar hook stimulation electrode and recorded with a bipolar hook recording electrode positioned at approximately 16 mm away from the stimulation electrode. A third bipolar hook electrode that delivered high frequency alternating current (HFAC) algorithms (either high duty cycle or low duty cycle) was positioned between the stimulation and recording electrode.

The amplitude of the CAP was measured for 1 min before the application of HFAC and within 1 second following cessation of HFAC. Baseline was calculated by taking the average amplitude of the CAPs for 1 min prior to the delivery of HFAC. Block was measured by taking the CAP amplitude following HFAC and dividing it by the baseline CAP amplitude.

With a HFAC amplitude in the range of about 6 mA it was determined that all of the exemplary low duty cycle electrical signal patterns as shown in FIGS. 6-10 blocked the nerve to the same degree as the high duty cycle algorithm depicted in FIG. 5. (data not shown)

Conduction along the vagus nerve did not recover immediately following HFAC for high or low duty cycle electrical signal treatment. The time of recovery was on the order of about 5 minutes. For high and low duty cycle electrical signal treatment recovery times were similar.

Modifications and equivalents of disclosed concepts such as those which might readily occur to one skilled in the art are intended to be included in the scope of the claims which are appended hereto. In addition, this disclosure contemplates application of a combination of electrical signal treatment by placement of electrodes on one or more nerves. This disclosure contemplates application of a therapy program to down regulate neural activity by application of an electrical signal treatment by placement of electrodes on one or more nerves. This disclosure contemplates application of a therapy program to up regulate neural activity by application of electrical signal treatment by placement of electrodes on one or more nerves. Any publications referred to herein are hereby incorporated by reference.

What is claimed is:

1. A method of applying an electrical signal having parameters that downregulate nerve activity to a nerve in a subject, the method comprising:
connecting a therapy system to a nerve of a subject, and
applying the electrical signal to the nerve during an on time, wherein the electrical signal comprises more than one millisecond active phases and at least one millisecond inactive phase, wherein each one of the millisecond active phases is separated by at least one of the at least millisecond inactive phases during the on time, wherein each one of the millisecond active phases comprises at least one microsecond cycle, wherein each of the at least one microsecond cycle comprises at least one period and at least one microsecond inactive phase, wherein each of the at least one period comprises a charge phase and a recharge phase, wherein the electrical signal has a frequency of the period of at least 200 Hz.

2. The method of claim 1, wherein the microsecond inactive phase is longer than the period.

3. The method of claim 1, wherein each charge and recharge phase further comprises a pulse delay between the charge and recharge phase.

4. The method of claim 3, wherein each charge and recharge phase further comprises a pulse delay after the recharge phase.

5. The method of claim 1, wherein the on time is at least 30 seconds.

6. The method of claim 5, wherein the microsecond inactive phase is at least 2 times longer than the period.

7. The method of claim 6, wherein the millisecond active phase is at least 1 millisecond.

8. The method of claim 7, wherein the millisecond inactive phase is at least 1 millisecond.

9. The method of claim 8, wherein the ratio of the millisecond inactive phase to the millisecond active phase is at least about 1 to 2.

10. The method of claim 1, wherein the therapy system further comprises an external charger.

11. The method of claim 1, wherein the therapy system is wirelessly connected to the nerve.

* * * * *